US010155069B2

(12) United States Patent
Abdalla et al.

(10) Patent No.: US 10,155,069 B2
(45) Date of Patent: Dec. 18, 2018

(54) BONE GRAFT WITH A TANNIN-HYDROXYAPATITE SCAFFOLD AND STEM CELLS FOR BONE ENGINEERING

(71) Applicant: King Abdulaziz University, Jeddah (SA)

(72) Inventors: Soliman Mahmoud Soliman Abdalla, Jeddah (SA); Fahad Al-Marzouki, Jeddah (SA); Antonio Pizzi, Epinal (FR); Fatma Salem Bahabri, Jeddah (SA)

(73) Assignee: King Abdulaziz University, Jeddah (SA)

( * ) Notice: Subject to any disclaimer, the term of this patent is extended or adjusted under 35 U.S.C. 154(b) by 39 days.

(21) Appl. No.: 15/261,037

(22) Filed: Sep. 9, 2016

(65) Prior Publication Data
US 2018/0071433 A1   Mar. 15, 2018

(51) Int. Cl.
| | | |
|---|---|---|
| *A61L 27/38* | (2006.01) | |
| *A61L 27/12* | (2006.01) | |
| *A61L 27/18* | (2006.01) | |
| *A61L 27/56* | (2006.01) | |
| *A61L 27/54* | (2006.01) | |
| *A61L 27/36* | (2006.01) | |
| *A61L 27/58* | (2006.01) | |
| *G01N 33/15* | (2006.01) | |
| *G01N 33/50* | (2006.01) | |

(52) U.S. Cl.
CPC .......... *A61L 27/3821* (2013.01); *A61L 27/12* (2013.01); *A61L 27/18* (2013.01); *A61L 27/3608* (2013.01); *A61L 27/54* (2013.01); *A61L 27/56* (2013.01); *A61L 27/58* (2013.01); *G01N 33/15* (2013.01); *G01N 33/50* (2013.01); *A61L 2300/414* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 6,043,350 | A | 3/2000 | Roll et al. |
| 9,302,413 | B2 | 4/2016 | Pizzi et al. |
| 2006/0194918 | A1 | 8/2006 | Pizzi et al. |
| 2011/0104230 | A1 | 5/2011 | Mousa et al. |
| 2014/0158927 | A1 | 6/2014 | Pizzi et al. |
| 2014/0193322 | A1 | 7/2014 | Celzard et al. |
| 2015/0010607 | A1 | 1/2015 | Francis et al. |
| 2015/0259460 | A1 | 9/2015 | Pizzi et al. |
| 2015/0274921 | A1 | 10/2015 | Celzard et al. |
| 2015/0361240 | A1 | 12/2015 | Pizzi et al. |

FOREIGN PATENT DOCUMENTS

| | | |
|---|---|---|
| CA | 2 886 961 A1 | 4/2014 |
| EP | 2 951 223 A1 | 12/2015 |
| WO | WO 2012/034519 A1 | 3/2012 |
| WO | WO 2013/010668 A1 | 1/2013 |

OTHER PUBLICATIONS

Gisele Amaral-Labat, et al., "Highly mesoporous organic aerogels derived from soy and tannin", Green Chemistry, vol. 14, 2012, pp. 3099-3106.
Ling Qin, et al., "Phytomolecule icaritin incorporated PLGA/TCP scaffold for steroid-associated osteonecrosis: Proof-of-concept for prevention of hip joint collapse in bipedal emus and mechanistic study in quadrupedal rabbits", Biomaterials, vol. 59, Aug. 2015, pp. 125-143.
Han QQ, et al., "The role of small molecules in bone regeneration", Future Med. Chem., vol. 5, No. 14, Sep. 2013, pp. 1671-1684 (Abstract only).
G. Krithiga, et al., "In vitro study on biomineralization of biphasic calcium phosphate biocomposite crosslinked with hydrolysable tannins of *Terminalia chebula*", Bulletin of Materials Science, vol. 34, No. 3, Jun. 2011, pp. 589-594.
C. Lacoste, et al., "Pine tannin-based rigid foams: Mechanical and thermal properties", Industrial Crops and Products, vol. 43, 2013, pp. 245-250.
"Scientific Opinion on the safety and efficacy of tannic acid when used as feed flavouring for all animal species", European Food Safety Authority, EFSA Journal, vol. 12, No. 10, 2014, 18 pages.
A. Szczurek, et al., "The use of tannin to prepare carbon gels. Part I: Carbon aerogels", Carbon, vol. 49, No. 8, 2011, pp. 2773-2784 (Abstract only).
A. Szczurek, et al., "The use of tannin to prepare carbon gels. Part II: Carbon cryogels", Carbon, vol. 49, No. 8, 2011, pp. 2785-2794 (Abstract only).
G. Amaral-Labat, et al., "Pore structure and electrochemical performances of tannin-based carbon cryogels", Biomass and Bioenergy, vol. 39, 2012, pp. 274-282.
L.I. Grishechko, et al., "New tannin-lignin aerogels", Industrial Crops and Products, vol. 41, 2013, pp. 347-355.
Amine Moubarik, et al., "Preparation and Mechanical Characterization of Particleboard Made From Maritime Pine and Glued With Bio-Adhesives Based on Cornstarch and Tannins", Maderas Ciencia Y Tecnologia, vol. 12, No. 3, 2010, pp. 189-197.
Maria Cecilia Basso, et al., "A New Approach to Environmentally Friendly Protein Plastics and Foams", Bioresources, vol. 10, No. 4, 2015, pp. 8014-8024.
M.C. Lagel, et al., "Cutting and grinding wheels for angle grinders with a bioresin matrix", Industrial Crops and Products, vol. 67, 2015, pp. 264-269.

(Continued)

*Primary Examiner* — Allison M Fox
(74) *Attorney, Agent, or Firm* — Oblon, McClelland, Maier & Neustadt, L.L.P.

(57) ABSTRACT

A biocompatible bone graft for implanting into a bone wound site or screening a bone disease drug, comprising a porous scaffold structure made from a tannin-hydroxyapatite resin, a population of osteocompetent stem cells, and a growth medium. Methods of synthesis and physical characterization of the porous scaffold structure are described, as well as biological testing of the osteocompetent stem cells of the bone graft.

20 Claims, 94 Drawing Sheets

(56) References Cited

OTHER PUBLICATIONS

M.C. Lagel, et al., "Automotive brake pads made with a bioresin matrix", Industrial Crops and Products, vol. 85, 2016, pp. 372-381.
Andrew Clegg, et al., "Frailty in elderly people", Seminar, www.thelancet.com, vol. 381, Issue 9868, Mar. 2-8, 2013, pp. 752-762.
Karin A. Hing, "Bone repair in the twenty-first century: biology, chemistry or engineering?", Phil. Trans. R. Soc. Lond. A, The Royal Society, vol. 362, 2004, pp. 2821-2850.
R. O. C. Oreffo, et al., "Future Potentials for Using Osteogenic Stem Cells and Biomaterials in Orthopedics", Bone, vol. 25, No. 2, Aug. 1999, pp. 5S-9S.
Giuseppe Maria De Peppo, et al., "Engineering bone tissue substitutes from human induced pluripotent stem cells", PNAS, vol. 110, No. 21, May 21, 2013, pp. 8680-8685.
G. Amaral-Labat, et al., "Tannin-based xerogels with distinctive porous structures", Biomass and Bioenergy, vol. 56, 2013, pp. 437-445.
Jean J. Kim, "Applications of iPSCs in Cancer Research", Biomarker Insights, vol. 10, Supplemental 1, 2015, pp. 125-131.
Kazutoshi Takahashi, et al., "Induction of Pluripotent Stem Cells from Adult Human Fibroblasts by Defined Factors", Cell, vol. 131, No. 5, Nov. 30, 2007, pp. 861-872.
Junying Yu, et al., "Human Induced Pluripotent Stem Cells Free of Vector and Transgene Sequences", Science, vol. 324, May 8, 2009, pp. 797-801.
Na Rae Han, et al., "Delivery of episomal vectors into primary cells by means of commercial transfection reagents", Biochemical and Biophysical Research Communications, vol. 461, 2015, pp. 348-353.
V. Crupi, et al., "Raman spectroscopic study of water in the poly(ethylene glycol) hydration shell", Journal of Molecular Structure, vol. 381, 1996, pp. 207-212.
Venkatachalam Natarajan, et al., "Preparation and properties of tannic acid cross-linked collagen scaffold and its application in wound healing", Journal of Biomedical Materials Research B: Applied Biomaterials, vol. 00B, Issue 00, 2012, 8 pages.
Nasim Annabi, M.S., et al., "Controlling the Porosity and Microarchitecture of Hydrogels for Tissue Engineering", Tissue Engineering: Part B, vol. 16, No. 4, 2010, pp. 371-383.
Rika Okaji, et al., "Interconnected pores on the walls of a polymeric honeycomb monolith structure created by the unidirectional freezing of a binary polymer solution", Journal of Materials Science, vol. 48, No. 5, 2013, pp. 2038-2045.
Blanca Vázquez, et al., "Acrylic bone cements modified with β-TCP particles encapsulated with poly(ethylene glycol)", Biomaterials, vol. 26, 2005, pp. 4309-4316.
Kelly M. Schultz, et al., "Measuring dynamic cell-material interactions and remodeling during 3D human mesenchymal stem cell migration in hydrogels", PNAS, Jul. 6, 2015, pp. E3757-E364.
Lucas T. Vu, et al., "Cell Migration on Planar and Three-Dimensional Matrices: A Hydrogel-Based Perspective", Tissue Engineering: Part B, vol. 21, No. 1, 2015, pp. 67-74.
Ghassemieh, Morphology and compression behaviour of biodegradable scaffolds produced by the sintering process, Proceedings of the Institution of Mechanical Engineers, Part H: Journal of Engineering in Medicine, vol. 222, No. 8, Nov. 1, 2008, pp. 1247-1262 (Abstract only).
Qiang Chen, et al., "Modelling of the strength-porosity relationship in glass-ceramic foam scaffolds for bone repair", Journal of the European Ceramic Society, vol. 34, No. 11, 2014, pp. 2663-2673.
Yu Zhang, et al., "In-situ hardening hydroxyapatite-based scaffold for bone repair", J. Mater. Sci: Mater. Med., vol. 17, No. 5, 2006, pp. 437-445.
Amir A. Al-Munajjed, et al., "Influence of pore size on tensile strength, permeability and porosity of hyaluronan-collagen scaffolds", J. Mater. Sci: Mater. Med., vol. 19, No. 8, 2008, pp. 2859-2864.
Robert Stern, et al., "The many ways to cleave hyaluronan", Biotechnology Advances, vol. 25, No. 6, 2007, pp. 537-557.
Pennella, et al., "A Survey of Methods for the Evaluation of Tissue Engineering Scaffold Permeability", Annals of Biomedical Engineering, vol. 41, No. 10, Oct. 2013, pp. 2027-2041.
Seungman Park, et al., "Microstructural Parameter-Based Modeling for Transport Properties of Collagen Matrices", Journal of Biological Engineering, vol. 137, No. 6, Jun. 2015, 9 pages.
Ami R. Amini, et al., "Bone Tissue Engineering: Recent Advances and Challenges", Crit. Rev. Biomed. Eng., vol. 40, No. 5, 2012, pp. 363-408.
Fupo He, et al., "Improvement of cell response of the poly(lactic-co-glycolic acid)/calcium phosphate cement composite scaffold with unidirectional pore structure by the surface immobilization of collagen via plasma treatment", Colloids and Surfaces B: Biointerfaces, vol. 103, 2013, pp. 209-216.
Hao-Xuan Zhang, et al., "Biocompatibility and osteogenesis of calcium phosphate composite scaffolds containing simvastatin-loaded PLGA microspheres for bone tissue engineering", Journal of Biomedical Materials Research A, vol. 103A, Issue 10, Oct. 2015, pp. 3250-3258.
Chelsea M. Magin, et al., "Bio-inspired 3D microenvironments: a new dimension in tissue engineering", Biomedical Materials, vol. 11, No. 2, Mar. 3, 2016, 12 pages.
Jianchun Lian, et al., "Effects of Serial Passage on the Characteristics and Cardiac and Neural Differentiation of Human Umbilical Cord Wharton's Jelly-Derived Mesenchymal Stem Cells", Hindawi Publishing Corporation, Stem Cells International, vol. 2016, 2016, 13 pages.
Tokiko Nagamlira-Inoue, et al., "Umbilical cord-derived mesenchymal stem cells: Their advantages and potential clinical utility", World Journal of Stem Cells, vol. 6, No. 2, Apr. 2014, pp. 195-202.
Vikram Rao, et al., "Adenosine Signaling Mediates Osteogenic Differentiation of Human Embryonic Stem Cells on Mineralized Matrices", Frontiers in Bioengineering and Biotechnology, vol. 3, Article 185, Nov. 2015, 10 pages.
Hwan D. Kim, et al., "High throughput approaches for controlled stem cell differentiation", Acta Biomaterialia, vol. 34, 2016, pp. 21-29.
A. Mangala Gowri, et al., "Foetal stem cell derivation & characterization for osteogenic lineage", Indian J. Med. Res., vol. 137, Feb. 2013, pp. 308-315.
Gulcihan Gulseren, et al., "Alkaline Phosphatase-Mimicking Peptide Nanofibers for Osteogenic Differentiation", Biomacromolecules, vol. 16, 2015, pp. 2198-2208.
Bryan N. Brown, et al., "Extracellular matrix as an inductive scaffold for functional tissue reconstruction", Translational Research, vol. 163, No. 4, Apr. 2014, pp. 268-285.
Maria Cecilia Basso, et al., "MALDI-TOF and $^{13}C$ NMR Analysis of Tannin-Furanic-Polyurethane Foams Adapted for Industrial Continuous Lines Application", Polymers, vol. 6, 2014, pp. 2985-3004.
Johanna Engstrand Unosson, et al., "An evaluation of methods to determine the porosity of calcium phosphate cements", Journal of Biomedical Materials Research Part B: Applied Biomaterials, vol. 103B, Issue 1, Jan. 2015, pp. 62-71.
Haiqing Hua, et al., "iPSC-derived β cells model diabetes due to glucokinase deficiency", The Journal of Clinical Investigation, vol. 123, No. 7, Jul. 2013, pp. 3146-3153.

US 10,155,069 B2

BONE GRAFT WITH A TANNIN-HYDROXYAPATITE SCAFFOLD AND STEM CELLS FOR BONE ENGINEERING

BACKGROUND OF THE INVENTION

Technical Field

The present invention relates to a bone graft comprising a tannin-hydroxyapatite resin scaffold, osteocompetent stem cells, and a growth medium, and methods of use.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Tannin and its derivatives can be used in various applications [U.S. Pat. No. 9,302,413; WO2014117946 A1; Lacoste, C., et al., Pine tannin-based rigid foams: Mechanical and thermal properties, *Industrial Crops and Products*, 2013, 43, 245; WO2013010668 A1; US20150361240; US20150274921; US20150259460; U.S. Pat. No. 6,043,350; US20140193322; US20140158927; US20060194918; Szczurek, A., et al., The use of tannin to prepare carbon gels. Parts I: Carbon aerogels, *Carbon*, 2011, 49, 2773; Szczurek, A., et al., The use of tannin to prepare carbon gels. Parts II: Carbon aerogels, *Carbon*, 2011, 49, 2785; Amaral-Labat, G., et al., Pore structure and electrochemical performances of tannin-based carbon cryogels, *Biomass Bioenergy*, 2012, 39, 274; Grishechko, L. I., et al., New tannin-lignin aerogels, *Industrial Crops and Products*, 2013, 41, 347—each incorporated herein by reference in its entirety], because their mechanical properties can vary in a wide range, depending on their method of preparation. Among others materials, tannin and tannin compounds have been approved for human use and have been accepted as totally non-toxic and environmentally friendly by the European commission REACH program and European Food Safety Authority (EFSA) [Ajinomoto OmniChem, Impact of REACh on Ajinomoto OmniChem's Natural Specialties, http://www.natural-specialities.com/PDF/Applications/REACh%20 compliance%20OmniChem%20Natural%20Specialties% 20v3.0.pdf, 2009; European Food Safety Authority, Scientific Opinion on the safety and efficacy of tannic acid when used as feed flavouring for all animal species, *EFSA Journal*, 2014, 12, 3828—each incorporated herein by reference in its entirety]. Tannins can be very soft materials such as the organic resin used as a "formaldehyde-free cornstarch-tannin adhesive" [Moubarik, A., et al., Preparation and Mechanical Characterization of Particleboard made from Maritime Pine and Glued with Bio-Adhesives based on Cornstarch and Tannins, *Maderas Ciencia y Technologia*, 2010, 12, 189; Basso, M. C., et al., A New Approach to Environmentally Friendly Protein Plastics and Foams, *Bioresources*, 2015, 10, 8014—each incorporated herein by reference in its entirety], or very hard materials such as grinding discs [Lagel, M. C., et al., Cutting and grinding wheels for angle grinders with a bio-resin matrix solid grinding wheels, *Industrial Crops and Products*, 2015, 67, 264—incorporated herein by reference in its entirety] and automobile brake pads [Lagel, M. C., et al., Automotive brake pads made with a bio resin matrix, *Industrial Crops and Products*, 2015, 85, 372—incorporated herein by reference in its entirety].

The need for bone tissue substitutes for dental, craniofacial, and orthopedic reconstructions is rapidly increasing due to rapid global population growth and extension of life expectancy, with the number of elderly people (+65 years) estimated to be about 2 billion by 2050 [Clegg, A. et al., Frailty in elderly people, *The Lancet*, 2013, 381, 752—incorporated herein by reference in its entirety]. Available options to treat bone deficiencies are based on transplantation of bone grafts or implantation of alloplastic materials [Hing, K. A., Bone repair in the twenty-first century: biology, chemistry or engineering?, *Philos Trans A Math Phys Eng Sci.*, 2004, 362, 2821—incorporated herein by reference in its entirety], which can restore tissue integrity and functionality but fail to provide optimal therapeutic solutions in several clinical cases, such as in situations characterized by extensive tissue loss, poor bone quality, or otherwise compromised regenerative capacity [Oreffo, R. O., et al., Future potentials for using osteogenic stem cells and biomaterials in orthopedics, *Bone*, 1999, 25, 5S—incorporated herein by reference in its entirety]. Conversely, engineering bone substitutes by culturing osteocompetent cells onto compliant biomaterials offers the possibility to grow unlimited amounts of tissue products with enhanced regenerative potential and broader clinical use [de Peppo G. M., et al., Engineering bone tissue substitutes from human induced pluripotent stem cells, *Proc Natl Acad Sci USA*. 2013, 110, 8680—incorporated herein by reference in its entirety].

Interfacing osteocompotent stem cells onto porous tannin spray-dried powder (PTSDP) resin scaffolds holds the potential to enhance the healing properties of these materials. However, currently available PTSDP scaffolds lack macroporosity, a critical feature that allows cell infiltration, communication, and growth. Scaffold porosity can also facilitate bone ingrowth and remodeling, therefore maximizing the therapeutic potential of tissue-engineered products. Specifically in bone engineering, porosity is important for developing biomaterial scaffolds that mimic the architecture of the native bone tissue.

In view of the forgoing, one objective of the present disclosure is to provide a bone graft comprising a tannin-hydroxyapatite resin scaffold, osteocompetent stem cells, and a growth medium, and methods of use.

BRIEF SUMMARY OF THE INVENTION

According to a first aspect, the present disclosure relates to a biocompatible bone graft which includes a porous scaffold structure comprising a tannin-hydroxyapatite resin which has a 17-80 vol % porosity, a pore diameter of 40-300 µm, and a compressive strength of 0.15-1.90 MPa; a population of osteocompetent stem cells obtained from a mammalian donor; and a growth medium.

In one embodiment the tannin-hydroxyapatite resin of the biocompatible bone graft comprises 50-90 wt % tannin and 10-50 wt % hydroxyapatite.

In one embodiment the osteocompetent stem cells within the biocompatible bone graft are derived from a sample of bone marrow, periosteum, dermal fibroblasts, or adipose tissue.

In another embodiment at least 50% of the osteocompetent stem cells express CD13, CD29, CD44, CD90, or CD105.

In another related embodiment, the biocompatible bone graft also comprises a growth factor. In a related embodiment, that growth factor is β-glycerophosphate, dexamethasone, ascorbic acid, transforming growth factor β (TGF-$β_1$), fibroblast growth factor (FGF), active vitamin D, a bone morphogenic protein (BMP), and/or parathyroid hormone.

In another embodiment, osteoinductive biomolecules are adsorbed or chemically-linked on the surface of the porous scaffold structure.

In one embodiment the porous scaffold structure is made with an additional biodegradable polymer of poly lactic-co-glycolic acid, poly lactic acid, poly glycolic acid, polyanhydride, poly(ortho)ester, polyurethane, poly(butyric acid), poly(valeric acid), polycaprolactone, poly(lactide-co-caprolactone), or poly(trimethylene carbonate).

In one embodiment, the biocompatible bone graft also comprises a first portion of bone on one side of the porous scaffold structure, and a second portion on another side of the porous scaffold structure, where both portions of bone comprise a bone wound site in a patient.

In a related embodiment, the biocompatible bone graft in the bone wound site further comprises mineralized osseous tissue supported by the porous scaffold structure and connecting both portions of bone.

In another related embodiment, the patient is the mammalian donor of the stem cells.

In another related embodiment, the biocompatible bone graft also comprises a prosthesis.

In another related embodiment, the biocompatible bone graft also comprises a second biocompatible bone graft in the wound site and which has a different size, shape, and/or composition.

According to a second aspect, the present disclosure relates to a method of monitoring the growth of the osteocompetent stem cells in the biocompatible bone graft for up to 16 weeks by X-ray imaging, MRI, or ultrasonography.

In another embodiment of the method, the growth of the osteocompetent stem cells in the biocompatible bone graft is monitored up to 16 weeks by the expression level of one of the following osteogenic differentiation genes: RUNX2, COL1A1, ALPL, OPN, or PDGFRB.

According to a third aspect, the present disclosure relates to a method of screening a bone disease drug by adding the drug to the biocompatible bone graft, growing the osteocompetent stem cells in the presence of the drug to form new bone tissue on the bone graft, measuring the porosity, density, and/or compressive strength of the drug-treated bone graft, and comparing it to a substantially similar bone graft that has not been treated with the drug.

In one embodiment, the bone disease drug is denosumab, teriparatide, alendronate, risedronate, ibandronate, zoledronic acid, teriparatide, strontium ranelate, aluminium chlorohydrate, or odanacatib.

According to a fourth aspect, the present disclosure relates to a method of making a porous scaffold structure starting with mixing porous tannin powder particles, dried polyethylene glycol particles, and hydroxyapatite together to make a powder mixture; mixing the powder mixture with an organic acid and a formaldehyde solution to form a liquid mixture; incubating the liquid mixture to form a set scaffold; and heating the set scaffold to remove the polyethylene glycol particles to form the porous scaffold structure.

In another embodiment of the method, a biodegradable polymer is also added to the powder mixture. In a further embodiment, the biodegradable polymer is poly lactic-co-glycolic acid, poly lactic acid, poly glycolic acid, polyanhydride, poly(ortho)ester, polyurethane, poly(butyric acid), poly(valeric acid), polycaprolactone, poly(lactide-co-caprolactone), or poly(trimethylene carbonate).

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

FIG. IJ is an SEM image of a decellularized bone scaffold.

Figure 2:
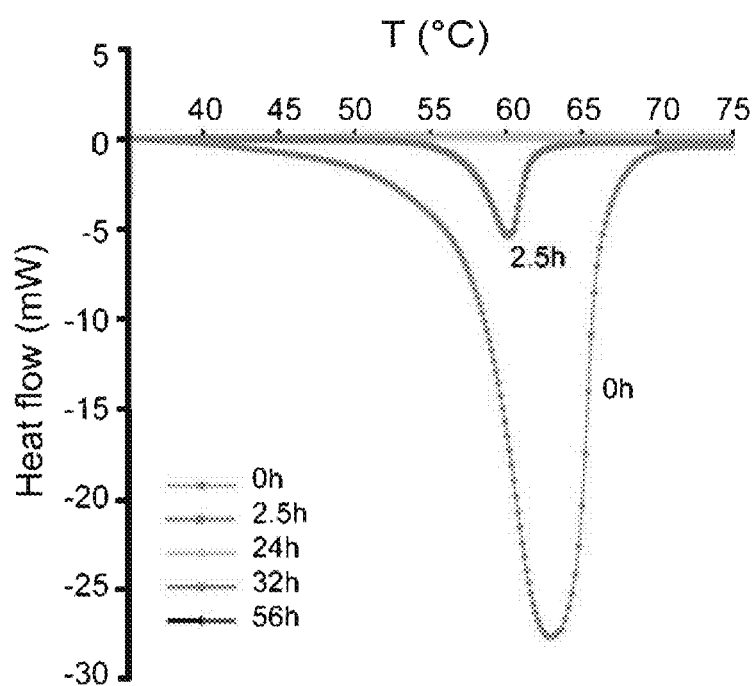

FIG. 2 is a differential scanning calorimetry (DSC) graph of a tannin-hydroxyapatite resin scaffold showing the removal of polyethylene glycol (PEG) throughout the leaching process.

Figure 3:
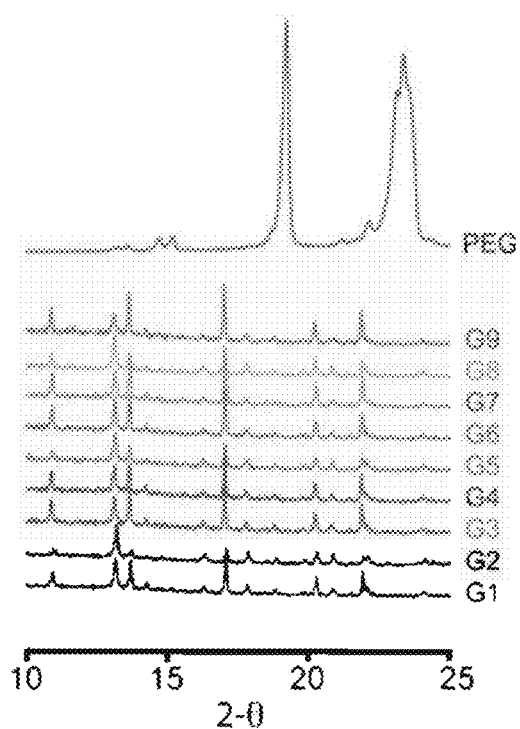

FIG. 3 is an X-ray diffraction (XRD) profile of all tannin-hydroxyapatite resin scaffold groups showing the absence of the peak corresponding to PEG after 24 hours of leaching.

Figure 4A:
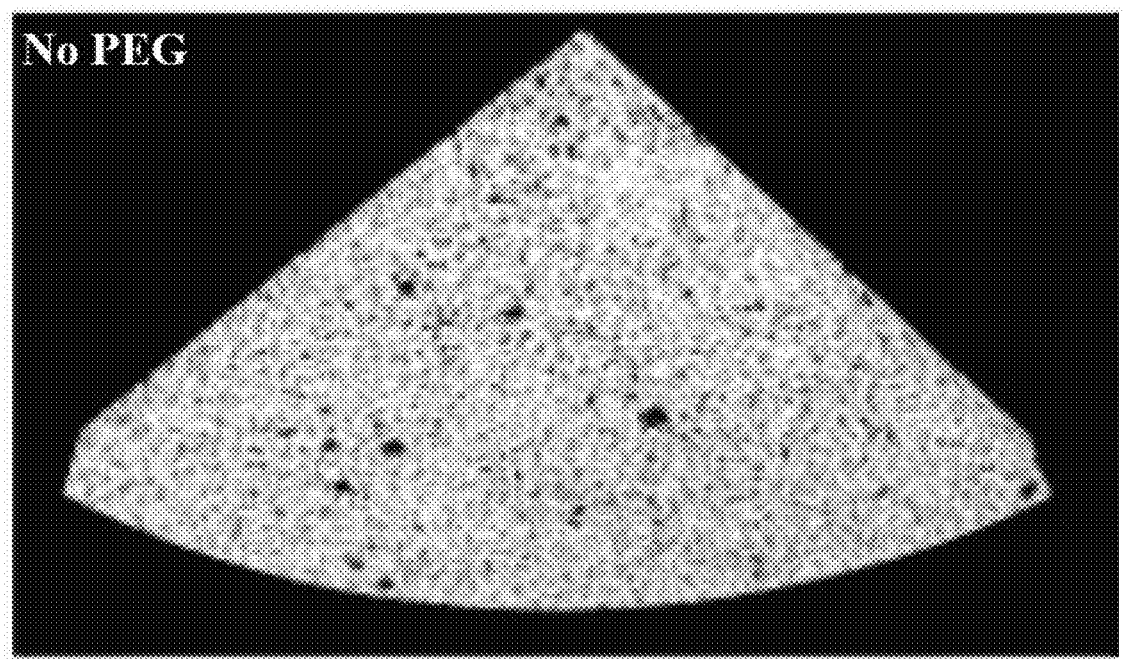

FIG. 4A is a micro-CT image of a reference scaffold structure made without PEG.

Figure 4B:
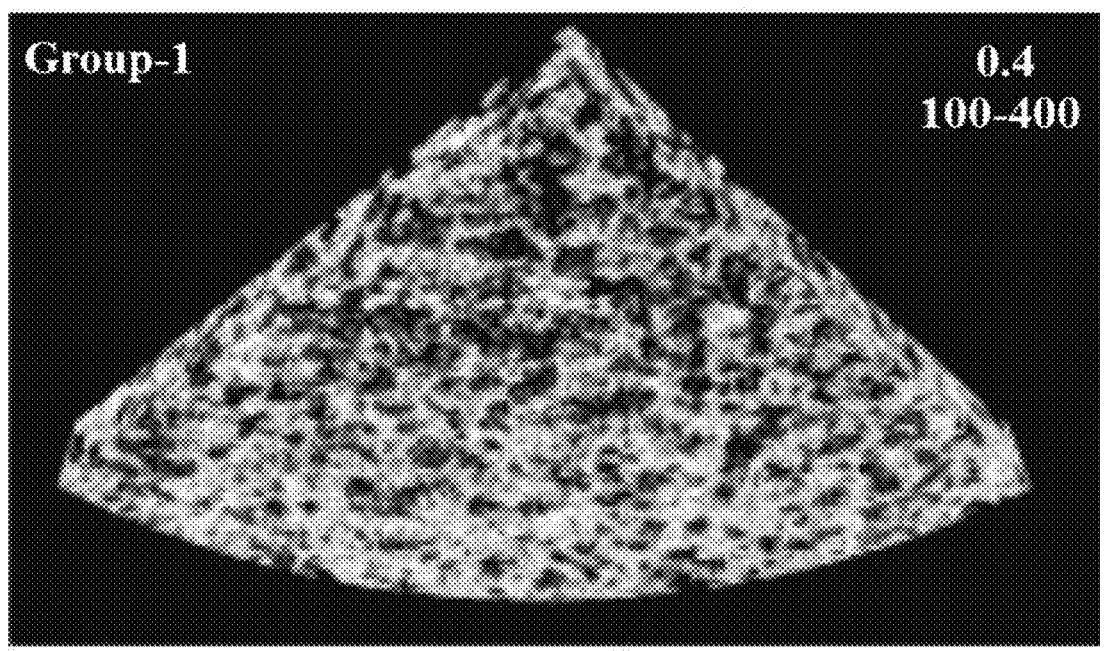

FIG. 4B is a micro-CT image of a Group 1 scaffold made with a 0.4 weight ratio of PEG:cement (tannin and hydroxyapatite) using 100-400 μm diameter PEG particles.

Figure 4C:
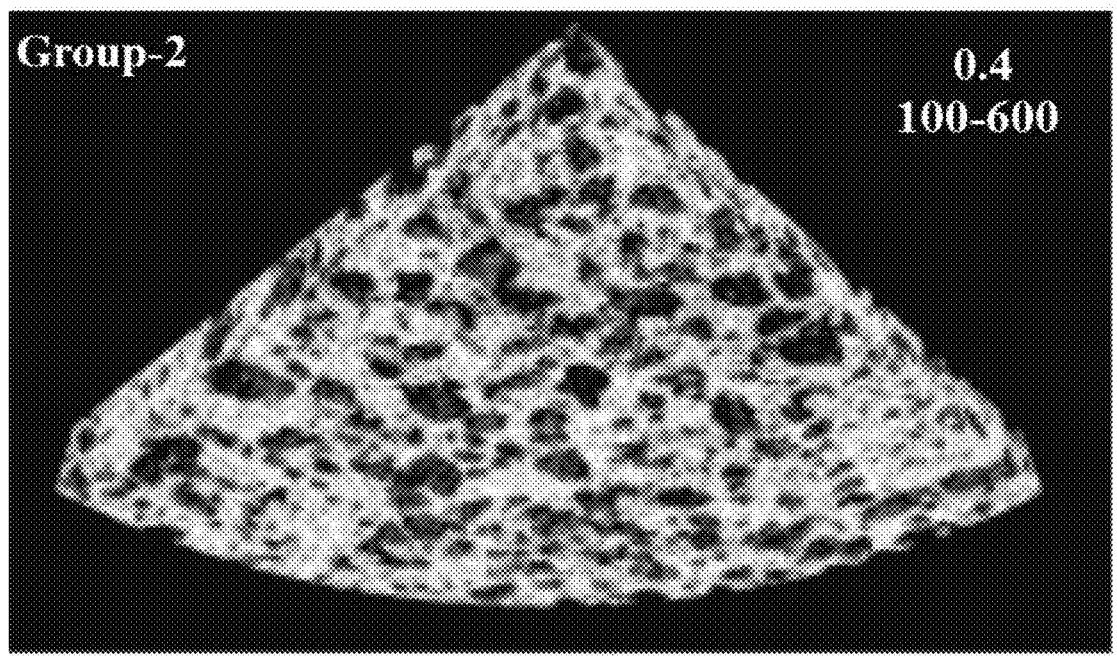

FIG. 4C is a micro-CT image of a Group 2 scaffold made with a 0.4 weight ratio of PEG using 100-600 μm diameter PEG particles.

Figure 4D:
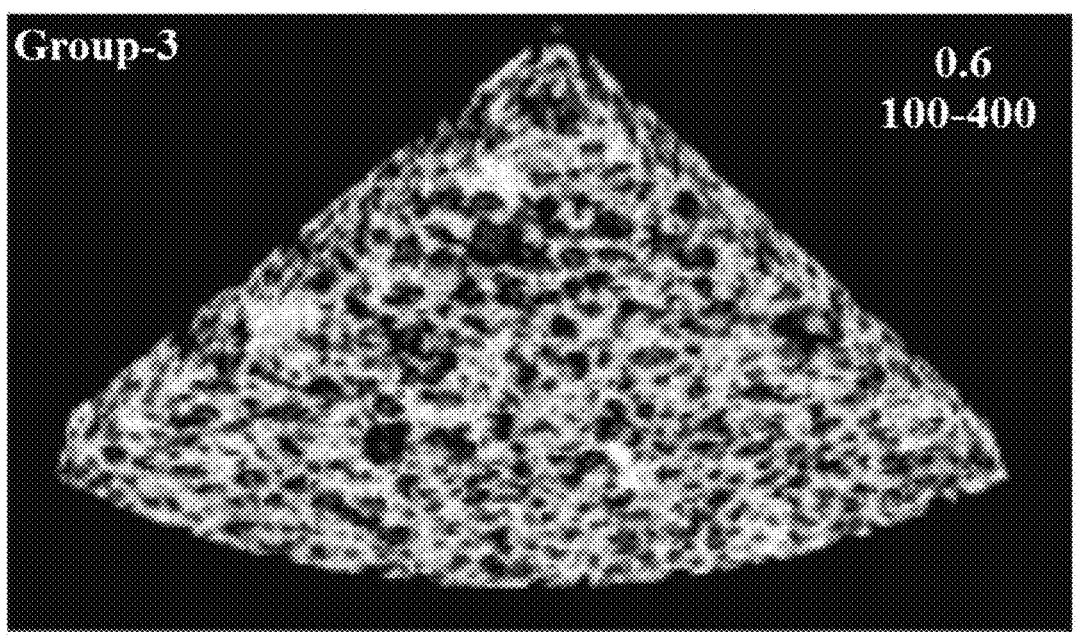

FIG. 4D is a micro-CT image of a Group 3 scaffold made with a 0.6 weight ratio of PEG using 100-400 μm diameter PEG particles.

Figure 4E:
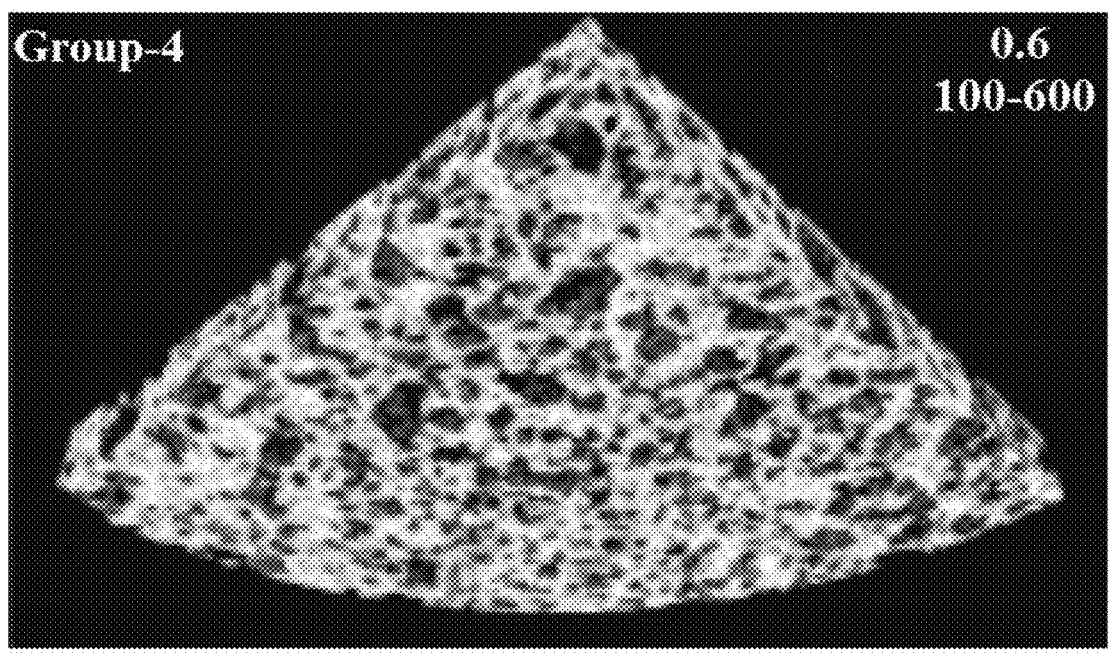

FIG. 4E is a micro-CT image of a Group 4 scaffold made with a 0.6 weight ratio of PEG using 100-600 μm diameter PEG particles.

Figure 4F:
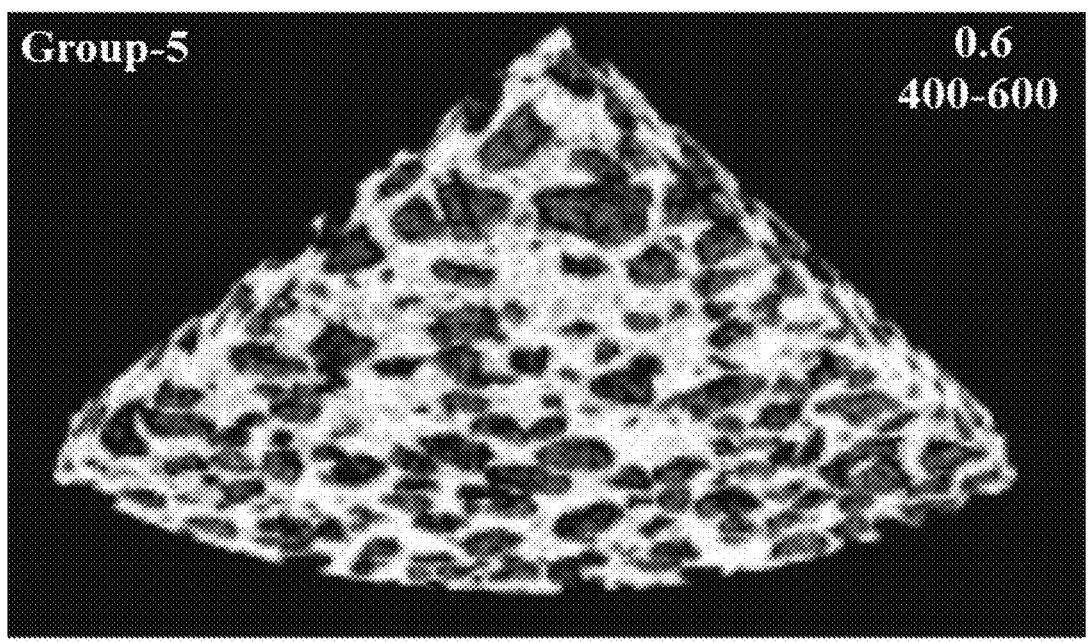

FIG. 4F is a micro-CT image of a Group 5 scaffold made with a 0.6 weight ratio of PEG using 400-600 μm diameter PEG particles.

Figure 4G:
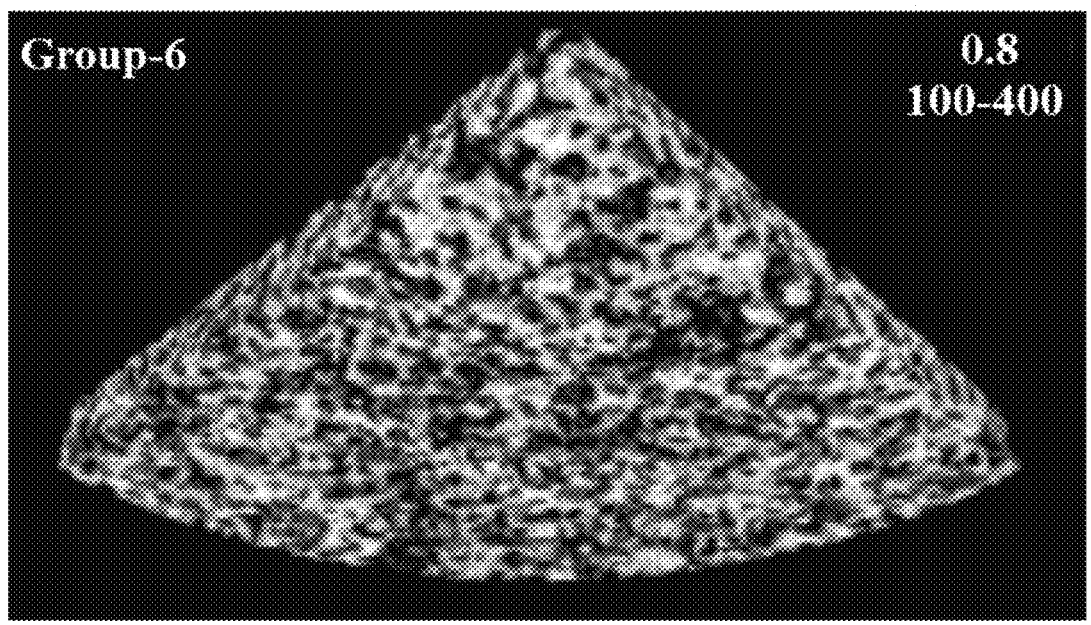

FIG. 4G is a micro-CT image of a Group 6 scaffold made with a 0.8 weight ratio of PEG using 100-400 μm diameter PEG particles.

Figure 4H:
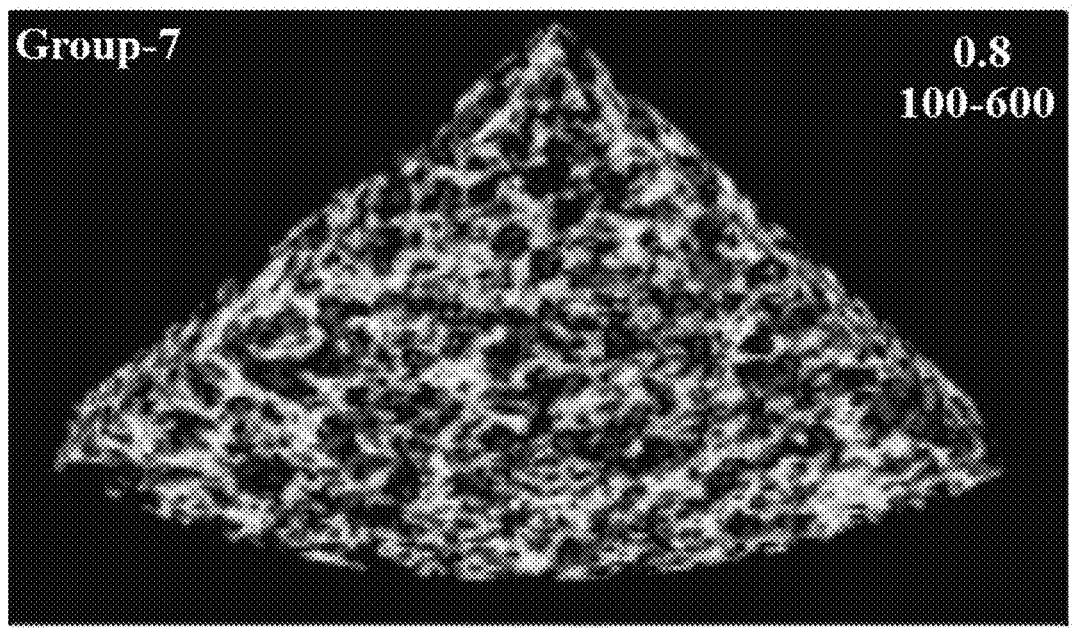

FIG. 4H is a micro-CT image of a Group 7 scaffold made with a 0.8 weight ratio of PEG using 100-600 μm diameter PEG particles.

Figure 4I:
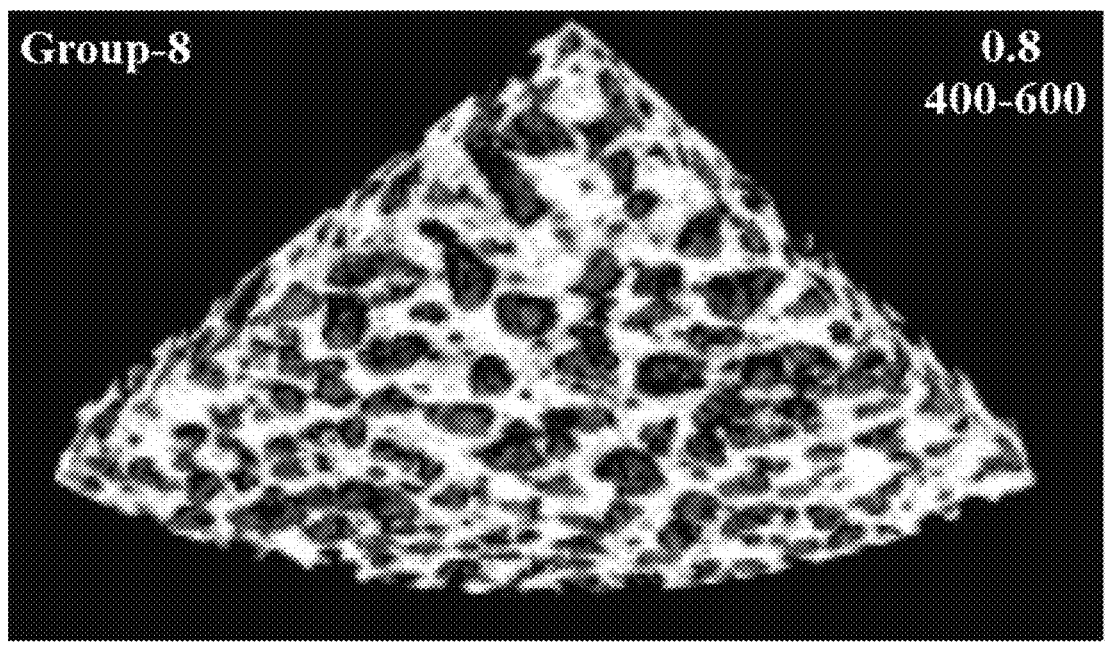

FIG. 4I is a micro-CT image of a Group 8 scaffold made with a 0.8 weight ratio of PEG using 400-600 μm diameter PEG particles.

Figure 4J:
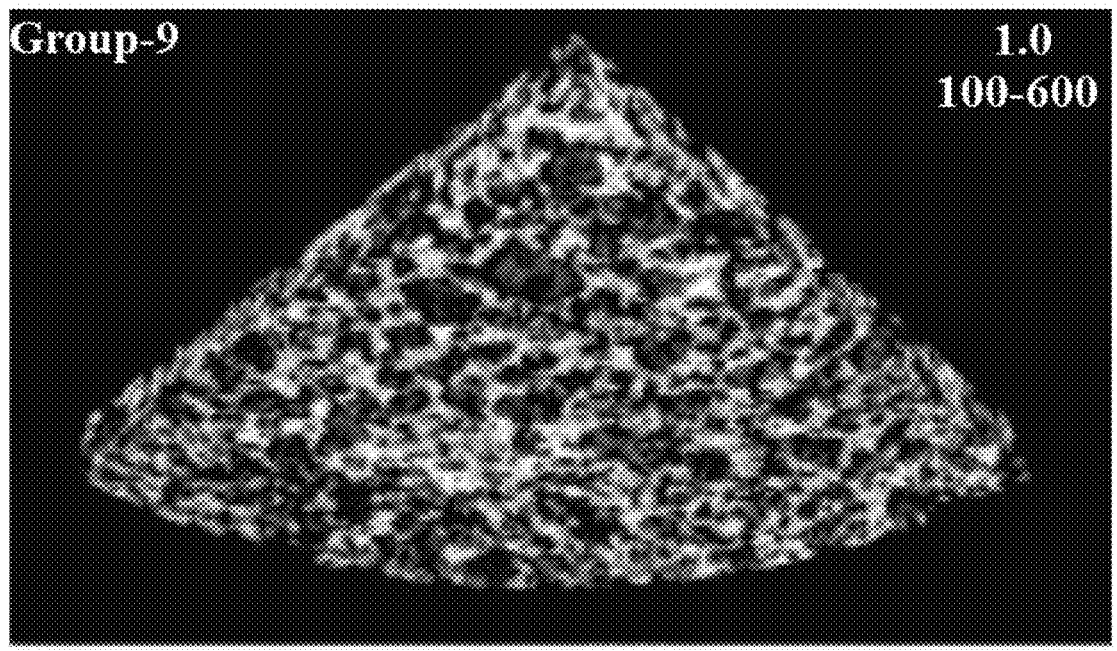

FIG. 4J is a micro-CT image of a Group 9 scaffold made with a 1.0 weight ratio of PEG using 100-600 μm diameter PEG particles.

Figure 4K:
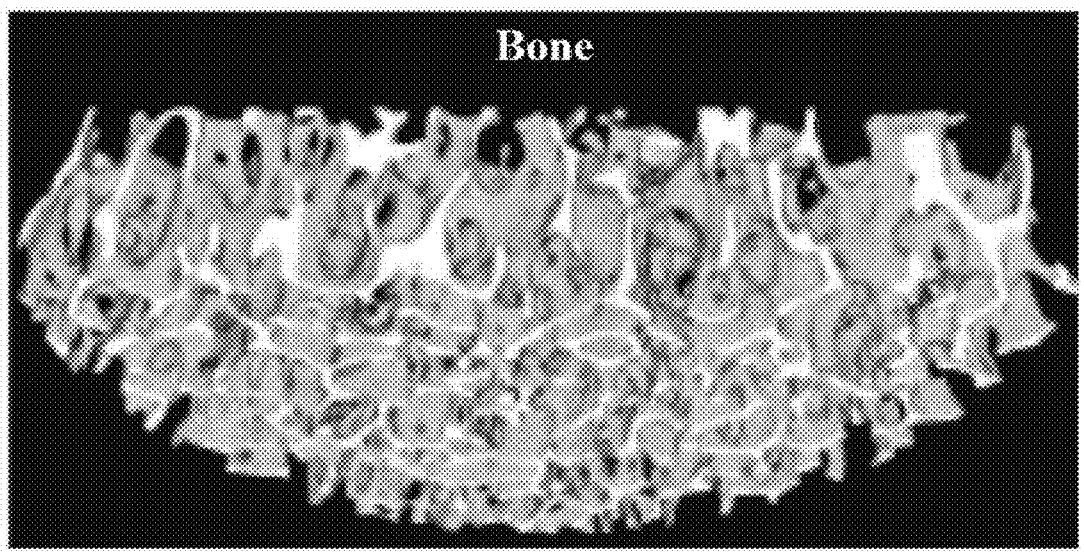

FIG. 4K is a micro-CT image of a decellularized bone scaffold.

Figure 5:
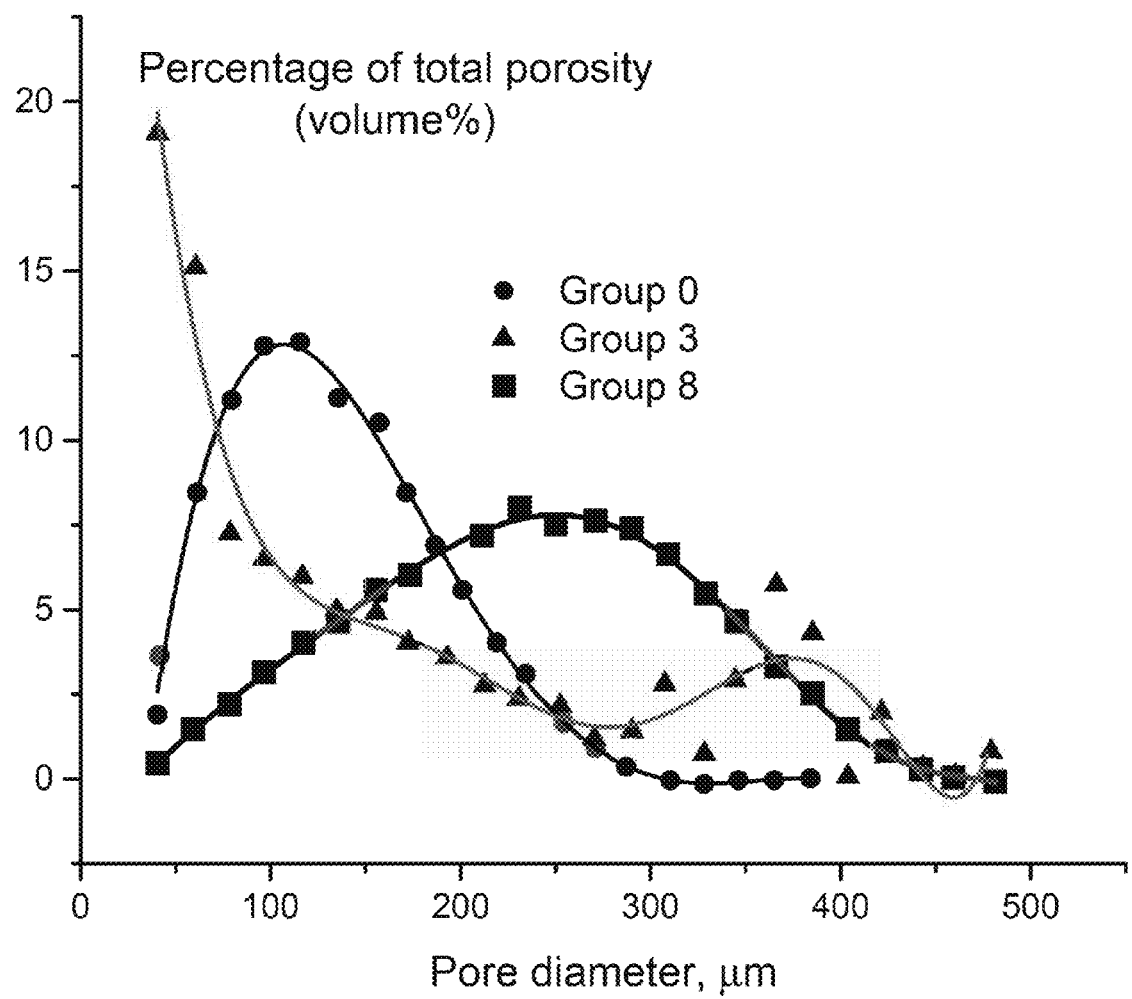

FIG. 5 is the pore size distribution of three different tannin-hydroxyapatite resin scaffolds.

Figure 6:
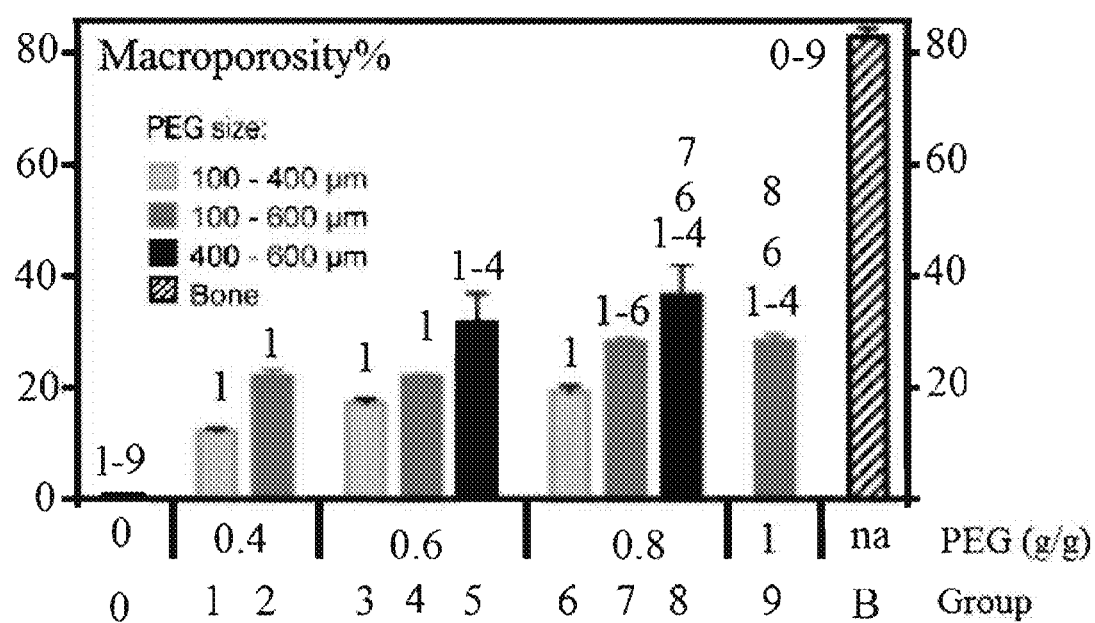

FIG. 6 is the macroporosity, or porosity, of the resin scaffolds and decellularized bone as measured by micro-CT.

Figure 7:
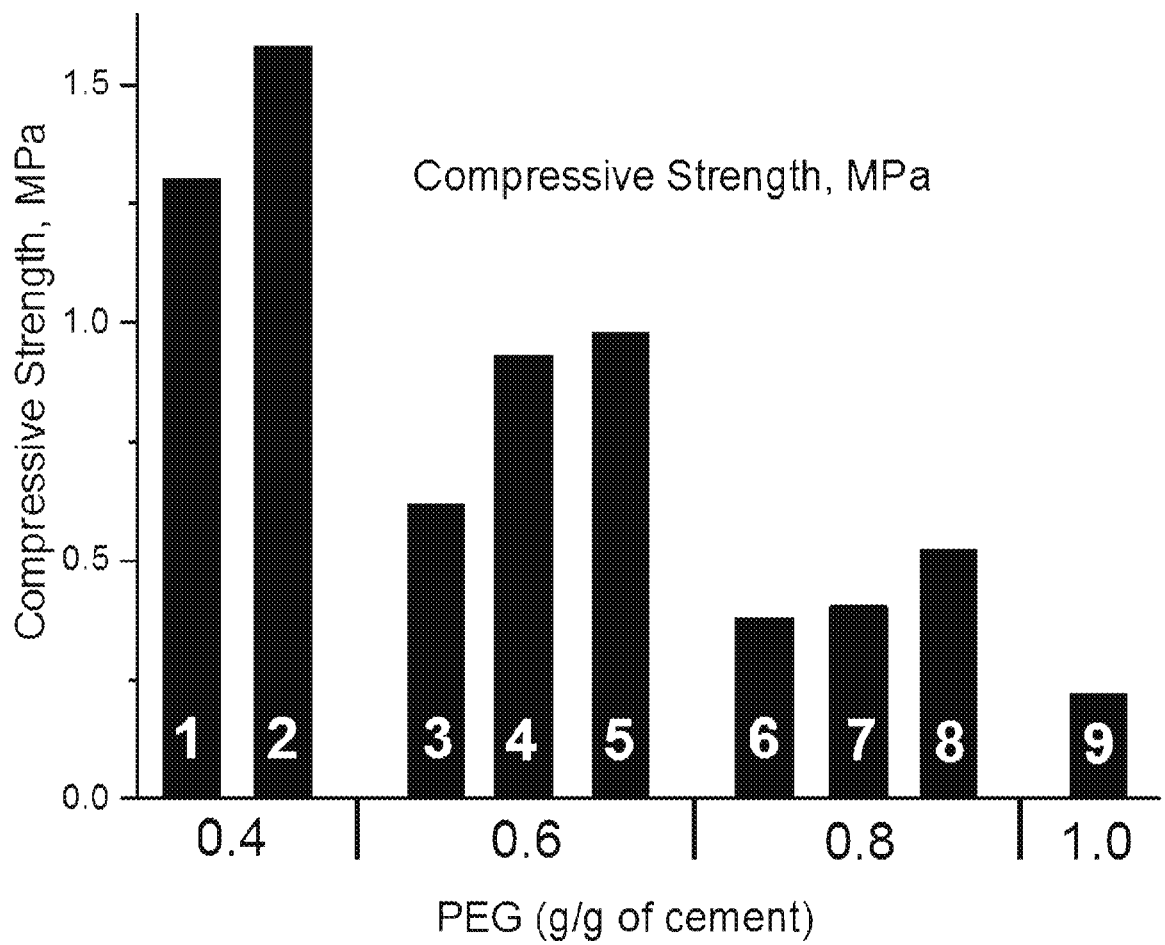

FIG. 7 is a graph showing the compressive strength of the resin scaffolds.

Figure 8:
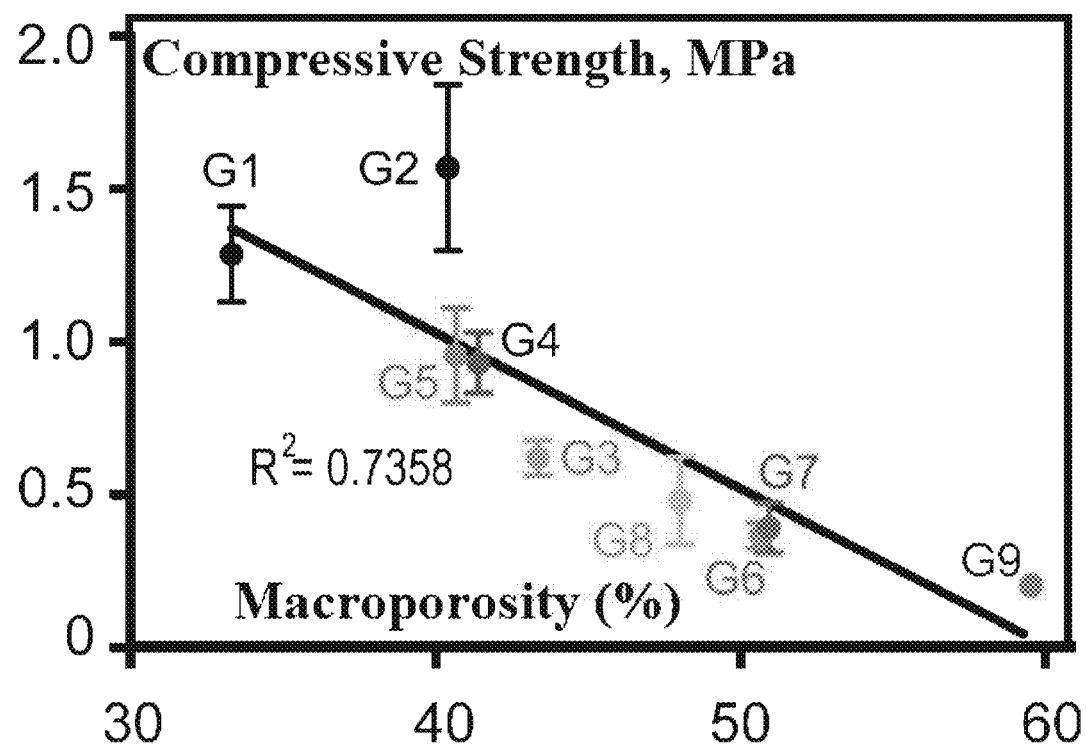

FIG. 8 is a linear regression analysis between the porosity and compressive strength of the resin scaffolds.

Figure 9A:
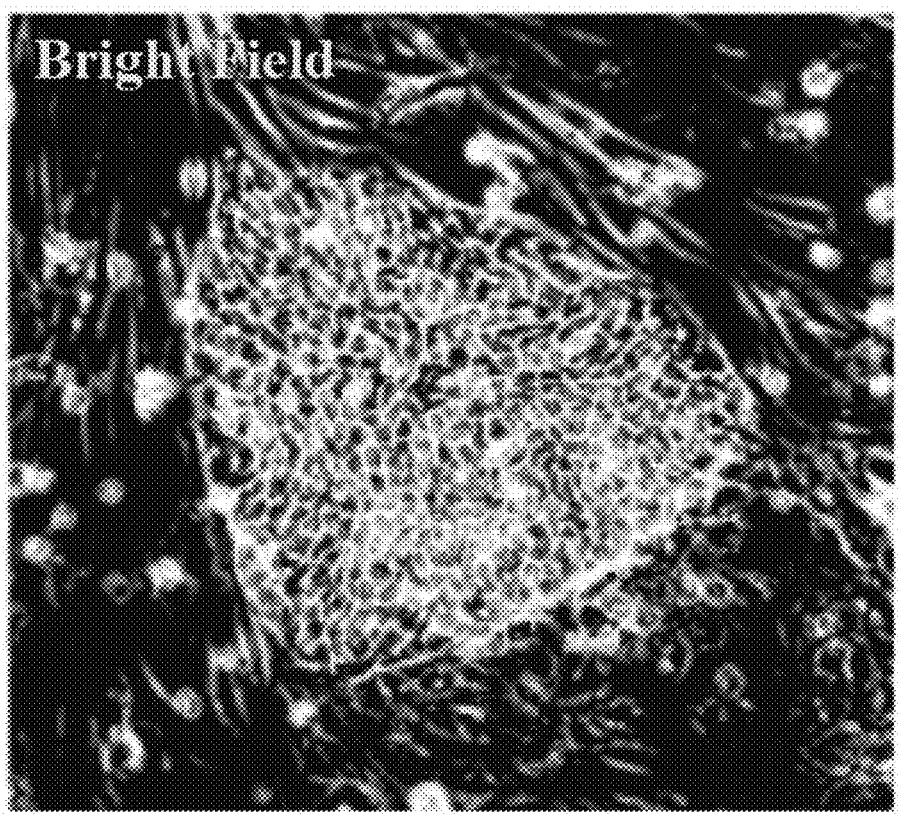

FIG. 9A is a bright field view of a cluster of undifferentiated 1013A human induced pluripotent stem cells showing typical iPSC morphology.

Figure 9B:
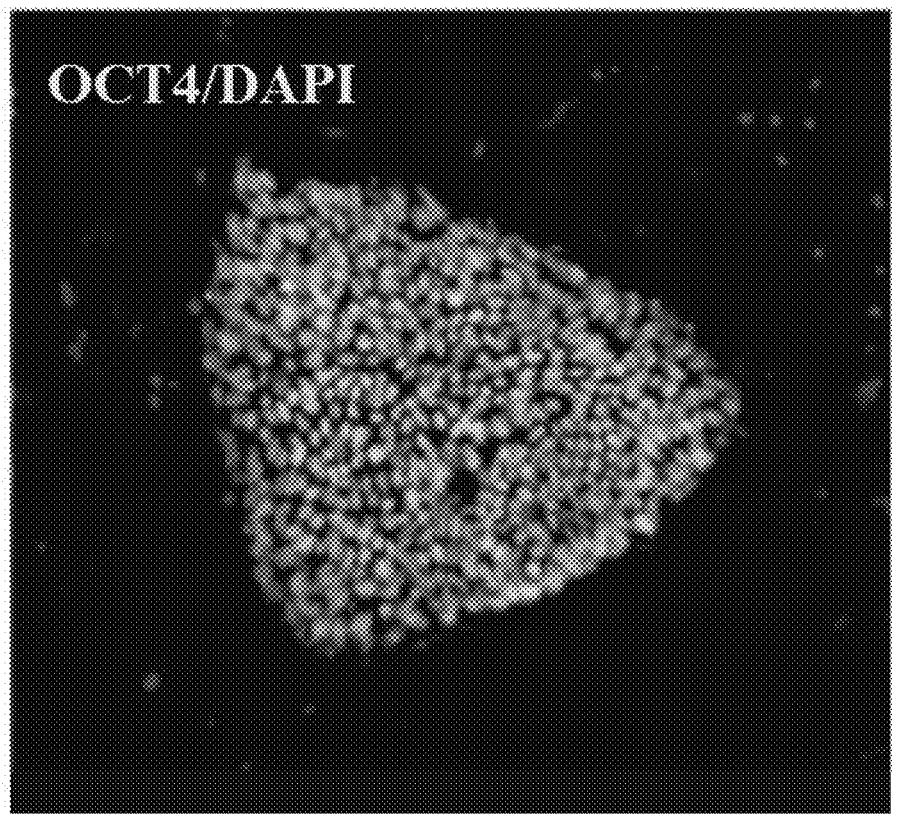

FIG. 9B is the same view of the cells in FIG. 9A but showing OCT4 immunofluorescence and DAPI staining.

Figure 9C:
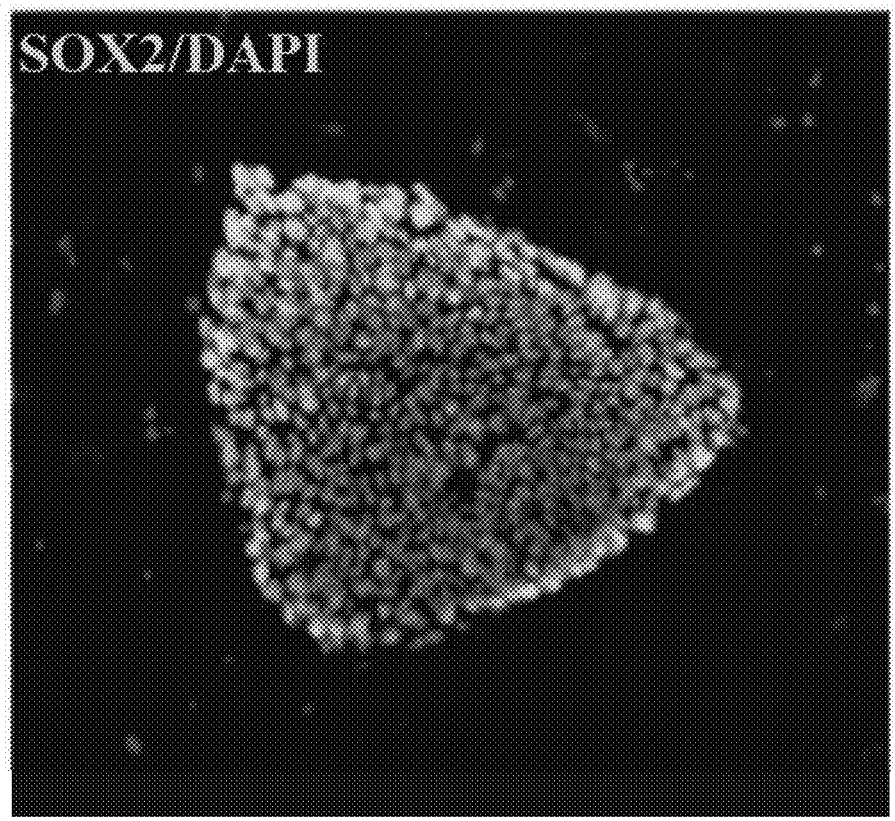

FIG. 9C is the same view of the cells in FIG. 9A but showing SOX2 immunofluorescence and DAPI staining.

Figure 9D:
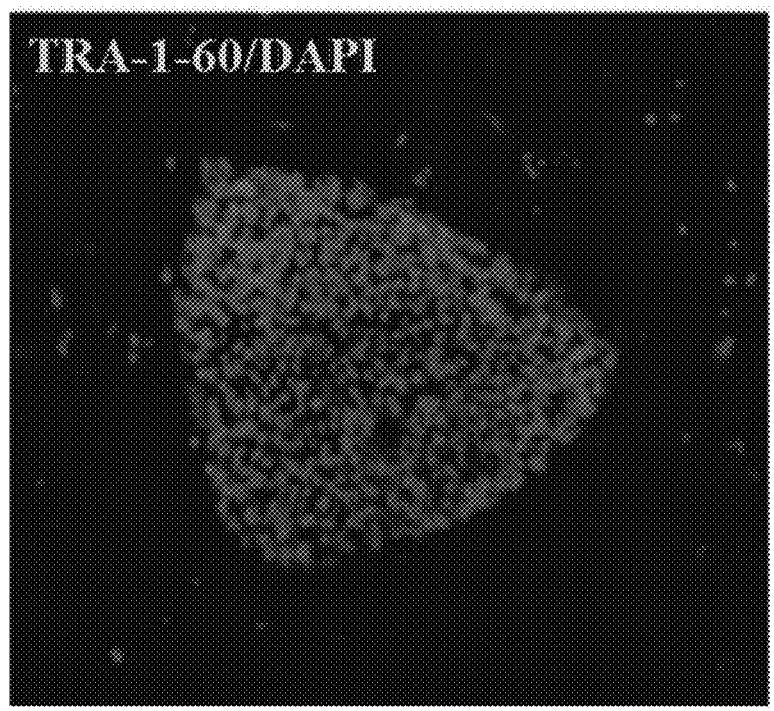

FIG. 9D is the same view of the cells in FIG. 9A but showing TRA-1-60 immunofluorescence and DAPI staining.

Figure 10A:
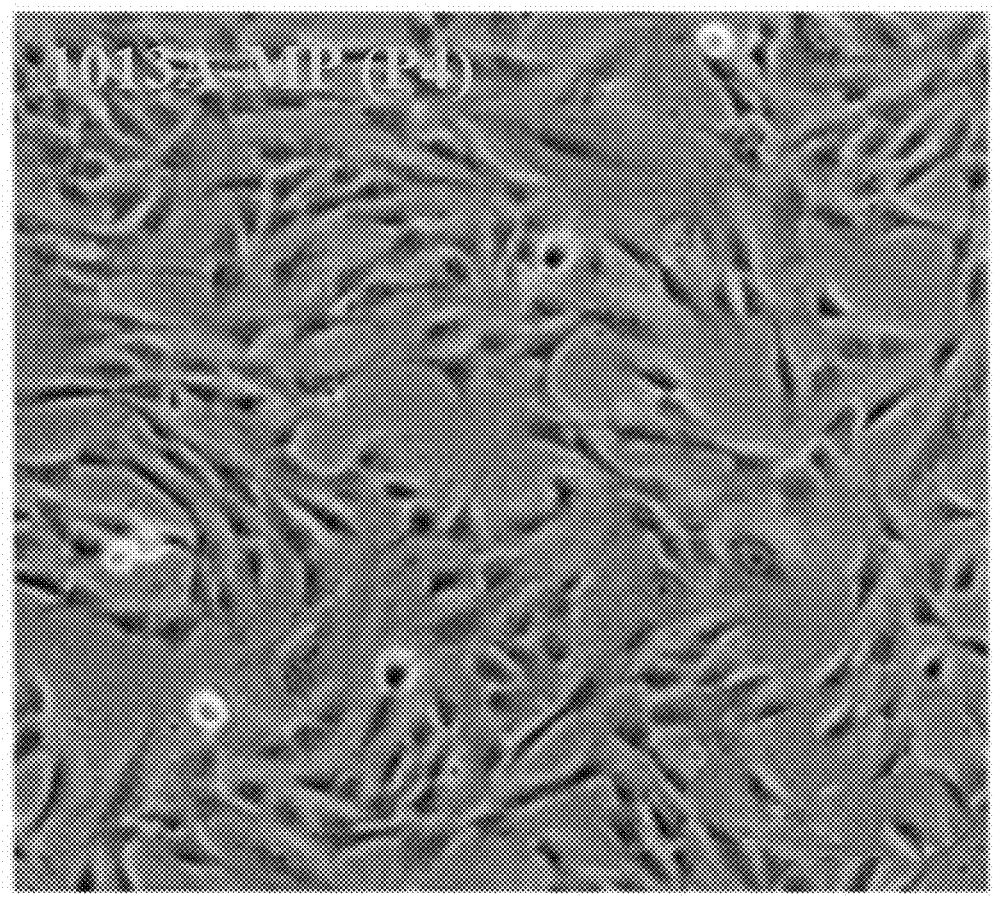

FIG. 10A is a bright field view of 1013A-derived mesenchymal progenitors (1013A-MP) at passage 4 showing a fibroblast-like morphology.

Figure 10B:
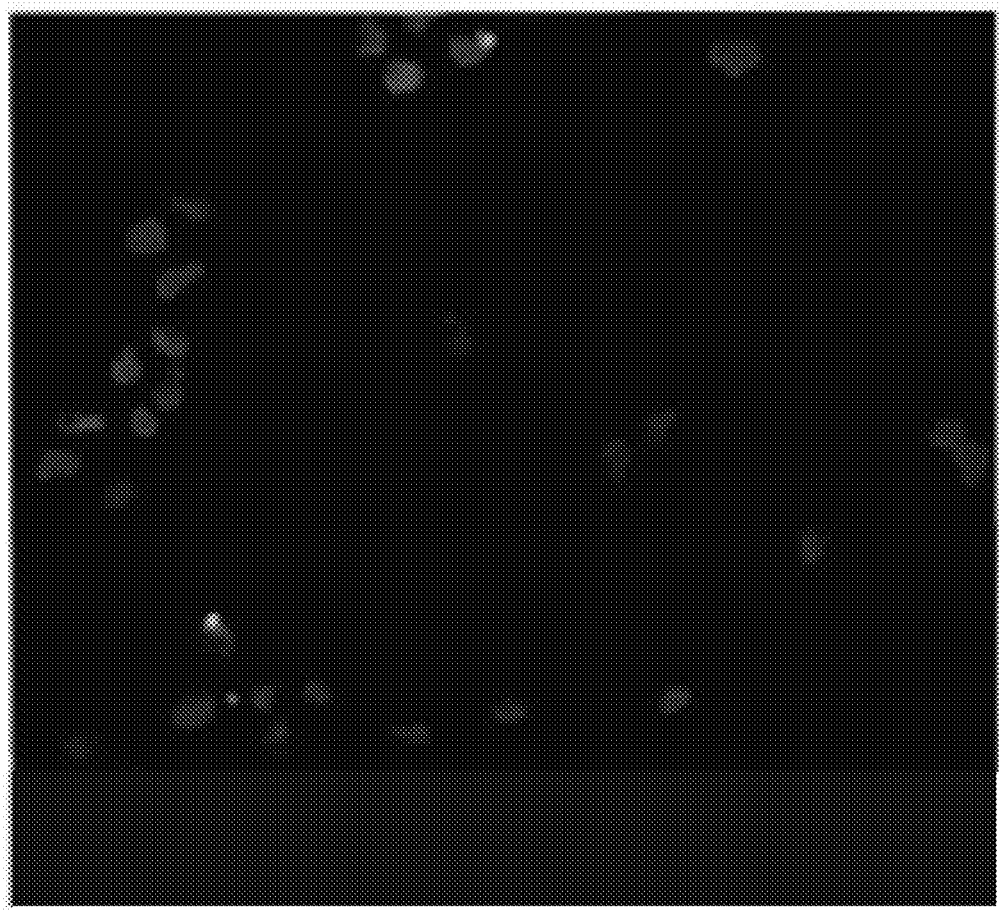

FIG. 10B shows the same view of cells in FIG. 10A but with OCT4 immunofluorescence and DAPI staining.

Figure 10C:
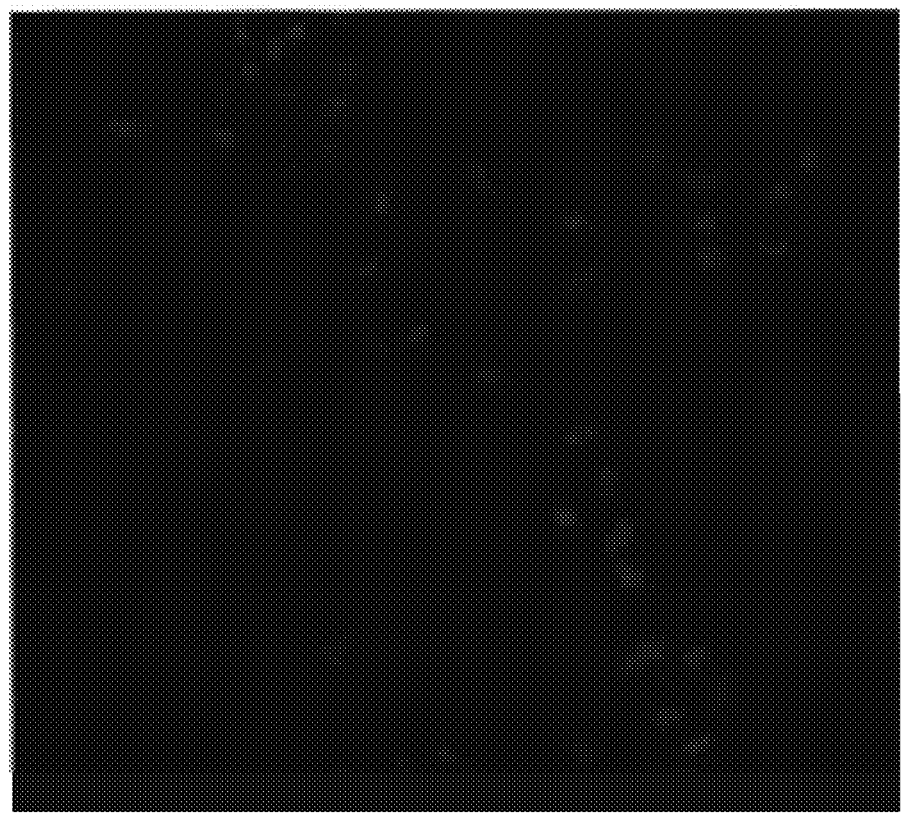

FIG. 10C shows the same view of cells in FIG. 10A but with SOX2 immunofluorescence and DAPI staining.

Figure 10D:
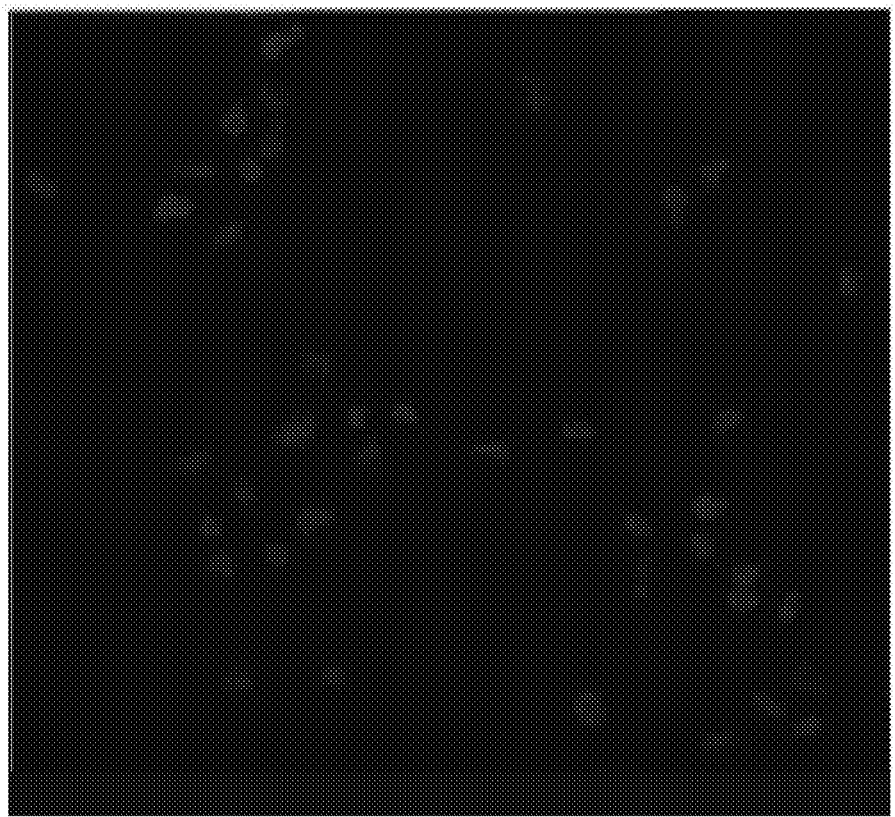

FIG. 10D shows the same view of cells in FIG. 10A but with TRA-1-60 immunofluorescence and DAPI staining.

Figure 11A:
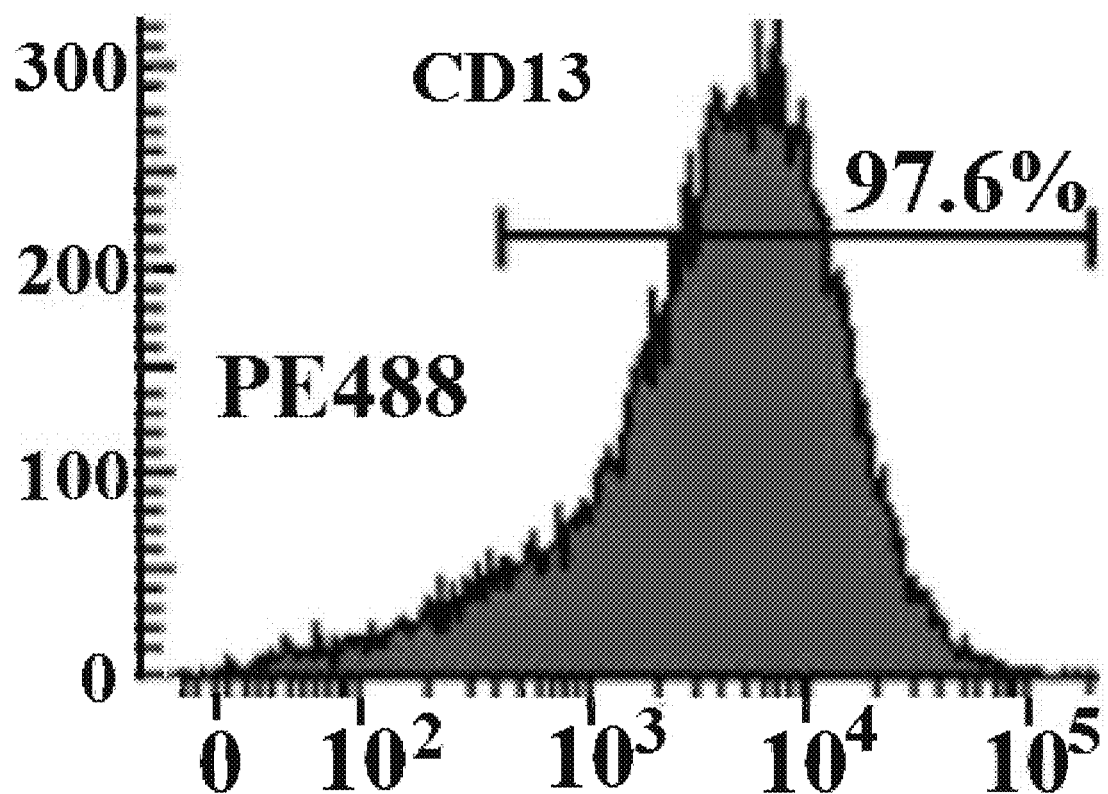

FIG. 11A shows the 1013A-MP surface antigen profile of CD13 measured by flow cytometry.

Figure 11B:
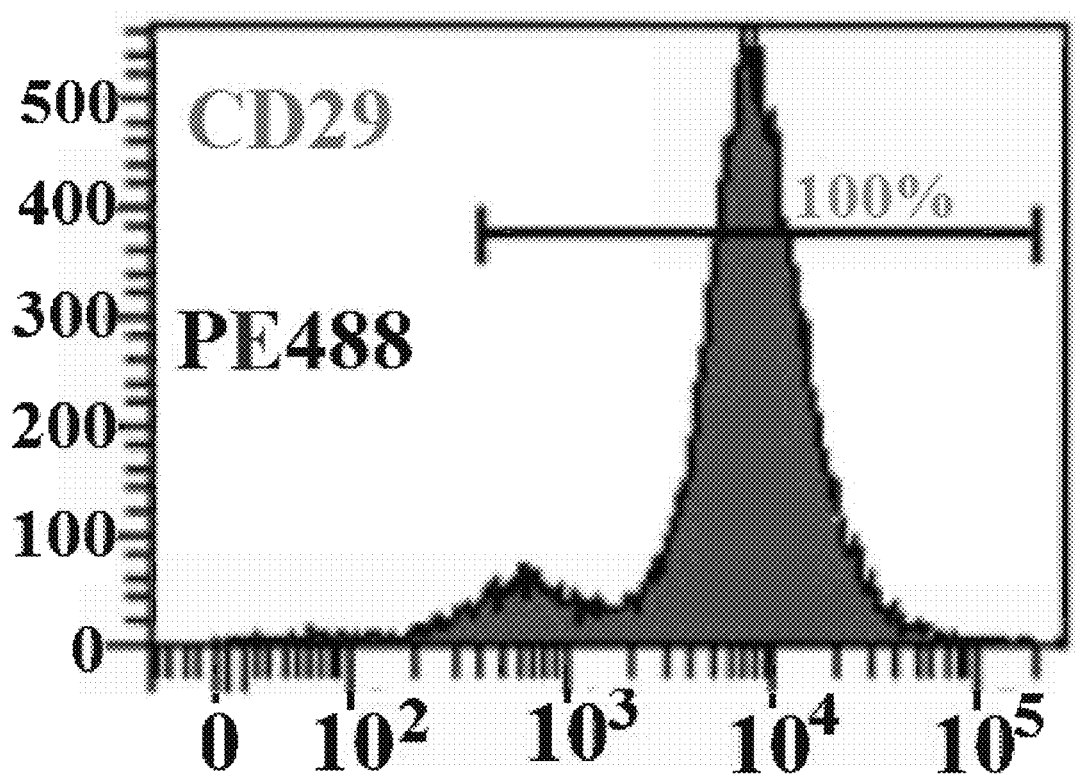

FIG. 11B shows the 1013A-MP surface antigen profile of CD29 measured by flow cytometry.

Figure 11C:
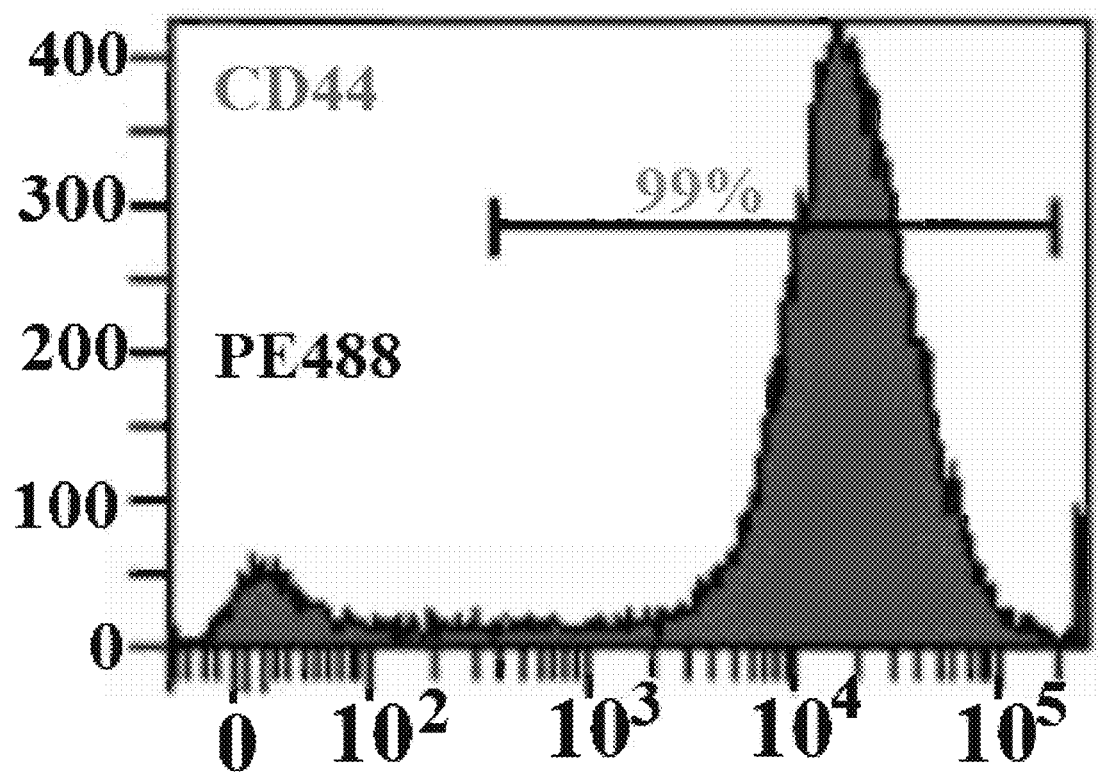

FIG. 11C shows the 1013A-MP surface antigen profile of CD44 measured by flow cytometry.

Figure 11D:
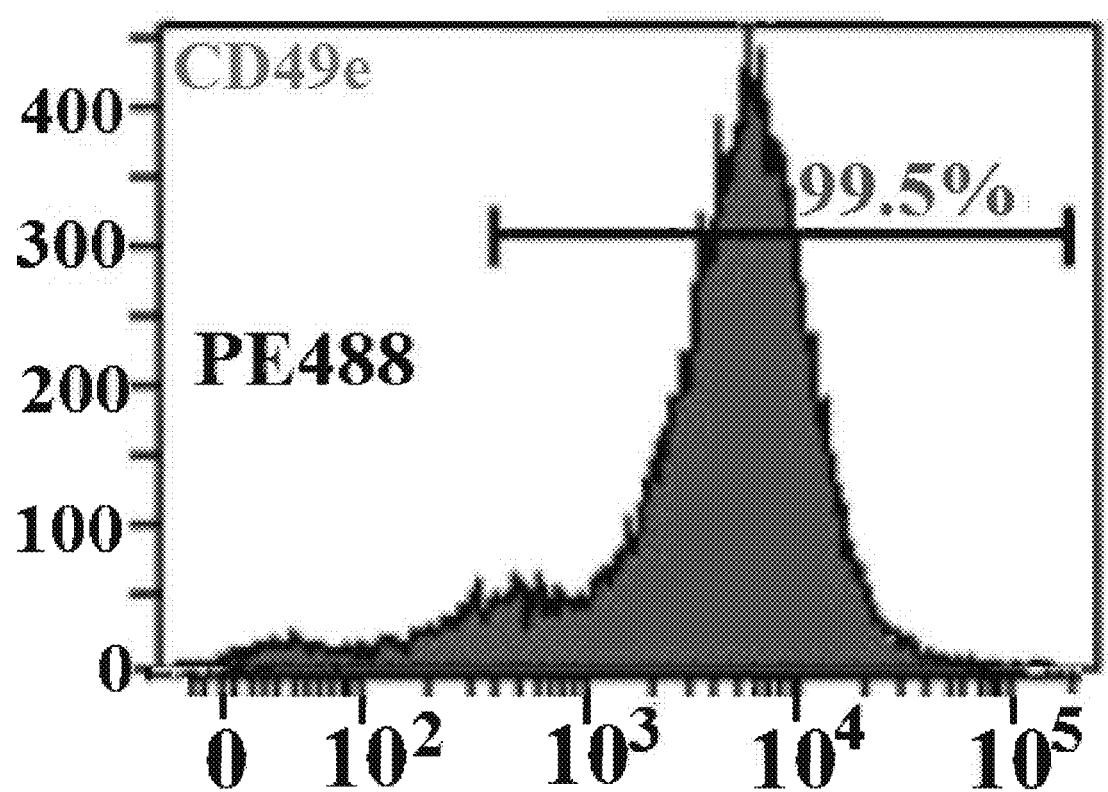

FIG. 11D shows the 1013A-MP surface antigen profile of CD49e measured by flow cytometry.

Figure 11E:
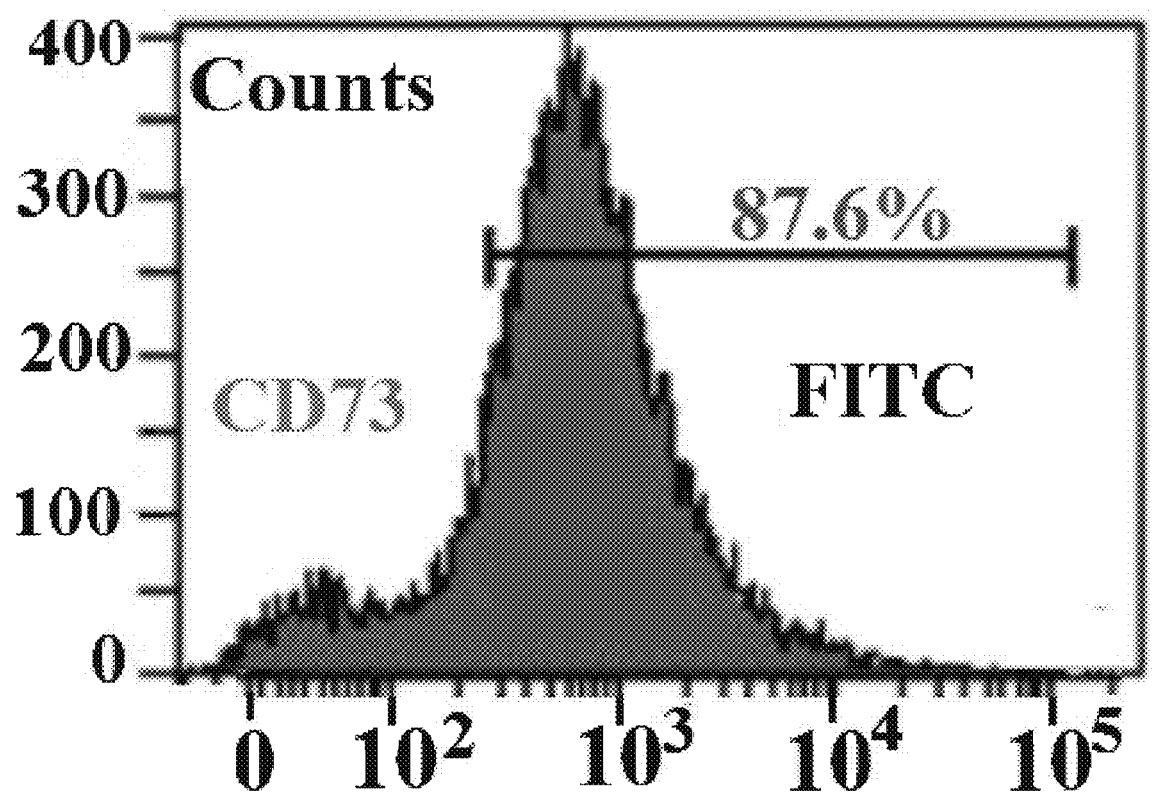

FIG. 11E shows the 1013A-MP surface antigen profile of CD73 measured by flow cytometry.

Figure 11F:
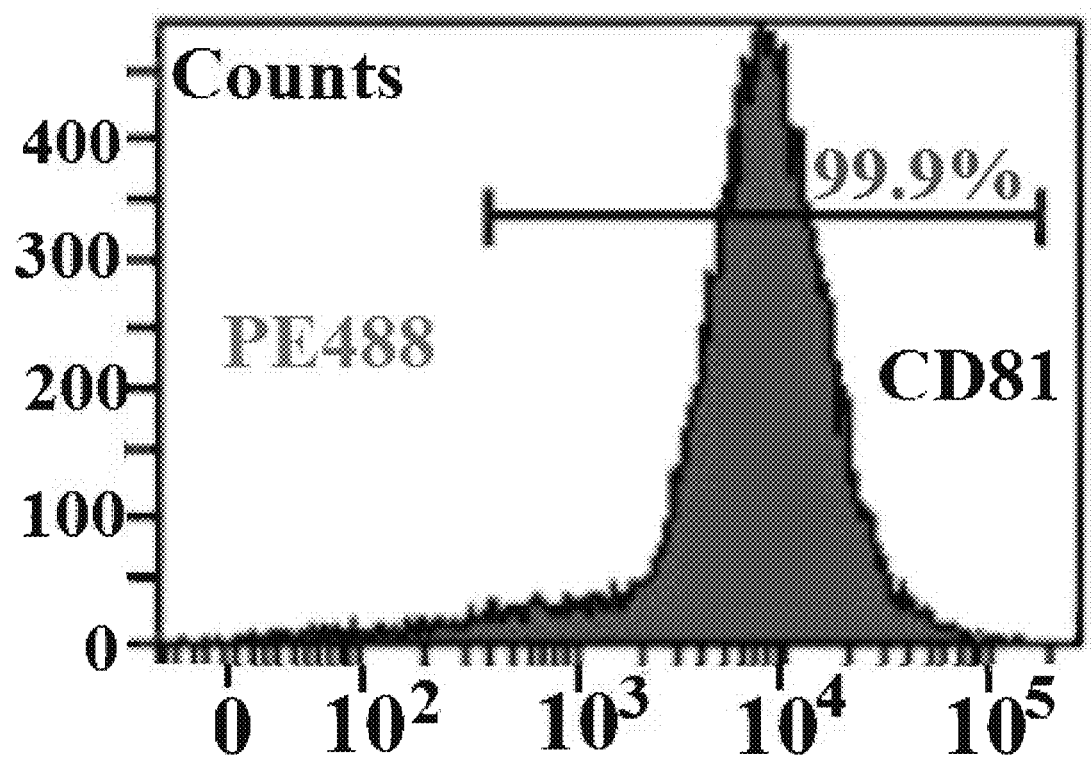

FIG. 11F shows the 1013A-MP surface antigen profile of CD81 measured by flow cytometry.

Figure 11G:
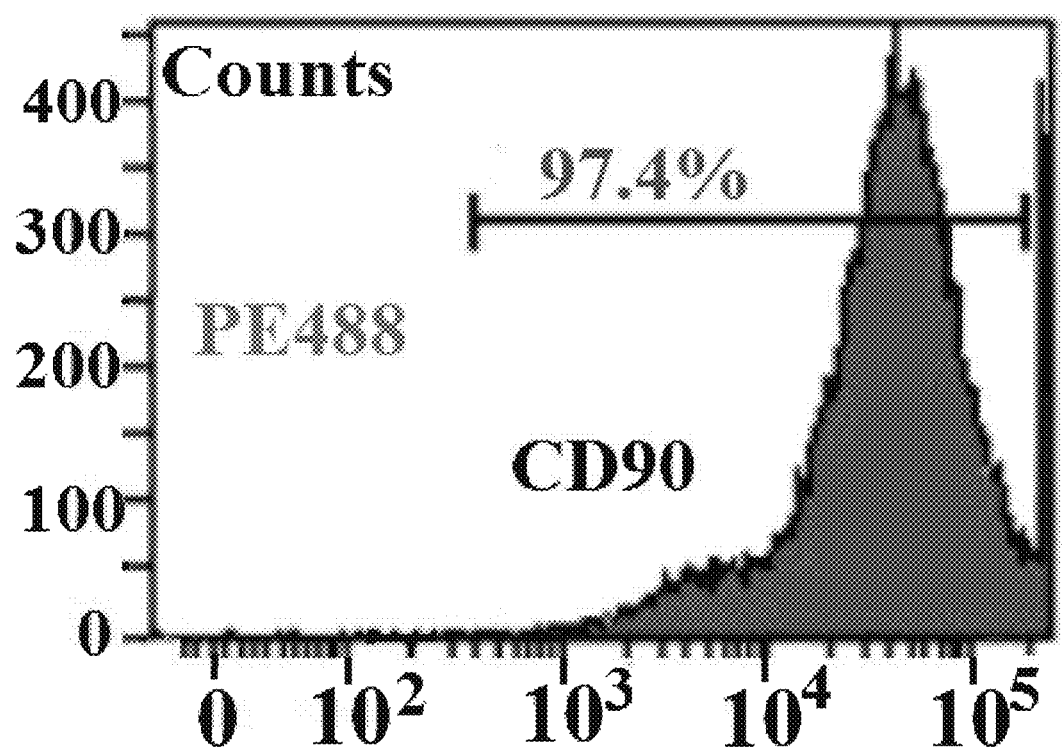

FIG. 11G shows the 1013A-MP surface antigen profile of CD90 measured by flow cytometry.

Figure 11H:
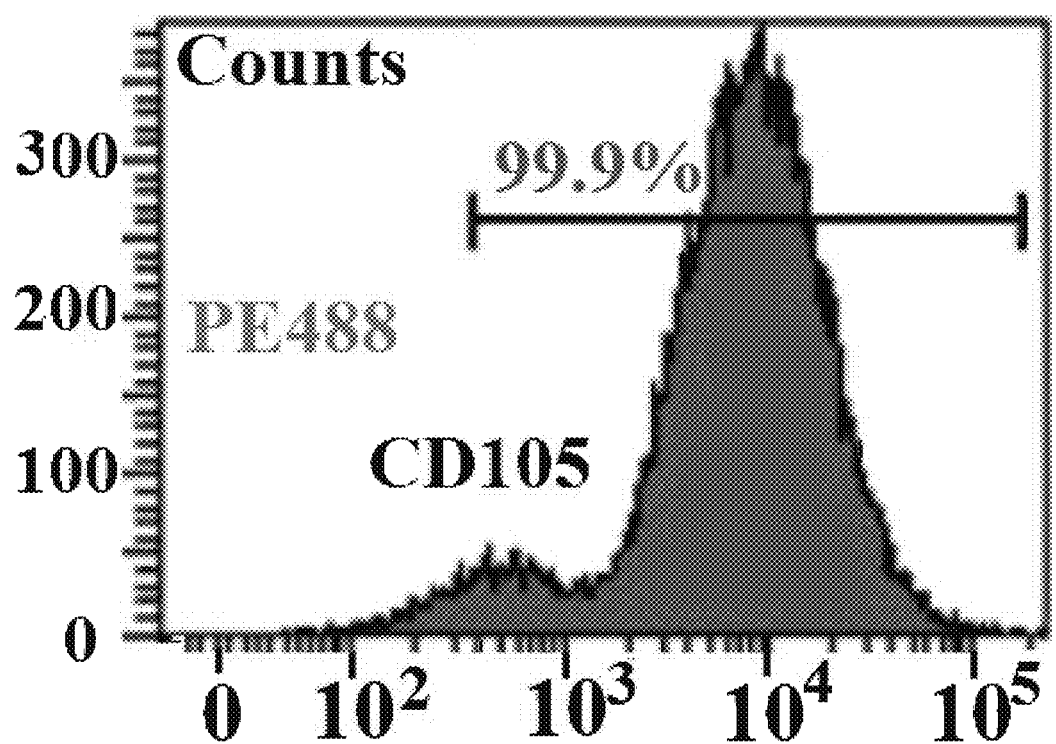

FIG. 11H shows the 1013A-MP surface antigen profile of CD105 measured by flow cytometry.

Figure 11I:
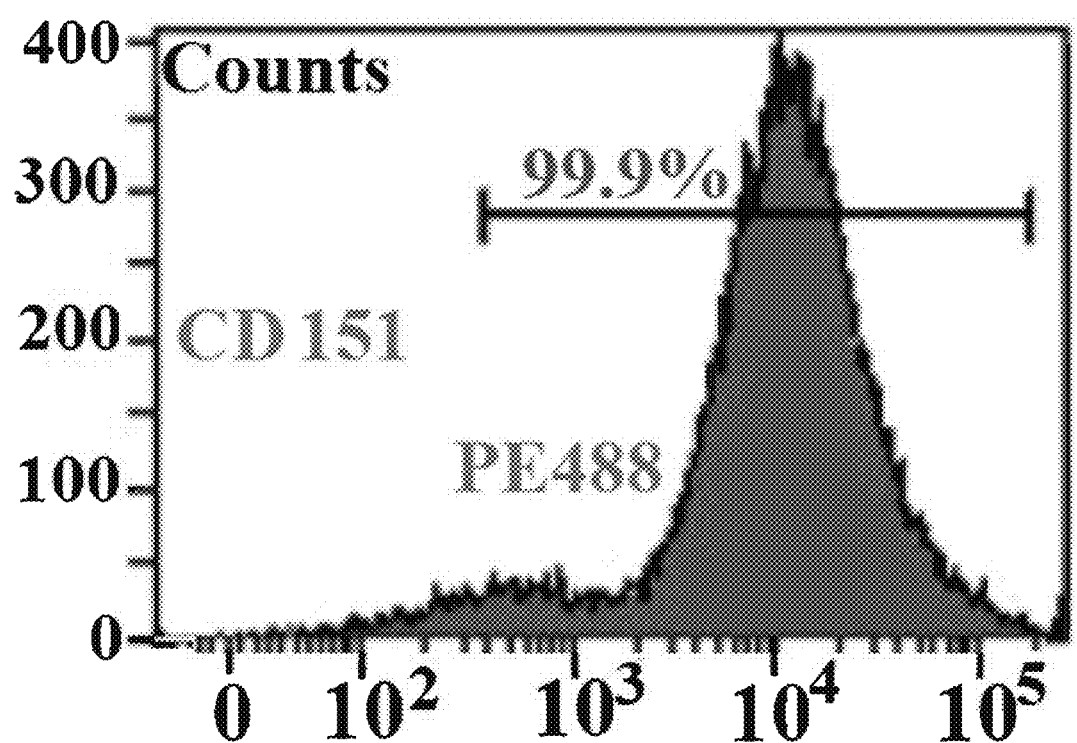

FIG. 11I shows the 1013A-MP surface antigen profile of CD151 measured by flow cytometry.

Figure 11J:
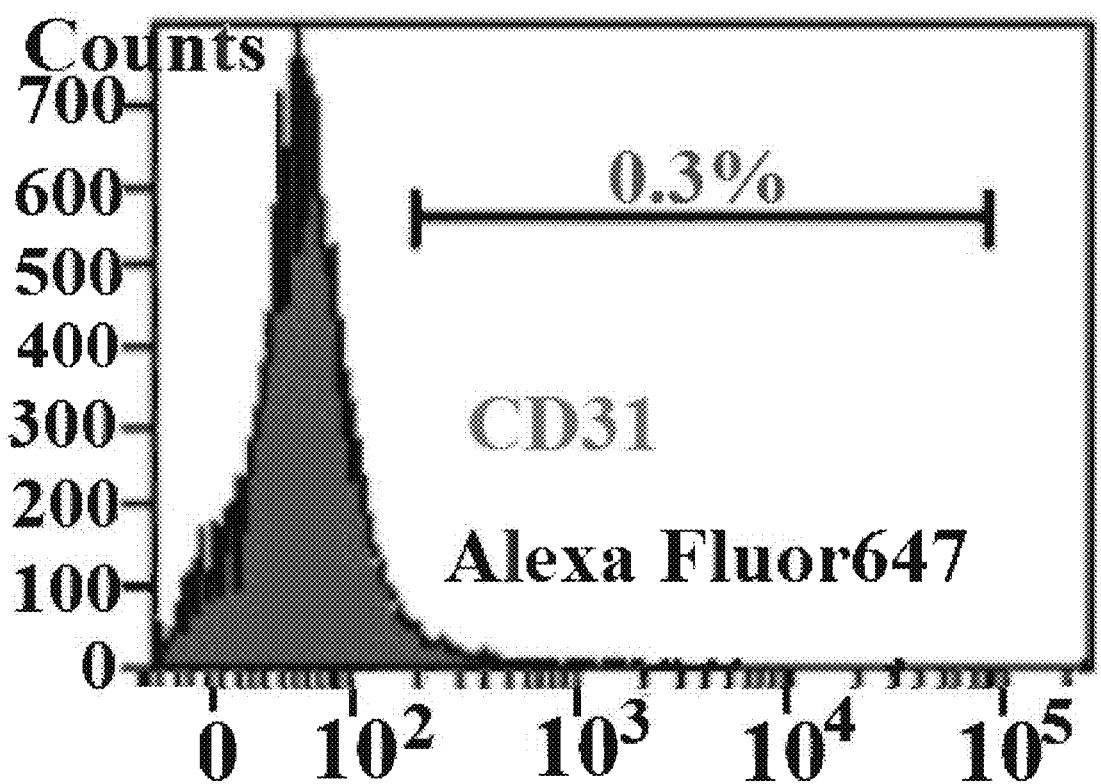

FIG. 11J shows the 1013A-MP surface antigen profile of CD31 measured by flow cytometry.

Figure 11K:
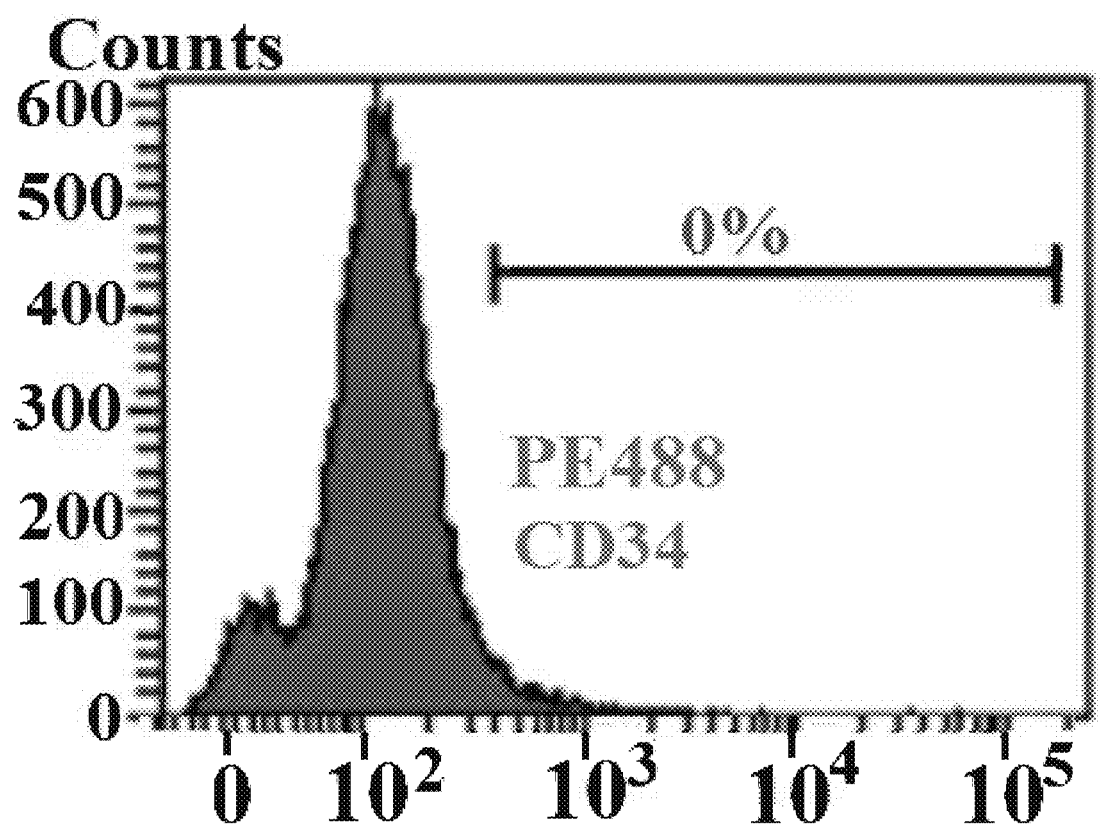

FIG. 11K shows the 1013A-MP surface antigen profile of CD34 measured by flow cytometry.

Figure 11L:
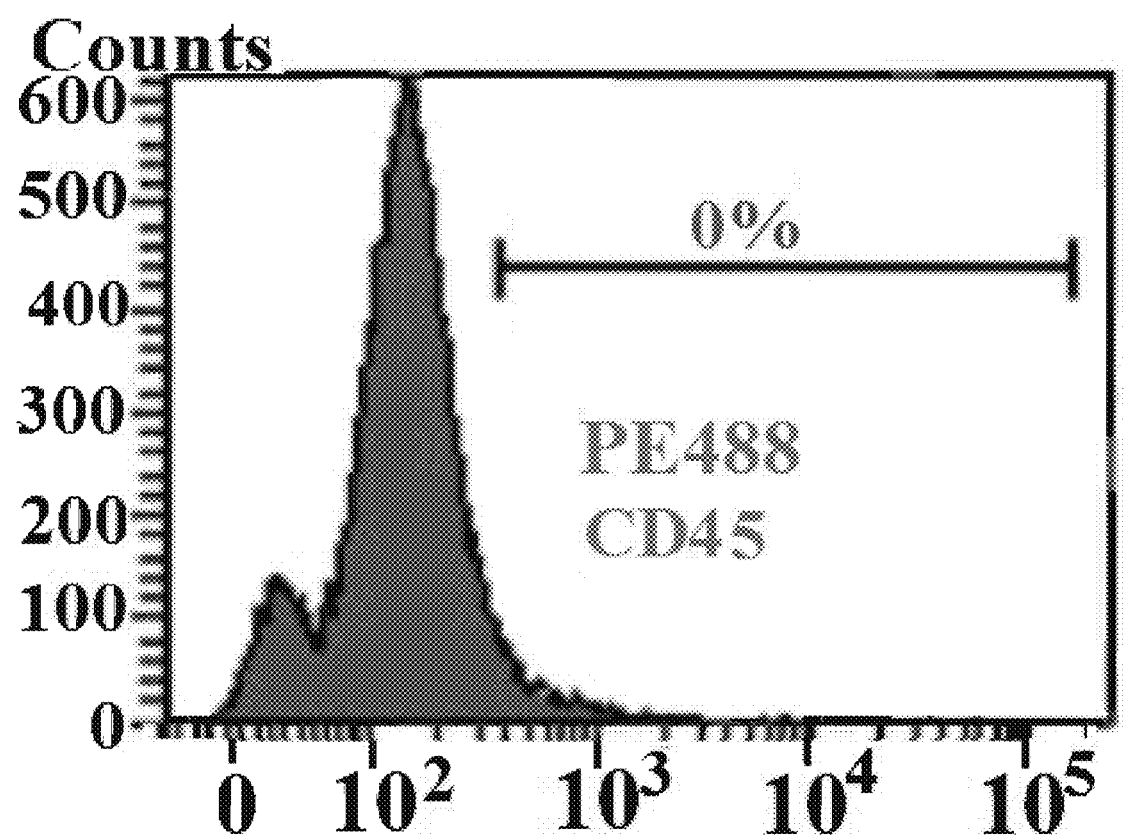

FIG. 11L shows the 1013A-MP surface antigen profile of CD45 measured by flow cytometry.

Figure 12A:
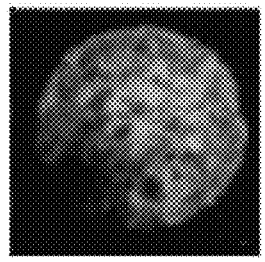

FIG. 12A is an image of cells calcein-stained after seeding on decellularized bone.

Figure 12B:
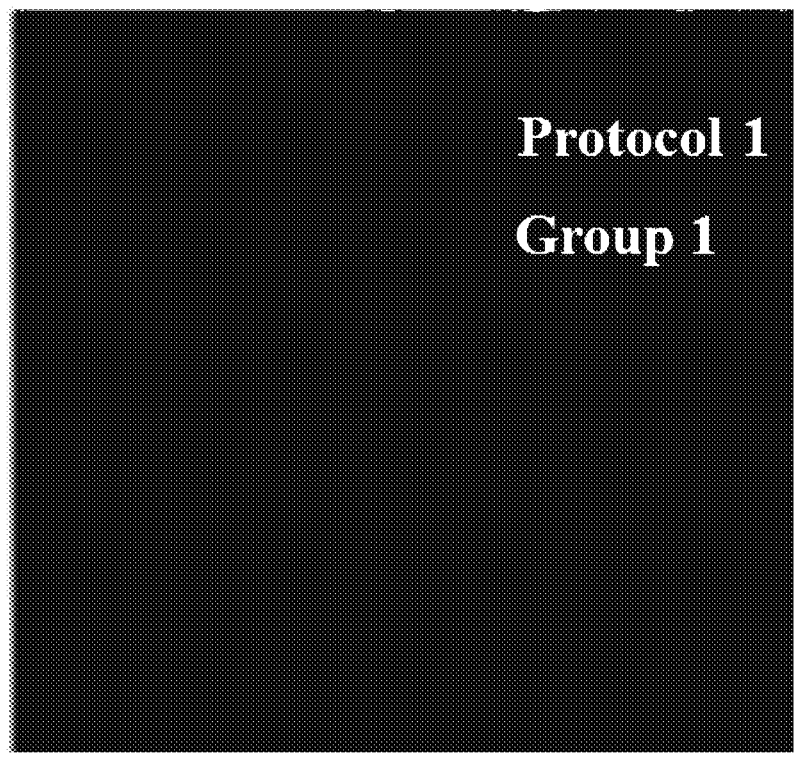

FIG. 12B is an image of cells calcein-stained after seeding on a Group 1 resin scaffold using seeding protocol 1.

Figure 12C:
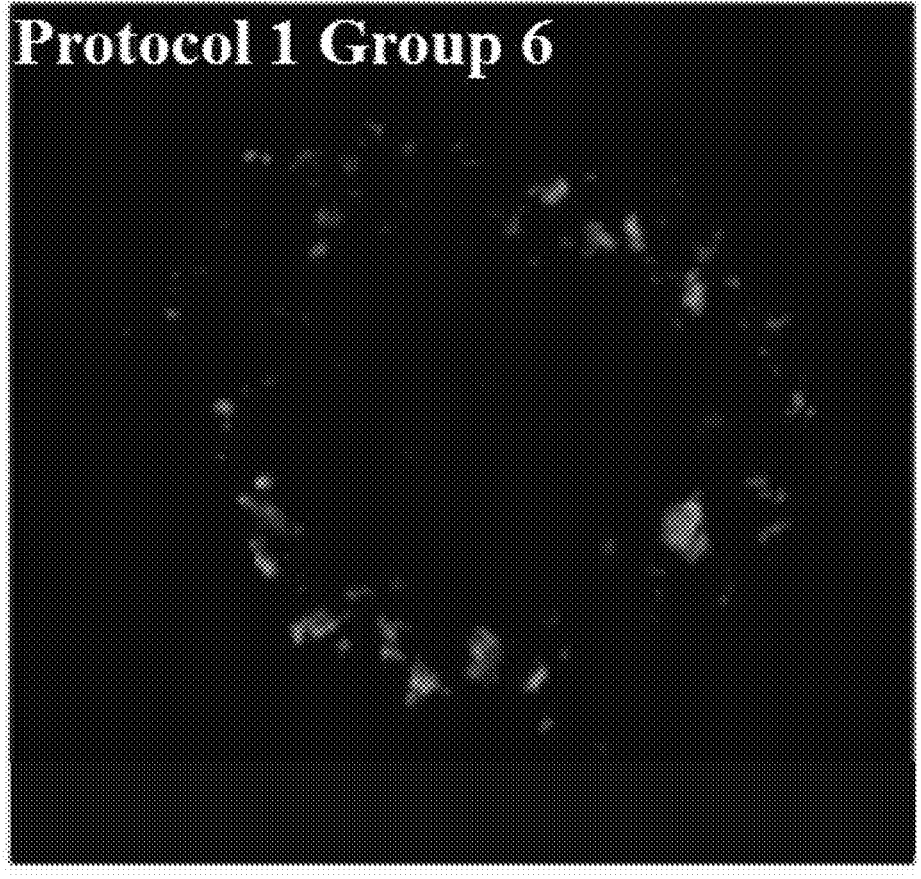

FIG. 12C is an image of cells calcein-stained after seeding on a Group 6 resin scaffold using seeding protocol 1.

Figure 12D:
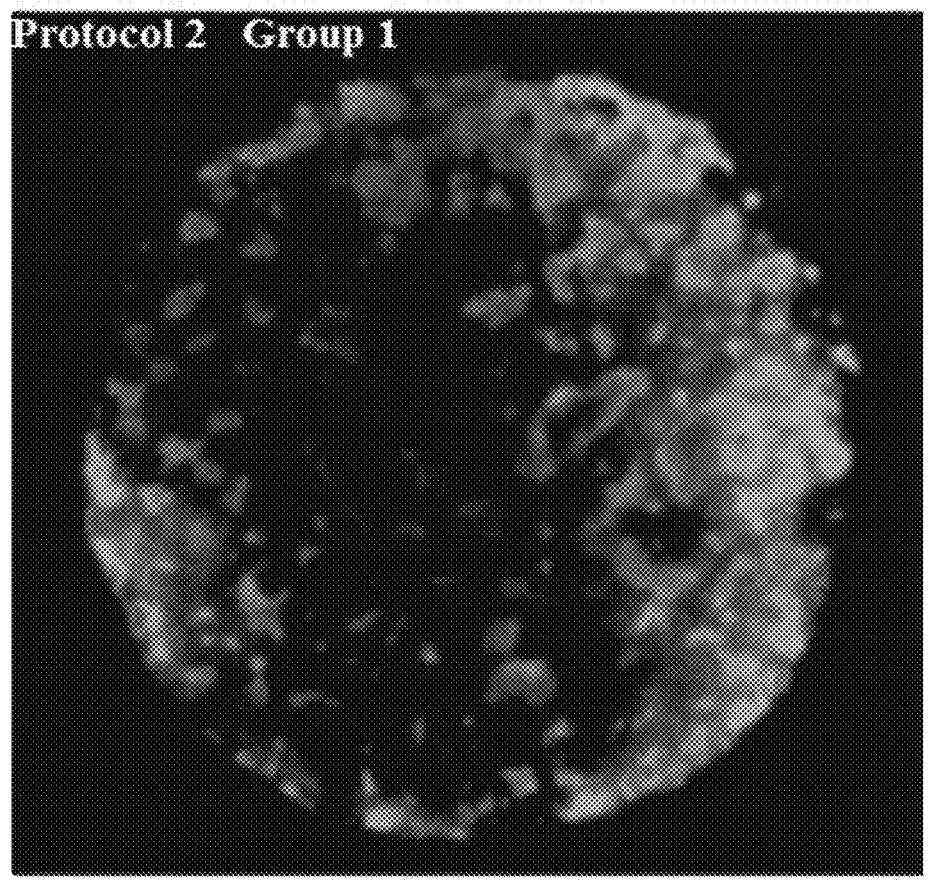

FIG. 12D is an image of cells calcein-stained after seeding on a Group 1 resin scaffold using seeding protocol 2.

Figure 12E:
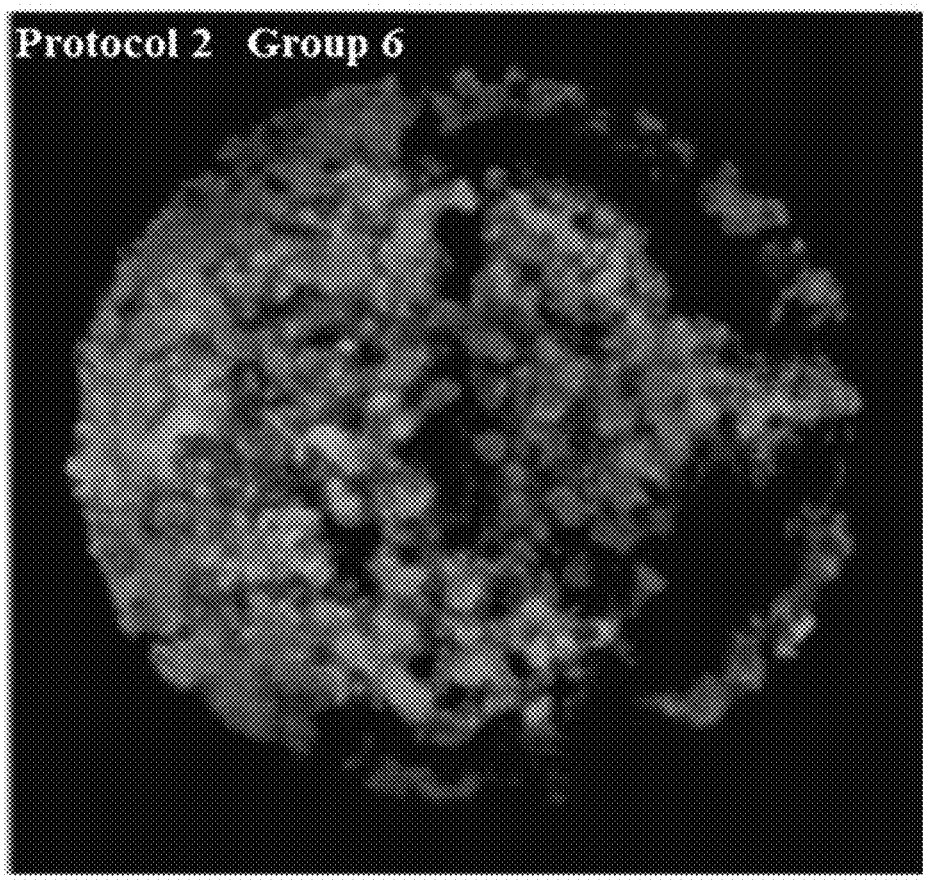

FIG. 12E is an image of cells calcein-stained after seeding on a Group 6 resin scaffold using seeding protocol 2.

Figure 13:
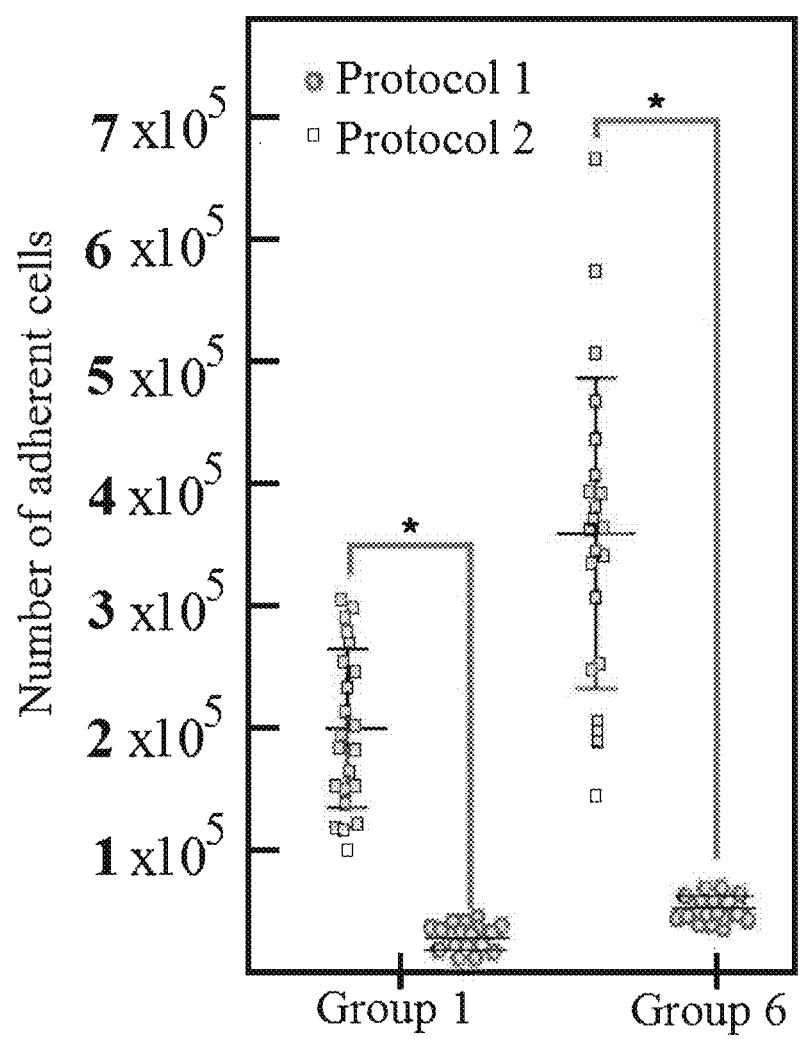

FIG. 13 is a plot of the number of adherent cells 1 day after seeding using protocol 1 and 2 for resin scaffold Groups 1 and 6.

Figure 14:
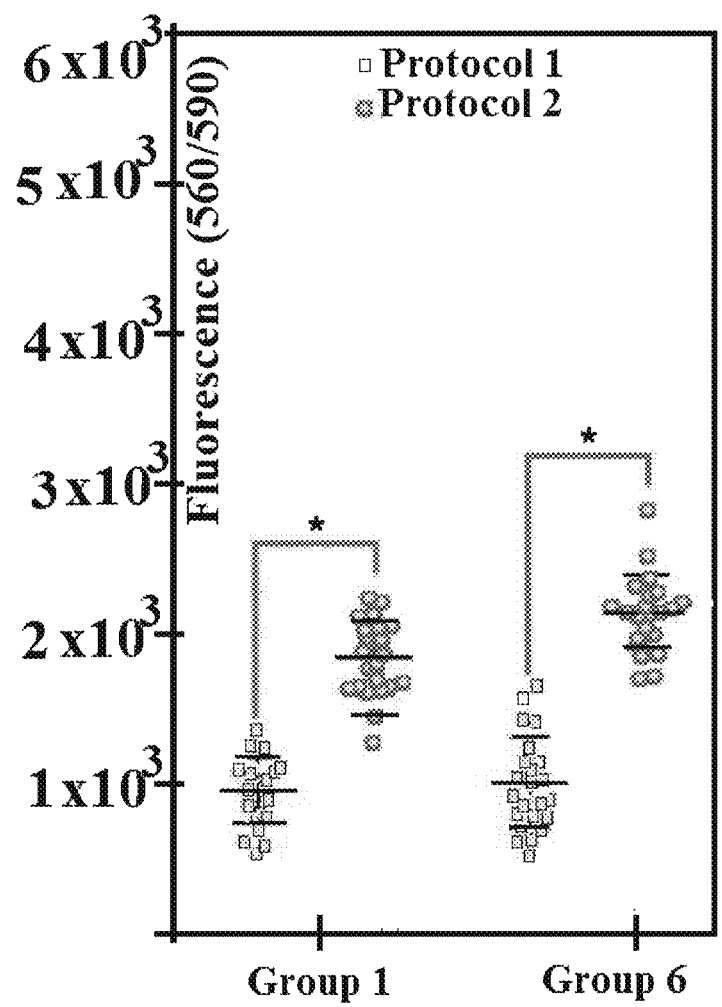

FIG. 14 is the fluorescence measurement of cells stained with PrestoBlue reagent after seeding with protocol 1 and 2 on resin scaffold Groups 1 and 6.

Figure 15A:
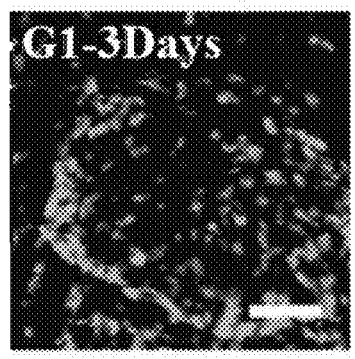

FIG. 15A shows live/dead stained 1013A-MP cells, grown under osteogenic conditions for 3 days on a Group 1 scaffold.

Figure 15B:
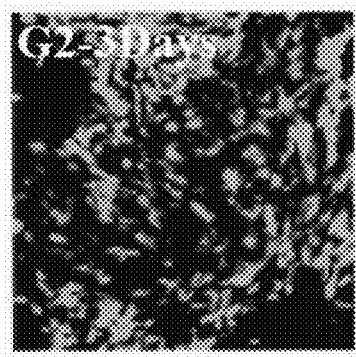

FIG. 15B shows live/dead stained 1013A-MP cells, grown under osteogenic conditions for 3 days on a Group 2 scaffold.

Figure 15C:
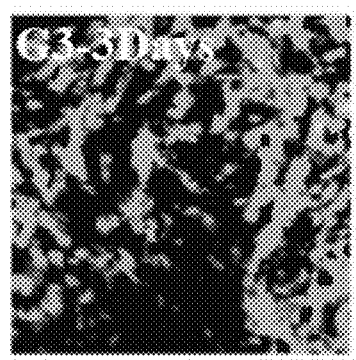

FIG. 15C shows live/dead stained 1013A-MP cells, grown under osteogenic conditions for 3 days on a Group 3 scaffold.

Figure 15D:
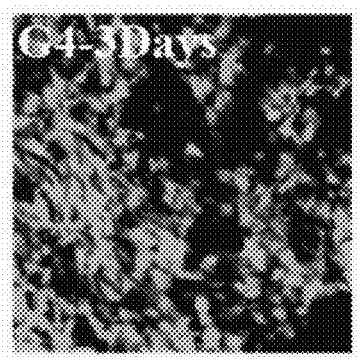

FIG. 15D shows live/dead stained 1013A-MP cells, grown under osteogenic conditions for 3 days on a Group 4 scaffold.

Figure 15E:
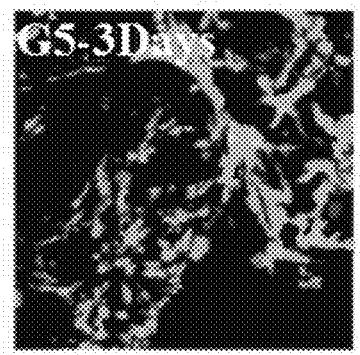

FIG. 15E shows live/dead stained 1013A-MP cells, grown under osteogenic conditions for 3 days on a Group 5 scaffold.

Figure 15F:
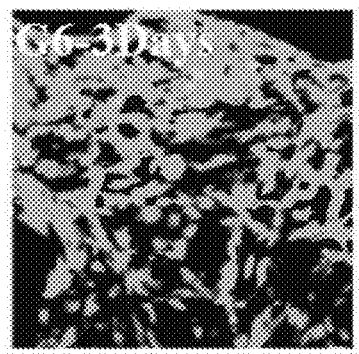

FIG. 15F shows live/dead stained 1013A-MP cells, grown under osteogenic conditions for 3 days on a Group 6 scaffold.

Figure 15G:
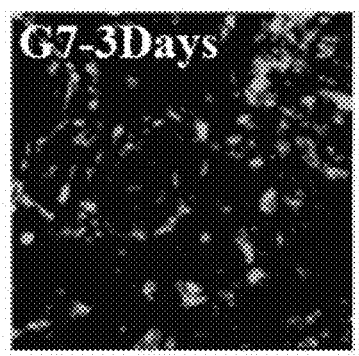

FIG. 15G shows live/dead stained 1013A-MP cells, grown under osteogenic conditions for 3 days on a Group 7 scaffold.

Figure 15H:
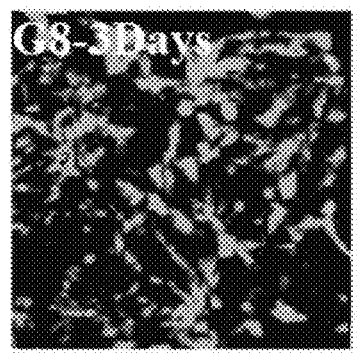

FIG. 15H shows live/dead stained 1013A-MP cells, grown under osteogenic conditions for 3 days on a Group 8 scaffold.

Figure 15I:
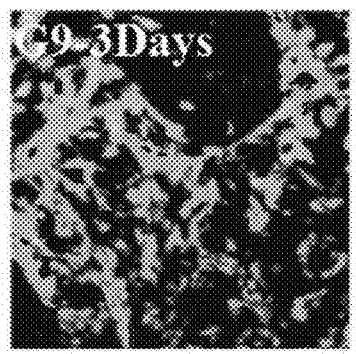

FIG. 15I shows live/dead stained 1013A-MP cells, grown under osteogenic conditions for 3 days on a Group 9 scaffold.

Figure 15J:

FIG. 15J shows live/dead stained 1013A-MP cells, grown under osteogenic conditions for 3 days on decellularized bone.

Figure 16A:

FIG. 16A shows live/dead stained 1013A-MP cells, grown under osteogenic conditions for 3 weeks on a Group 1 scaffold.

Figure 16B:

FIG. 16B shows live/dead stained 1013A-MP cells, grown under osteogenic conditions for 3 weeks on a Group 2 scaffold.

Figure 16C:
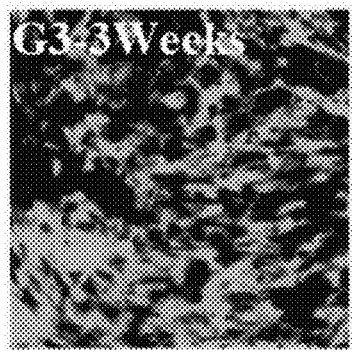

FIG. 16C shows live/dead stained 1013A-MP cells, grown under osteogenic conditions for 3 weeks on a Group 3 scaffold.

Figure 16D:
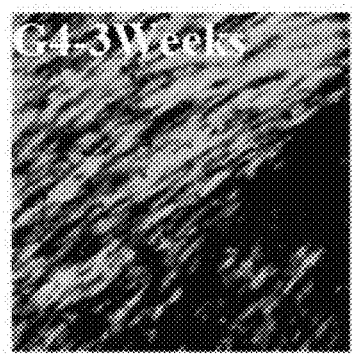

FIG. 16D shows live/dead stained 1013A-MP cells, grown under osteogenic conditions for 3 weeks on a Group 4 scaffold.

Figure 16E:
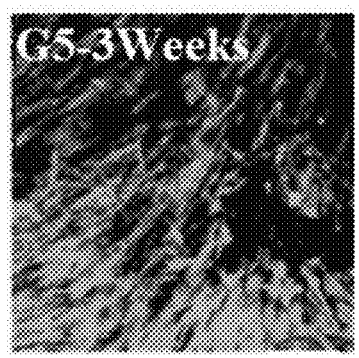

FIG. 16E shows live/dead stained 1013A-MP cells, grown under osteogenic conditions for 3 weeks on a Group 5 scaffold.

Figure 16F:
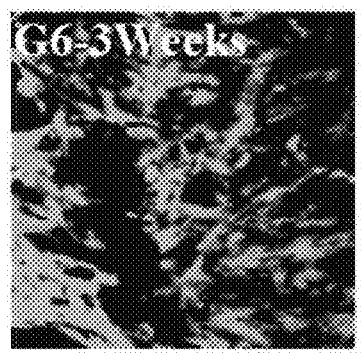

FIG. 16F shows live/dead stained 1013A-MP cells, grown under osteogenic conditions for 3 weeks on a Group 6 scaffold.

Figure 16G:

FIG. 16G shows live/dead stained 1013A-MP cells, grown under osteogenic conditions for 3 weeks on a Group 7 scaffold.

Figure 16H:

FIG. 16H shows live/dead stained 1013A-MP cells, grown under osteogenic conditions for 3 weeks on a Group 8 scaffold.

Figure 16I:

FIG. 16I shows live/dead stained 1013A-MP cells, grown under osteogenic conditions for 3 weeks on a Group 9 scaffold.

Figure 16J:
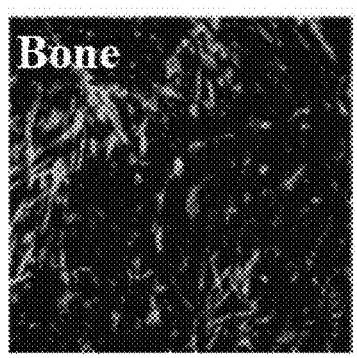

FIG. 16J shows live/dead stained 1013A-MP cells, grown under osteogenic conditions for 3 weeks on decellularized bone.

Figure 17A:

FIG. 17A shows live/dead stained 1013A-MP cells, grown under osteogenic conditions for 7 weeks on a Group 1 scaffold.

Figure 17B:
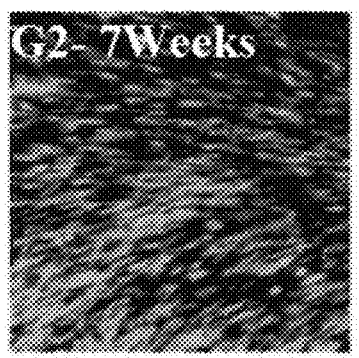

FIG. 17B shows live/dead stained 1013A-MP cells, grown under osteogenic conditions for 7 weeks on a Group 2 scaffold.

Figure 17C:
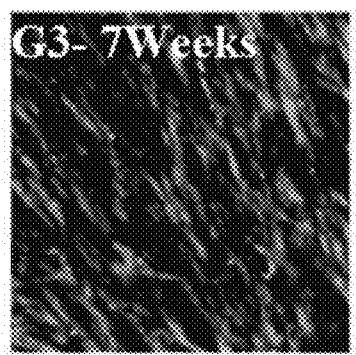

FIG. 17C shows live/dead stained 1013A-MP cells, grown under osteogenic conditions for 7 weeks on a Group 3 scaffold.

Figure 17D:
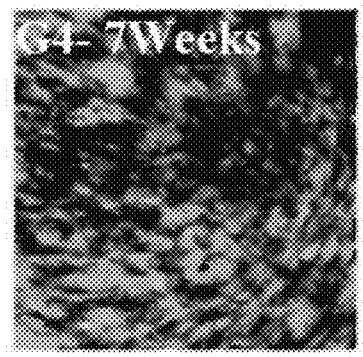

FIG. 17D shows live/dead stained 1013A-MP cells, grown under osteogenic conditions for 7 weeks on a Group 4 scaffold.

Figure 17E:
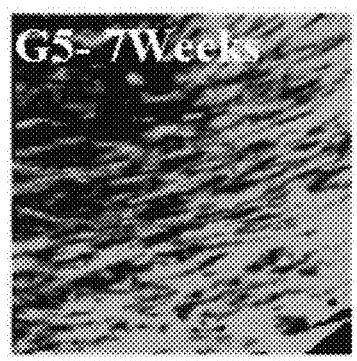

FIG. 17E shows live/dead stained 1013A-MP cells, grown under osteogenic conditions for 7 weeks on a Group 5 scaffold.

Figure 17F:
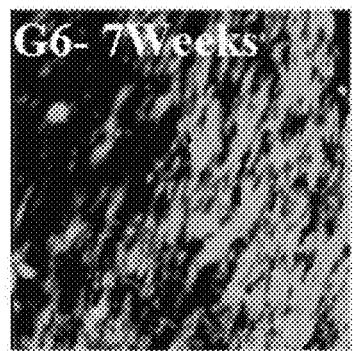

FIG. 17F shows live/dead stained 1013A-MP cells, grown under osteogenic conditions for 7 weeks on a Group 6 scaffold.

Figure 17G:

FIG. 17G shows live/dead stained 1013A-MP cells, grown under osteogenic conditions for 7 weeks on a Group 7 scaffold.

Figure 17H:
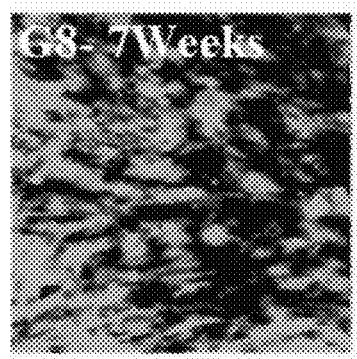

FIG. 17H shows live/dead stained 1013A-MP cells, grown under osteogenic conditions for 7 weeks on a Group 8 scaffold.

Figure 17I:
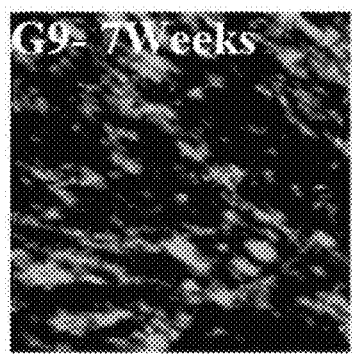

FIG. 17I shows live/dead stained 1013A-MP cells, grown under osteogenic conditions for 7 weeks on a Group 9 scaffold.

Figure 17J:

FIG. 17J shows live/dead stained 1013A-MP cells, grown under osteogenic conditions for 7 weeks on decellularized bone.

Figure 18A:
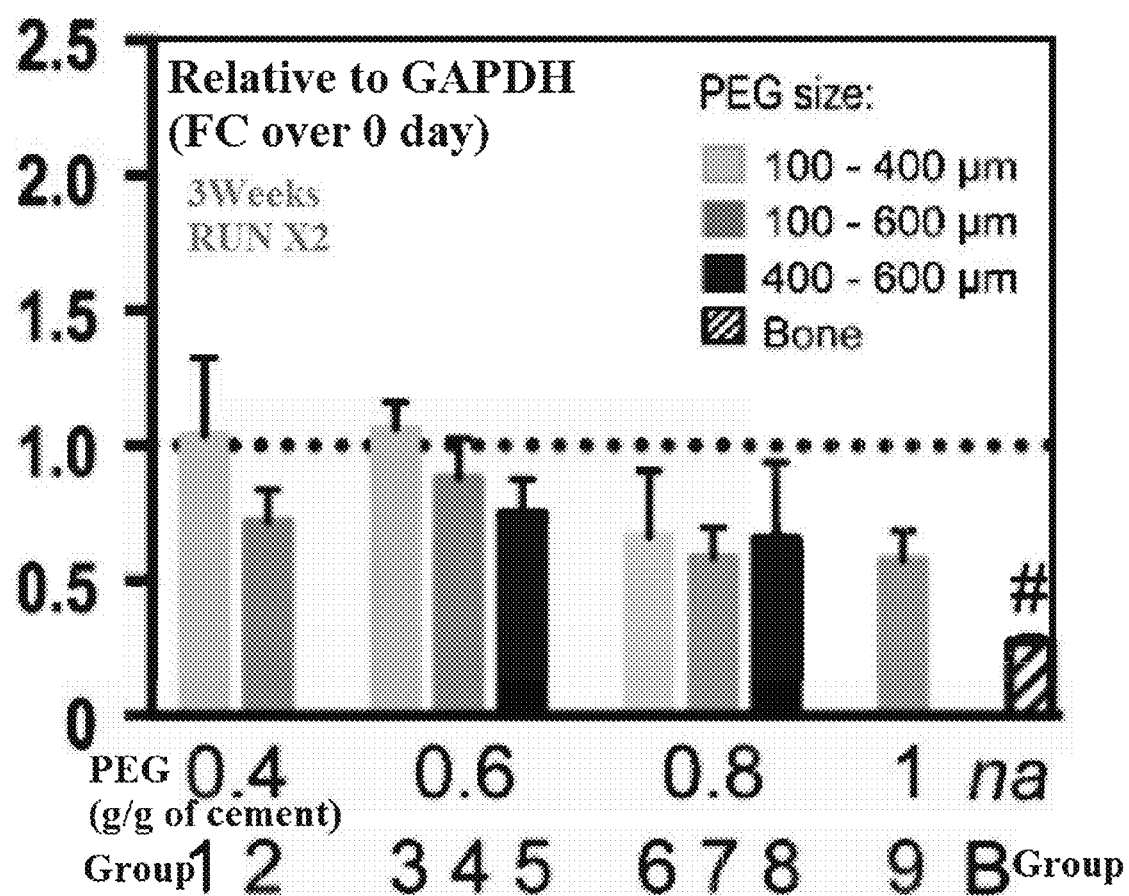

FIG. 18A shows the expression level of RUNX2 in 1013A-MP cells 3 weeks after seeding on different surfaces (resin scaffolds or decellularized bone).

Figure 18B:
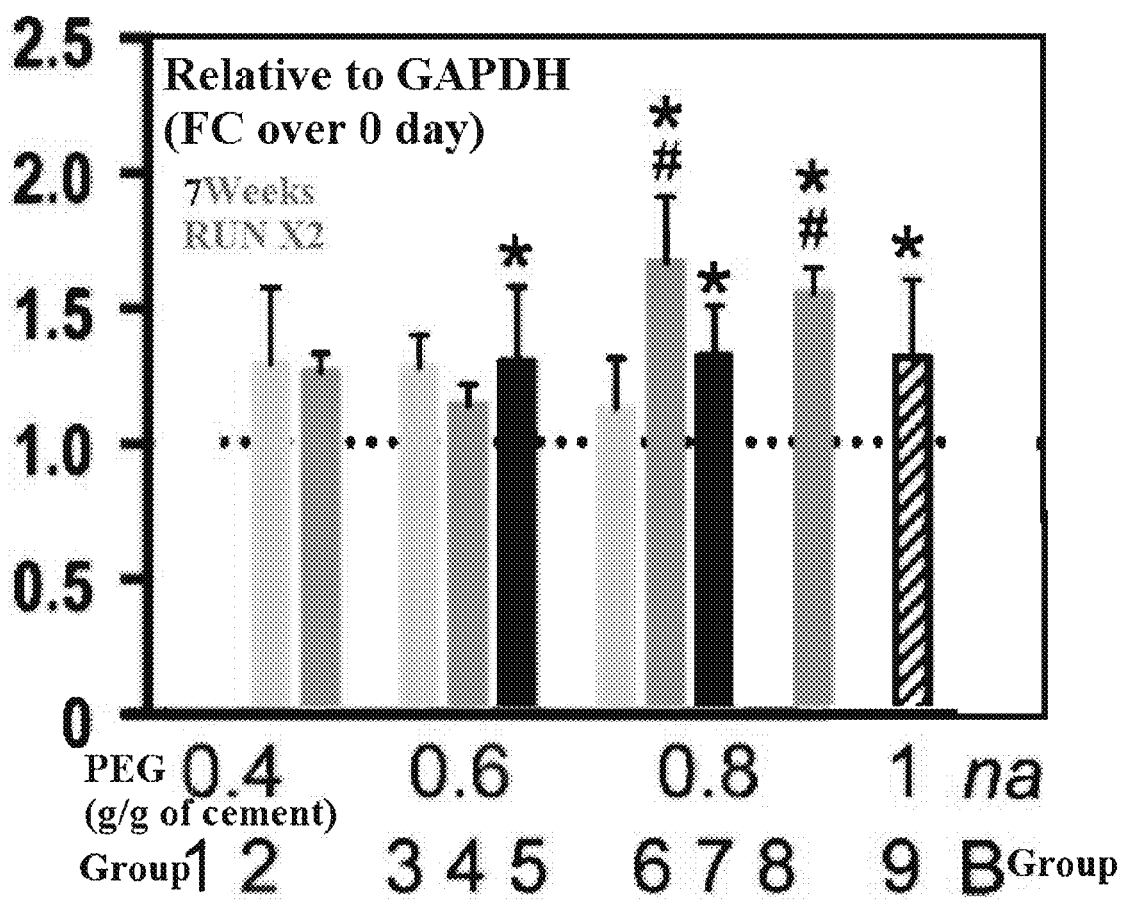

FIG. 18B shows the expression level of RUNX2 in 1013A-MP cells 7 weeks after seeding on different surfaces.

Figure 18C:
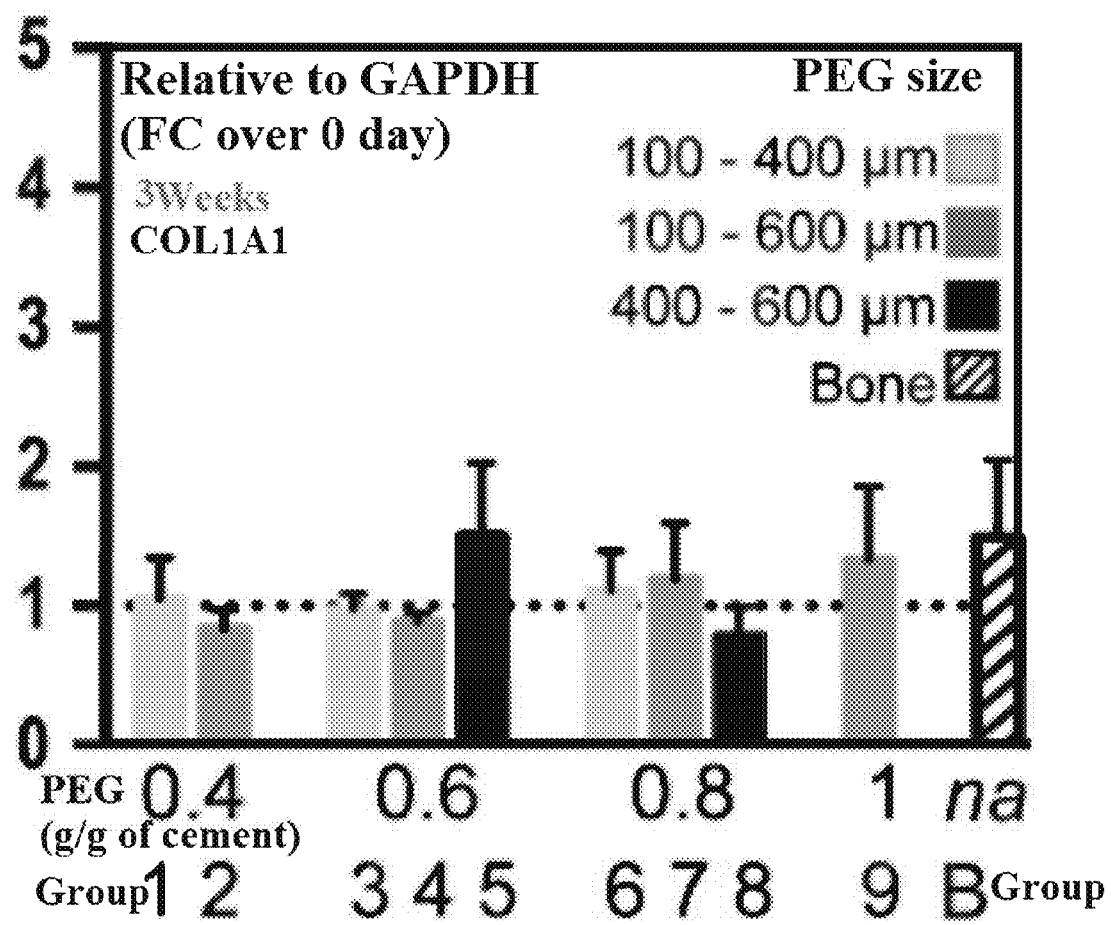

FIG. 18C shows the expression level of COL1A1 in 1013A-MP cells 3 weeks after seeding on different surfaces.

Figure 18D:
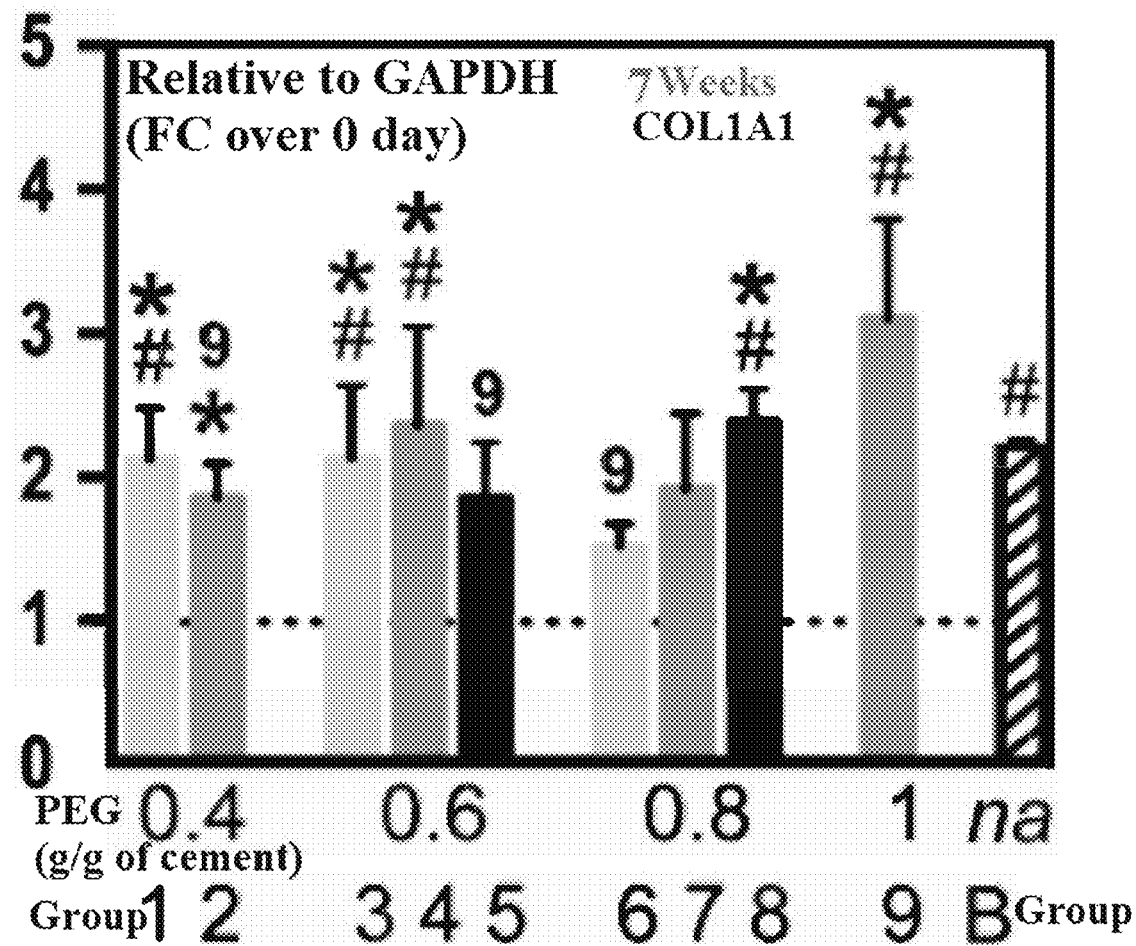

FIG. 18D shows the expression level of COL1A1 in 1013A-MP cells 7 weeks after seeding on different surfaces.

Figure 18E:
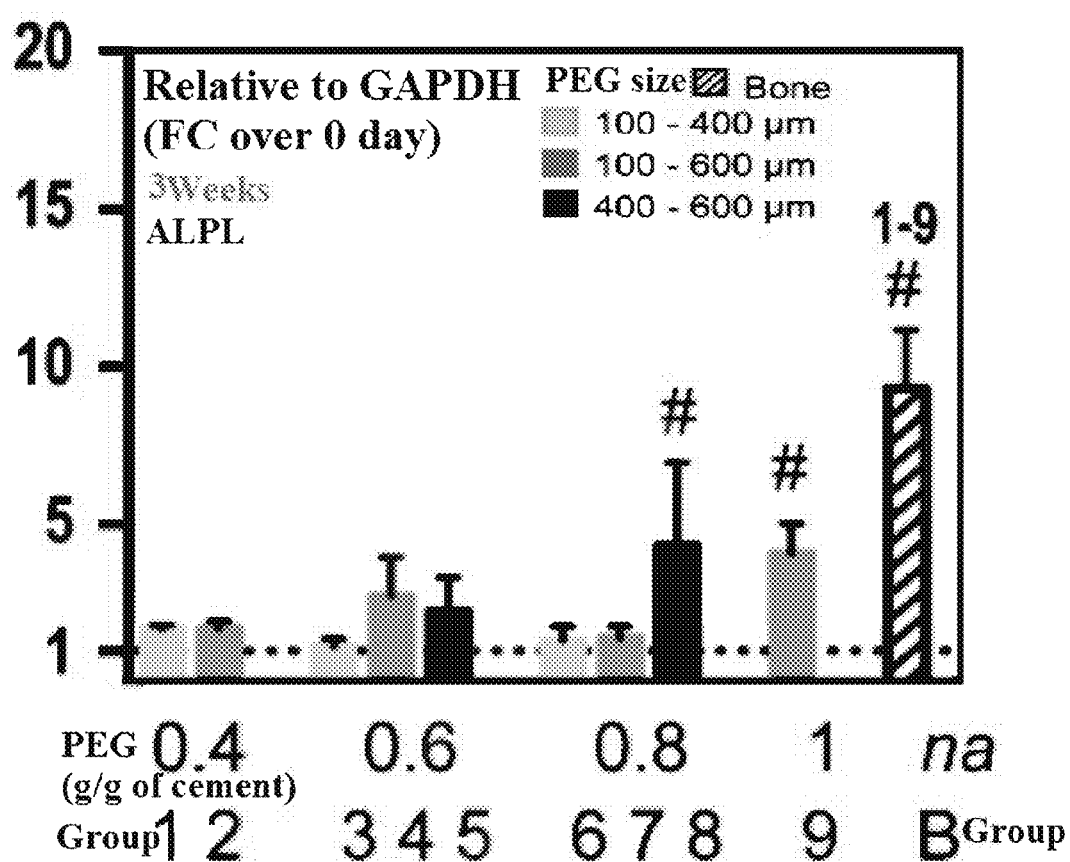

FIG. 18E shows the expression level of ALPL in 1013A-MP cells 3 weeks after seeding on different surfaces.

Figure 18F:
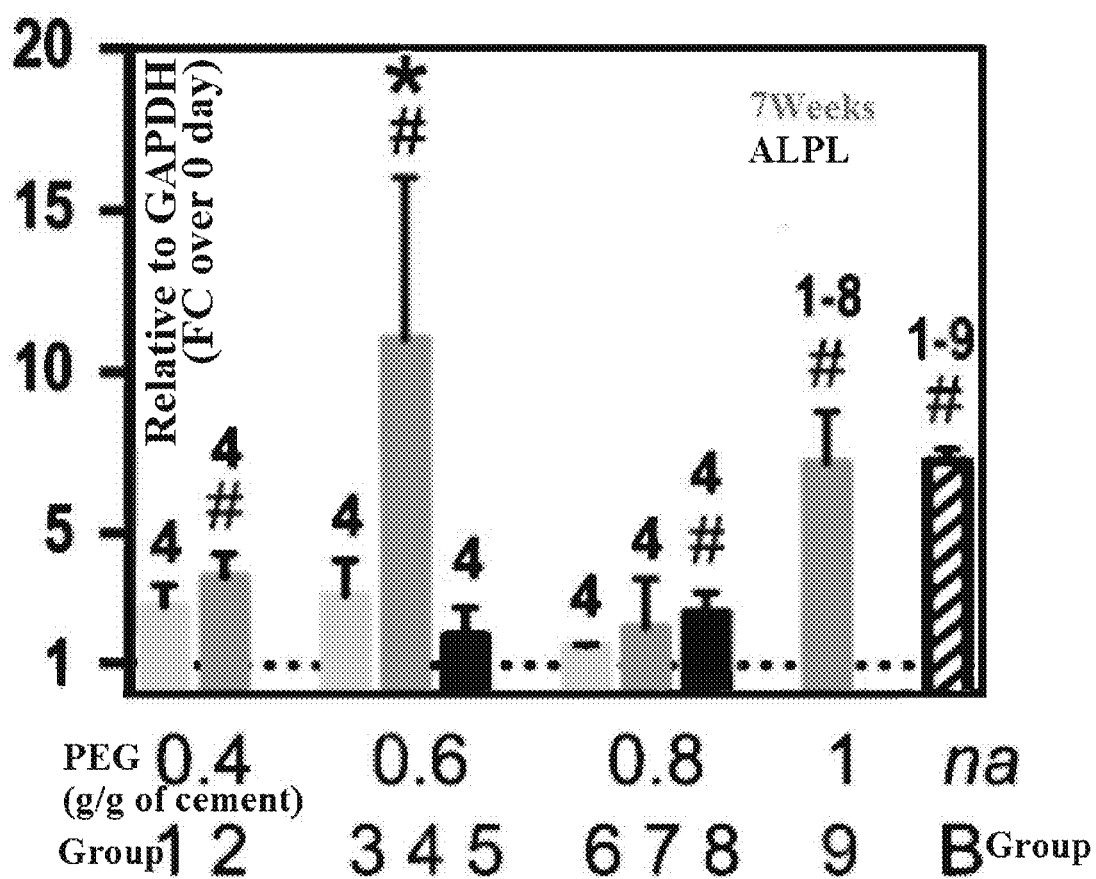

FIG. 18F shows the expression level of ALPL in 1013A-MP cells 7 weeks after seeding on different surfaces.

Figure 18G:
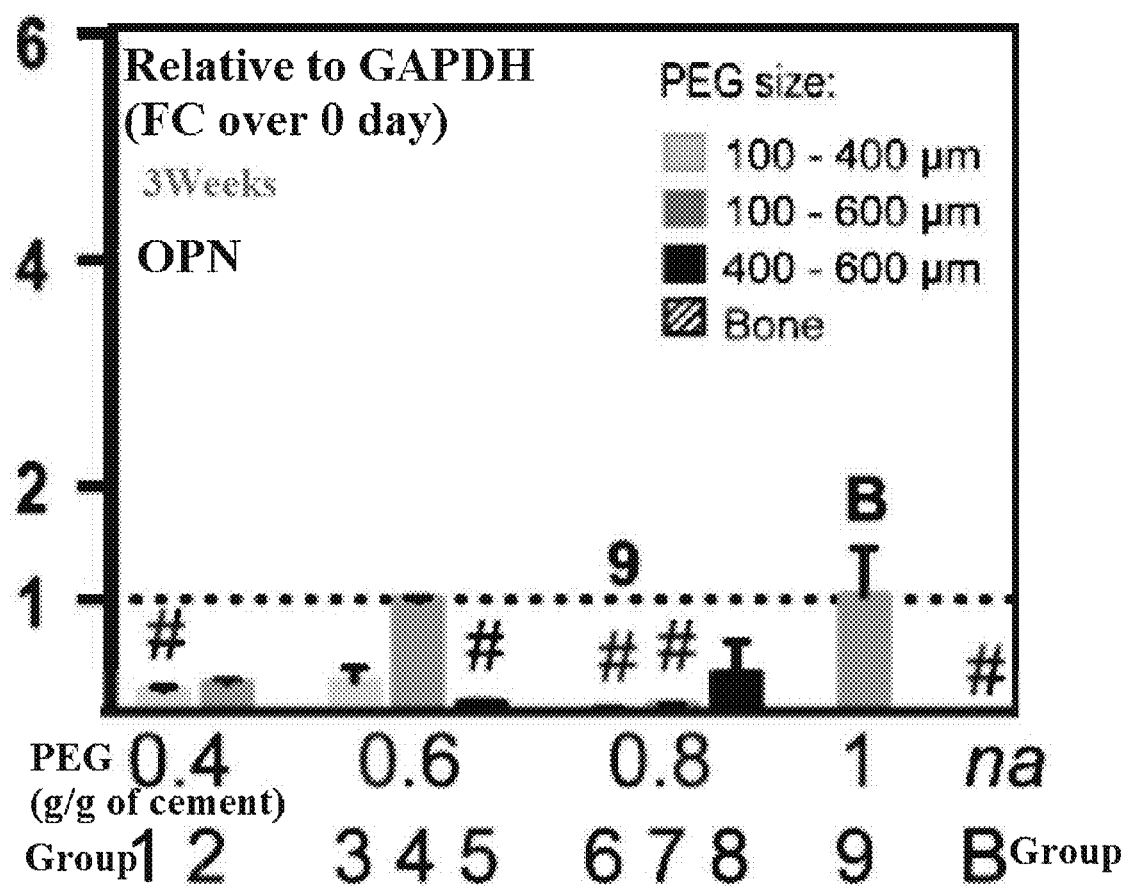

FIG. 18G shows the expression level of OPN in 1013A-MP cells 3 weeks after seeding on different surfaces.

Figure 18H:
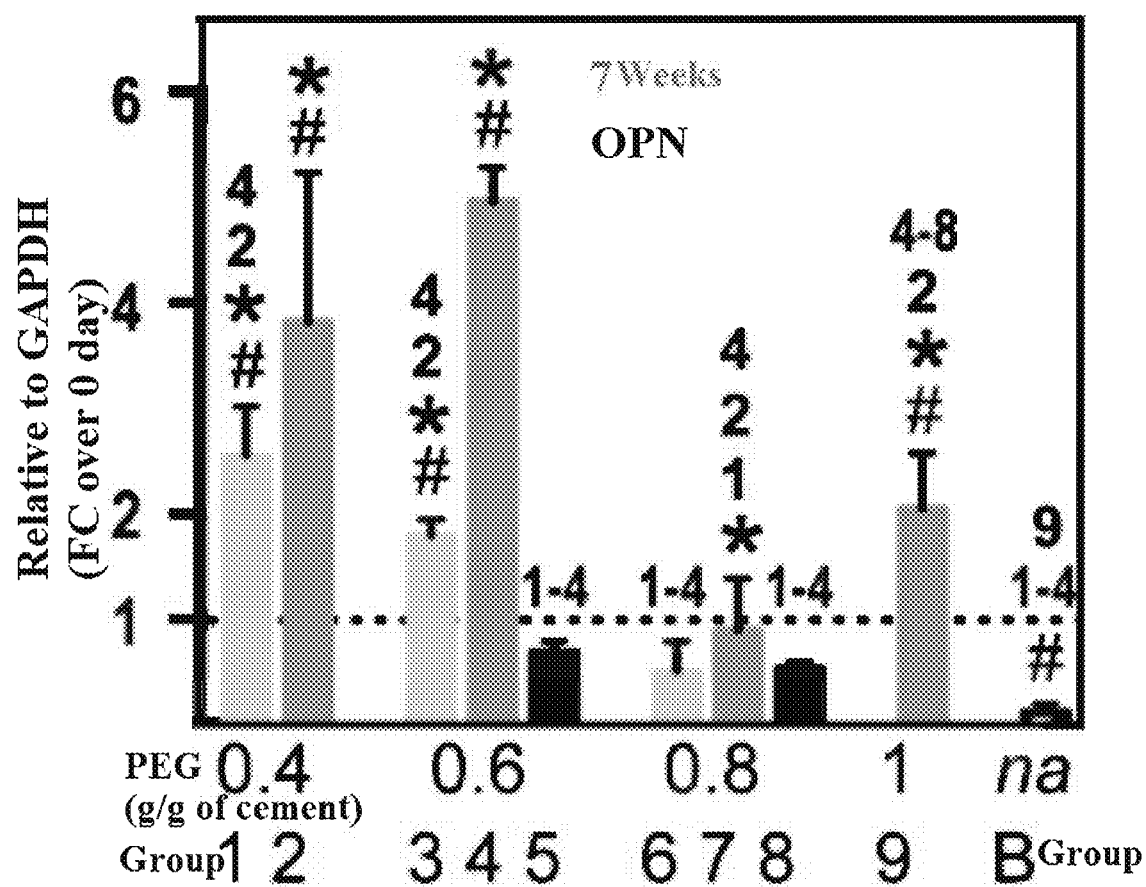

FIG. 18H shows the expression level of OPN in 1013A-MP cells 7 weeks after seeding on different surfaces.

Figure 18I:
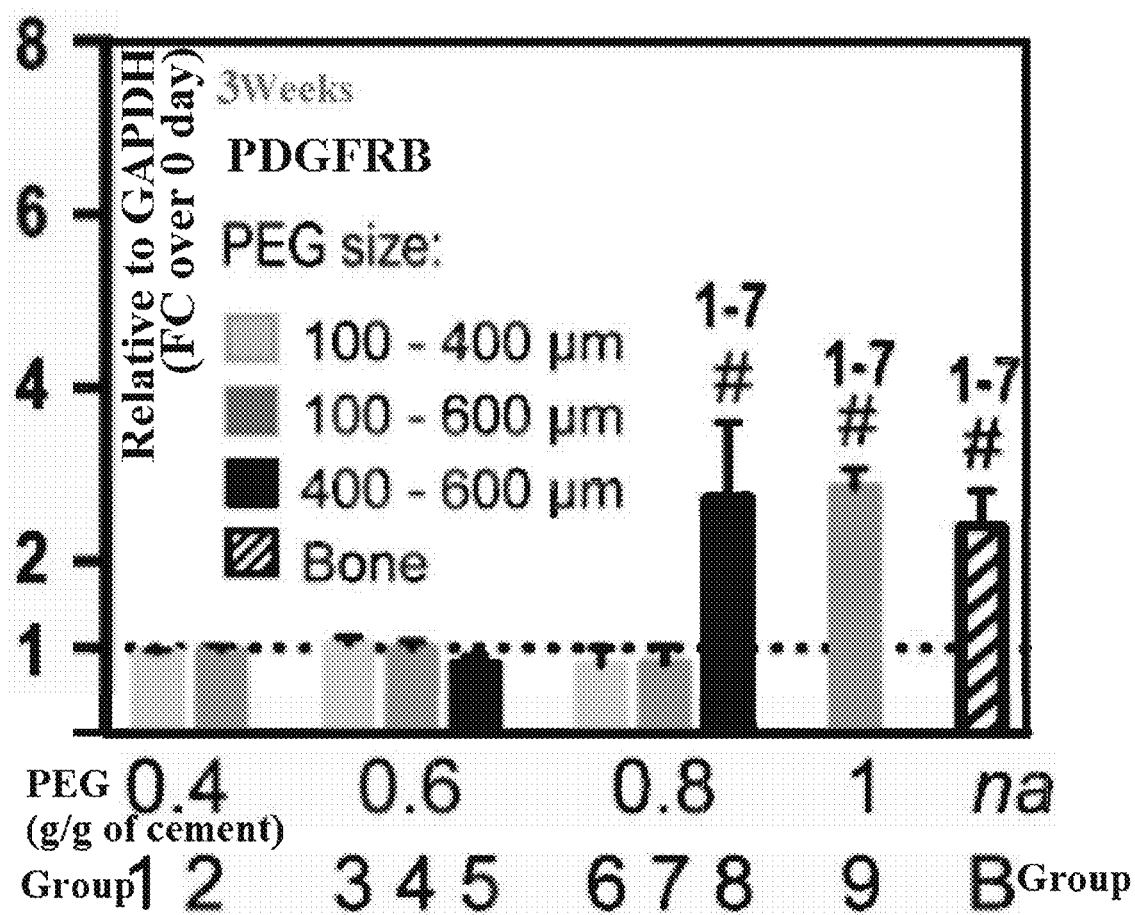

FIG. 18I shows the expression level of PDGFRB in 1013A-MP cells 3 weeks after seeding on different surfaces.

Figure 18J:
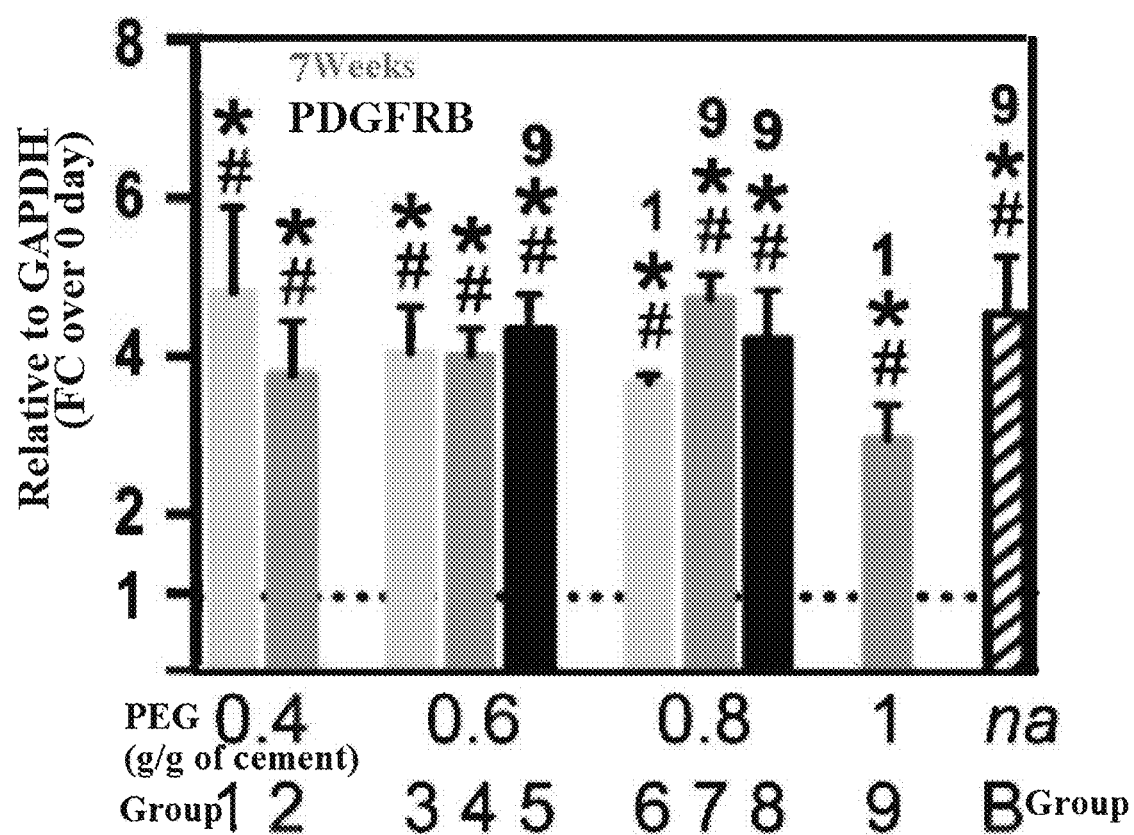

FIG. 18J shows the expression level of PDGFRB in 1013A-MP cells 7 weeks after seeding on different surfaces.

DETAILED DESCRIPTION OF THE EMBODIMENTS

Embodiments of the present disclosure will now be described more fully hereinafter with reference to the accompanying drawings, in which some, but not all embodiments of the disclosure are shown.

The present disclosure will be better understood with reference to the following terms and meanings set forth below. Unless defined otherwise, all technical and scientific terms used herein have the same meaning as commonly understood to one of ordinary skill in the art.

As used herein, the term "biocompatible" denotes being biologically compatible by not producing a toxic, injurious, or immunological response when in physical contact with a living cell or tissue.

As used herein, the term "porosity" is the percentage of void volume of a material's bulk volume that can be reached from the exterior surfaces of the material. In the current disclosure, macroporosity, mesoporosity, and microporosity all refer to porosity. As defined here, a macroporous material contains pores with an average diameter greater than 50 nm; a mesoporous material contains pores with an average diameter of 2 nm-50 nm, and a microporous material contains pores with an average diameter less than 2 nm.

According to a first aspect, the present disclosure relates to a biocompatible bone graft which includes a porous scaffold structure comprising a tannin-hydroxyapatite resin, a population of osteocompetent stem cells obtained from a mammalian donor, and a growth medium.

The tannin-hydroxyapatite resin of the porous scaffold structure may have a porosity of 5-90 vol %, preferably 10-95 vol %, more preferably 17-80 vol %; a pore diameter of 10-700 μm, preferably 25-500 μm, more preferably 40-300 μm; and a compressive strength of 0.05-3.00 MPa, preferably 0.01-2.50 MPa, more preferably 0.15-1.90 MPa. The tannin-hydroxyapatite resin of the porous scaffold structure may have a bulk density of 0.10-0.50 g/cm$^3$, preferably 0.20-0.40 g/cm$^3$, more preferably 0.27-0.35 g/cm$^3$.

The porous scaffold structure may be formed in the shape of a cuboid, spheroid, ovoid, ellipsoid, or other irregular shape, and with ends that may be rounded, squared, tapered, beveled, conical, concave, convex, scalloped, angular, or in some other form. Additionally, the porous scaffold structure may be formed in one shape and then filed, drilled, sanded, cut, or grinded into another shape. The optimal shape and dimensions for the scaffold structure as a bone graft depend on the size and location of the bone wound site, and the presence of other materials, such as an orthopedic implant. The longest dimension of the porous scaffold structure may range from 4-20 mm, preferably 5-12 mm, more preferably 6-10 mm. The shortest dimension of the porous scaffold structure may range from 1-10 mm, preferably 1-8 mm, more preferably 1-5 mm. In one embodiment, the porous scaffold structure has a cylindrical shape with an 8 mm diameter and a 2 mm height.

The tannin-hydroxyapatite resin is made of a tannin extract chemically cross-linked in a mixture that also contains hydroxyapatite. This creates a matrix of cross-linked tannin molecules in which hydroxyapatite is adsorbed and embedded throughout.

In one embodiment, the hydroxyapatite is dispersed within the tannin matrix, and no chemical bonding is present therebetween.

Here, tannin may be extracted from *mimosa, acacia*, wattle, quebracho, pine, spruce, fir, tanoak, hemlock, mangrove, gambier, oak, birch, maple, *eucalyptus*, tara, and/or *catechu* trees, or mixtures thereof, and may come from the leaf, bud, seed, root, bark, trunk, and/or stem tissue. Preferably the tannin is extracted from the bark of *mimosa*, quebracho, or wattle trees.

Tannin refers to a group of plant-based oligomeric polyphenolic compounds. The tannin extract used for the resin may include a mixture of condensed, flavonoid tannin molecules and hydrolyzable tannin molecules. Condensed, flavonoid tannin molecules are based on flavon-3-ol monomers (1) and generally contain 3-6 hydroxyl groups per monomeric unit. Examples of common condensed tannin molecules include, but are not limited to, those based on prorobinetinidin (II), profisetinidin (III), procyanidin (IV), and prodelphinidin (V) flavonoid units and are connected through bonds at C4, C6, and/or C8. The major tannin constituent in pine bark extract may be procyanidin (IV) with an average degree of polymerization between 6 and 7, with units linked through C4 and C8. The major tannin constituent in *mimosa* tannin may be profisetinidin (III) and prorobinetinidin (II), with an average degree of polymerization between 4 and 5, with units linked through C4 and C6. Hydrolyzable tannin molecules may contain a saccharide and may be a type of gallotannin or ellagitannin, which are oligomers of gallic acid (galloyl) units (VI) connected through ester or C—C bonds, respectively. One example of a common gallotannin is tannic acid, with one polymeric form shown in formula VII. Gallotannins may contain 2-12 galloyl groups per molecule, with each galloyl group having 2-3 hydroxyl groups and one ester group. It is further possible to have complex tannins in which a condensed, flavonoid tannin is bound to a gallotannin and/or an ellagitannin.

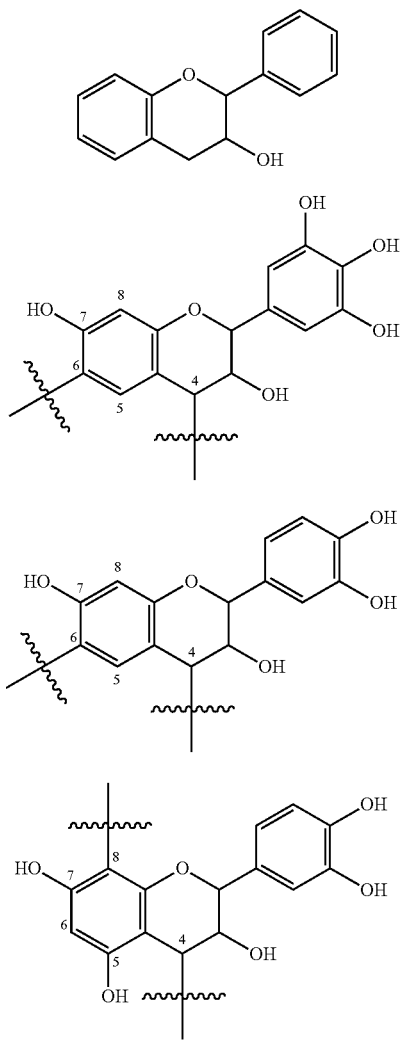

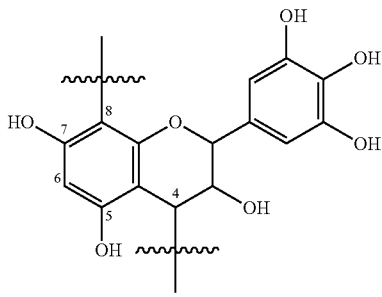

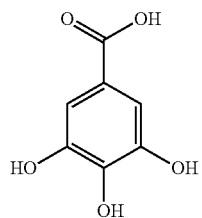

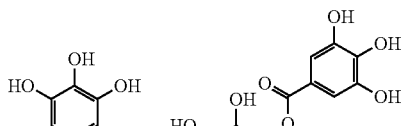

In a preferred embodiment, the tannin is a prorobinetinidin oligomer of molecular weight 0.5-3.5 kDa and is extracted from *mimosa* tree bark. In another embodiment, condensed polyflavonoid tannins with a molecular weight greater than 3.5 kDa may be used in the resin. In an alternative embodiment, monomeric flavoinoid units and condensed polyflavonoid tannins with a molecular weight less than 1 kDa may be used in the tannin resin. In an alternative embodiment, the tannin used for the tannin resin may contain a mixture of both condensed tannins (containing flavan-3-ol units), hydrolyzable tannins (containing galloyl units), and complex tannins (containing both flavan-3-ol and galloyl units). In this mixture, the molar ratio of total galloyl units to total flavan-3-ol units may range from 4:1-1:100, preferably 1:1-1:100, more preferably 1:4-1:100.

In one embodiment, tannin from an aqueous tannin extract may be chemically modified prior to cross-linking, which may change the mechanical, chemical, and/or biological properties of the tannin resin. In another embodiment, the chemical modification changes the reaction conditions needed to form the tannin resin. The hydroxyl sites of tannin molecules may be methylated, carboxymethylated, acylated, alkoxylated, substituted with ammonia, reacted with isocyanates, and/or etherified. Other parts of tannin molecules may be sulfonated, hydrolyzed, condensed, halogenated, or reacted with furfuryl alcohol. In addition, tannin may be esterified with fatty acids including, but not limited to, oleic acid, linoleic acid, elaidic acid, erucic acid, gondoic acid, paullinic acid, γ-linolenic acid, α-linolenic acid, and/or stearidonic acid.

In one embodiment, the tannin is functionalized fully or partially with reactive functional groups to chemically bind the hydroxyapatite within the resin. This may be accomplished with a reagent that may crosslink the hydroxyl groups of the tannin with the hydroxyl groups of the hydroxyapatite. Such a reagent may be a diisocyanate such as methylene diphenyl diisocyanate (MDI), toluene diisocyanate (TDI), isophorone diisocyanate (IPDI), and/or hexamethylene diisocyanate (HDI).

An aqueous tannin extract may be dried to create a tannin powder for use in the tannin-hydroxyapatite resin. The powder may be formed by spray drying, freeze drying, air drying, or vacuum drying the extract. Preferably, the powder is formed by spray drying. The formed powder may comprise 60-95 wt %, preferably 70-90 wt %, more preferably 78-85 wt % flavonoid tannins, with the remaining portion of the dried residue comprising hemicellulose fragments, hydrolyzable tannins, complex tannins, amino acids, imino acids, and/or water. It is possible that the extract may be purified prior to drying in order to enrich the concentration of flavonoid tannins. The dried tannin powder particles may have an average largest dimension of 150 μm or smaller, preferably 75 μm or smaller, more preferably 50 μm or smaller.

Hydroxyapatite and a dry porogen are mixed with the tannin powder to form a powder mixture. As used herein, a "porogen" is a non-reacting substance added to a liquid settable material in order to reserve the space that forms pores. The mass ratio of hydroxyapatite to tannin may be in the range of 1:10-2:1, preferably 1:8-1:1, more preferably 1:5-1:3. The mass ratio of the dry porogen to tannin may be in the range of 4:1 to 1:2, preferably 3:1 to 1:1.5, more preferably 2.5:1 to 1:1. Hydroxyapatite within the resin may support the growth and differentiation of the osteocompetent stem cells, as well as supply a starting mineralization source. In an envisioned embodiment, other inorganic materials could be used in place of, or in addition to, hydroxyapatite. These materials include tri-calcium phosphate, fluorapatite, carbonated hydroxyapatite, coralline hydroxyapatite, mineralized bone matrix, demineralized bone matrix, chlorapatite, bone meal powder, calcium sulfate, and bioactive glass (Bioglass). In an envisioned embodiment, hydroxyapatite is used with tri-calcium phosphate at a mass ratio ranging from 1:10-10:1, preferably 1:5-5:1, more preferably 1:4-4:1 hydroxyapatite to tri-calcium phosphate.

In one embodiment the porous scaffold structure is made with an additional biodegradable polymer of gelatin, lignin, poly(2-hydroxyethyl methacrylate), polyhydroxobutyrate, hyaluronic acid, a polysaccharide such as starch, dextran, sodium alginate, carboxymethyl cellulose (CMC) or hydroxypropyl methylcellulose (HPMC), chitosan, glycosaminoglycan, poly lactic-co-glycolic acid, poly lactic acid, poly glycolic acid, polyanhydride, poly(ortho)ester, polyurethane, poly(butyric acid), poly(valeric acid), polycaprolactone, poly(lactide-co-caprolactone), or poly(trimethylene carbonate). Any mixtures of these biodegradable polymers may also be used.

Preferably, the biodegradable polymer is poly lactic-co-glycolic acid, poly lactic acid, poly glycolic acid, polyanhydride, poly(ortho)ester, polyurethane, poly(butyric acid), poly(valeric acid), polycaprolactone, poly(lactide-co-caprolactone), or poly(trimethylene carbonate). In one preferred embodiment, the biodegradable polymer is poly lactic-co-glycolic acid.

Following the setting of the tannin-hydroxyapatite resin, the porogen is removed by dissolution, melting, evaporation, and/or sublimation, leaving a solid porous scaffold. Porogens that can be used in the tannin-hydroxyapatite resin include salt crystals, such as NaCl, $MgCl_2$, $CaCl_2$, $NH_4Cl$, $NH_4PO_4$, or $NH_4CO_3$; polysaccharides such as amylose, cellulose, cellulose derivatives, chitin, chitosan, dextran, glycogen, inulin, glycosaminoglycans, pectin, pullulan, starch, starch derivatives, or xanthan; monosaccharides such as glucose, ribose, fructose, or triose; saccharide oligomers; polymers including, but not limited to the aforementioned biodegradable polymers; waxes such as animal waxes, vegetable waxes, mineral waxes, petroleum waxes, synthetic waxes or mixtures thereof; and surfactants such as cationic surfactants (based on quaternary ammonium cations), anionic surfactants (based on sulfate, sulfonate, or carboxylate anions), zwitterionic (amphoteric) surfactants, or non-ionic surfactants. Particles of these porogens may comprise a mixture of different porogen compounds and can be added to the powder mixture, or they can be added to the liquid resin prior to setting. Following the formation of the solid scaffold, the porogens can be removed by dissolving in different solutions and/or heating the scaffold. The porogen particles may have an average largest dimension of 50-800, preferably 75-700, more preferably 100-600 μm. Preferably the porogen comprises dry, solid particles of polyethylene glycol with the polyethylene glycol having an average molecular weight of 1,000-100,000 Da, preferably 5,000-80,000 Da, more preferably 10,000-40,000 Da. It may be possible that the porogen creates pores in the resin by adsorbing to the surface of the dried tannin particles, which limits the amount of tannin available to react. Following the removal of the porogen, in one embodiment, the porous scaffold structure consists of the tannin-hydroxyapatite resin.

A crystal growth inhibitor may be added to the powder mixture to prevent the formation of hydroxyapatite crystals. Such inhibitors may be 1-hydroxyethylidene 1,1-diphosphonic acid (HEDP), nitrilotri (methylene phosphonic acid) (NTMP), ethylenediamine tetra(methylene phosphonic acid) (EDTMP), citric acid, disodium pyrophosphate, or tetrasodium pyrophosphate. More than one inhibitor can be used at once; preferably the inhibitors used are citric acid and disodium pyrophosphate. The combined mass of the crystal growth inhibitors added to the powder mixture may make up 0.5-5% total mass, preferably 1-4% total mass, more preferably 2.5-3.5% total mass of the powder mixture. In an embodiment using two crystal growth inhibitors, the mole ratio between them may range from 10:1-1:10, preferably 5:1-1:5, more preferably 3:1-1:3. In a preferred embodiment, disodium pyrophosphate is added to compose 0.1-3.5 wt %, preferably 0.5-2 wt %, more preferably 0.8-1.5 wt % of the powder mixture, and citric acid is added to compose 1-5 wt %, preferably 2-4 wt %, more preferably 2.2-3 wt % of the powder mixture.

The powder mixture is mixed with a volume of 0.10-0.40 mL, preferably 0.15-0.35 mL, more preferably 0.20-0.30 mL of an organic acid per gram of the powder mixture and a formaldehyde solution to form a liquid mixture. The concentration of organic acid added to the powder may range from 0.1-1 M, preferably 0.3-0.8 M, more preferably 0.4-0.6 M. The organic acid may be formic, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and/or isethionic acid; preferably the organic acid is citric acid.

The formaldehyde solution may be added to make up 1-20 wt %, preferably 2-18 wt %, more preferably 5-15 wt % of the liquid mixture. The formaldehyde solution may contain 20-38 wt %, preferably 30-38 wt %, more preferably 35-38 wt % formaldehyde. The formaldehyde solution may also include an alcohol at a weight concentration of 5-15%, preferably 7-13%, more preferably 8-12% to prevent formaldehyde polymerization. This alcohol may be ethanol, methanol, t-butyl alcohol, 1-propanol, or isopropanol; preferably the alcohol is methanol. In a preferred embodiment, the formaldehyde solution contains 37 wt % formaldehyde and 10% methanol, and is otherwise known as formalin.

In alternative embodiments, different cross-linking reagents may be used instead of, or in addition to, formaldehyde to create the tannin resin. For example, a hydrolyzable tannin may be used with phenol and formaldehyde to create a tannin resin. In another embodiment, furfuryl alcohol, succinaldehyde, glutaraldehyde, malondialdehyde, phthalaldehyde and/or glyoxal may be used as crosslinking reagents. In addition, tannin could be polymerized into a polyurethane with an isocyanate reagent such as methylene diphenyl diisocyanate (MDI), toluene diisocyanate (TDI), isophorone diisocyanate (IPDI), and/or hexamethylene diisocyanate (HDI). An ethoxylated amine may also be used in the polyurethane-forming reaction. In another example, a tannin-based epoxy resin may be formed by reacting hydrolyzable or condensed tannins with epoxides such as diglycidyl ether, polyglycidyl ether, and/or epichlorohydrin.

The liquid mixture is mixed vigorously for 20 s-5 min, preferably 30 s-2 min, more preferably 30 s-1 min, and then transferred to molds. The molds may be made of any non-reactive substance, but preferably the molds comprise a flexible material such as silicone, rubber, or a plastic. The mixing may be accomplished with a blender, a turbula, a vortex mixer, a general laboratory mixer, or by manually shaking. Preferably, the mixing is accomplished with a turbula. After 3-10 min, preferably after 4-8 min, more preferably after 5-7 min of transferring the samples, the molds may be completely submerged in a saline buffer to expose the samples to the buffer. Alternatively, the saline buffer may be added to the mold to completely cover the sample. The saline buffer may be phosphate buffered saline (PBS), tris buffered saline (TBS), (4-(2-hydroxyethyl)-1-piperazineethanesulfonic acid (HEPES) buffered saline, 3-(N-morpholino)propanesulfonic acid (MOPS) buffered saline, or Dulbecco's phosphate buffered saline (DPBS). Preferably, the buffer is DPBS with calcium. The saline buffer may be supplemented with a soluble calcium salt, such as $CaCl_2$, to a concentration of 0.5-1.3 mM, preferably 0.7-1.1 mM, more preferably 0.8-1.0 mM $Ca^{2+}$ in solution. The samples are incubated in the saline buffer for 12-48 h, preferably 18-36 h, more preferably 20-30 h and at a temperature of 30-50° C., preferably 34-42° C., more preferably 35-40° C. to allow for complete setting of the tannin-hydroxyapatite resin.

Then the samples are removed from the molds, optionally polished with a coated abrasive, such as sandpaper, and incubated in a saline buffer, such as those listed previously, for 24-96 h, preferably 36-60 h, more preferably 44-52 h, and at a temperature of 50-95° C., preferably 55-80° C., more preferably 65-75° C., to melt and leach the polyethylene glycol porogen particles, leaving a porous scaffold. It is conceivable that the minimal time and temperature required for porogen leaching may depend on the thickness and density of the resin sample. In an envisioned embodiment with a different type of porogen, the leaching step may not be done in an aqueous environment but in a solvent or a dry oven. In another envisioned embodiment, porosity may be introduced by a foam blowing agent, such as pentane, isopentane, cyclopentane, diethyl ether, and/or supercritical $CO_2$, instead of a porogen. In another embodiment, instead of a non-reactive porogen, a reactive substance could be mixed into the resin to produce gas bubbles in the structure. In yet another embodiment, porosity may be introduced to the scaffold structure by omitting a porogen substance and instead using larger spray-dried tannin particles in the powder mixture. These larger spray-dried tannin particles may have an average largest dimension of at least 100 μm, preferably at least 125 μm, more preferably at least 150 μm.

Depending on the concentration and type of porogen used, a small subset of pores might not be interconnected, meaning that their interior surface does not connect with the exterior surface of the scaffold structure. Preferably at least 95% of the pores are interconnected, more preferably at least 98%, even more preferably at least 99%.

Following the porogen leaching step of the tannin-hydroxyapatite resin, the sample may be dried for 10-48 h, preferably 12-24 h, more preferably 14-20 h at a temperature of 50-95° C., preferably 55-80° C., more preferably 65-75° C. Following the drying, the sample may be sterilized for cell culture by autoclaving at 150° C. for 30 min, however, other autoclave cycles or sterilization methods may be used, such as gamma ray sterilization. In one embodiment, the scaffolds are submerged in an aqueous solution of at least 70 vol %, at least 80 vol %, at least 90 vol % alcohol (e.g. methanol, ethanol, isopropanol, etc.) overnight to sterilize. Following sterilization, aseptic techniques may be used to prevent contamination of the bone graft.

In another embodiment, osteoinductive biomolecules are adsorbed or chemically-linked on the surface of the porous scaffold structure before adding the cells. The biomolecules may be mixed directly into the liquid mixture so that they may be exposed on the scaffold surface. The biomolecules may instead be chemically linked to a polymer on the scaffold surface, or linked to a polymer that had been mixed into the liquid mixture while forming the tannin-hydroxyapatite resin. As used herein, the "surface" of the porous scaffold denotes connected interior and exterior surfaces. These biomolecules may assist in cell attachment, growth, or differentiation of the osteocompetent stem cells. Such biomolecules include collagen, laminin, nidogen-1, vitronectin, fibronectin, bone morphogenic protein, RGD tripeptide, and mixtures of biomolecules like those from bone marrow aspirate and Matrigel. Certain synthetic polymer coatings on the scaffold surface may also promote cell attachment and differentiation such as poly(methylmethacrylate) (PMMA), polycarbonate, and amine group-grafted polyethylene.

In the embodiment where the porous scaffold structure is part of a biocompatible bone graft, the scaffold structure may also be seeded with osteocompetent stem cells. Osteocompetent stem cells are stem cells that can differentiate into osteoblast and osteoclast cells. These osteocompetent stem cells may be derived from mammalian stem cell sources such as embryonic or fetal tissue, placental tissue, umbilical cord tissue or blood, menstrual blood, muscle, synovial membrane tissue, bone marrow, periosteum, dermal tissue, or adipose tissue. Preferably, the osteocompetent stem cells are derived from bone marrow, periosteum, dermal fibroblasts, or adipose tissue. The osteocompetent stem cells for use in the bone graft may be obtained from a primary source or from a cell bank.

The mammalian source of the stem cells may be *Homo sapiens sapiens, Pan troglodytes, Bos primigenius, Sus scrofa domesticus, Canis lupus familiaris, Felis calus, Rattus norvegicus, Mus musculus*, or *Equusferus caballus*. Preferably, the mammalian source may be *Homo sapiens sapiens*.

In one embodiment, at least 50%, preferably at least 60%, more preferably at least 70% of the osteocompetent stem cells express CD13, CD29, CD44, CD49e, CD73, CD81, CD90, CD105 and/or CD151, which are biomarkers typical of primary mesenchymal stem cells. More preferably, the biomarkers are CD13, CD29, CD44, CD90, and/or CD105. In a related embodiment, at least 50%, preferably at least 60%, more preferably at least 70% of the osteocompetent stem cells show negative expression of OCT4, SOX2, TRA-1-60, CD31, CD34, and/or CD45, which means that the osteocompetent stem cells are not pluripotent nor hematopoietic. It is possible that a mixture of stem cells could be sorted by flow cytometry to choose osteocompetent stem cells based on the expression of the biomarkers.

Following collection of osteocompetent stem cells, the cells may be seeded onto the scaffold in the presence of a liquid growth medium to make the biocompatible bone graft. The liquid growth medium may be based on common formulations such as DMEM or DMEM:F12, or the medium may be a completely specialized formulation. The medium may include common supplements not specific to osteocompetent stem cells such as fetal bovine serum (FBS), ROCK inhibitor Y-27632, 1-glutamine, sodium pyruvate, or antibiotics. To support the differentiation of the osteocompetent stem cells, the liquid growth medium may include additional supplements and growth factors including, but not limited to, platelet derived growth factor (PDGF), osteopontin, calcium, insulin-like growth factor (IGF-1), $\beta$-glycerophosphate, dexamethasone, ascorbic acid-2-phosphate, ascorbic acid, transforming growth factor $\beta$ (TGF-$\beta_1$), fibroblast growth factor (FGF), active vitamin D, a bone morphogenic protein (BMP), parathyroid hormone, or any combination thereof. Preferably, the supplement or growth factor is $\beta$-glycerophosphate, dexamethasone, ascorbic acid, transforming growth factor $\beta$ (TGF-$\beta_1$), fibroblast growth factor (FGF), active vitamin D, a bone morphogenic protein (BMP-2, BMP-4, or BMP-7), or parathyroid hormone. These growth factors may be added individually in a purified form to the liquid growth medium, or they may be added together with their biological source, such as platelet-rich plasma or bone marrow aspirate. In an envisioned embodiment, a growth factor or supplement may be adsorbed onto or chemically attached to the surface of the scaffold, as described previously with other biomolecules.

In a further embodiment, the cells prior to seeding may be grown within a 3D gel or other semi-solid, rather than a liquid growth medium.

Additionally, the composition of the growth medium may be altered at any point prior to implanting the bone graft. It is likely that in the steps from expanding the stem cell population in a flask to seeding the cells on the scaffold, different growth media may be used to supply different types and concentrations of nutrients to the cells.

Additionally, depending on the number of cells and the size of the scaffold, the cell population may need to be expanded prior to seeding on the scaffold. In some cases, the cells may be seeded on the scaffold, and then grown on the scaffold before implanting the bone graft. Cells may be added to one side of the scaffold if the scaffold is relatively small.

Additionally, for larger scaffolds, cells may be added to more than one side. Also, the scaffold may be intermittently rotated or flipped to encourage cell growth throughout the porous structure. The scaffold may be partially submerged in liquid growth medium or completely submerged. In the case of a partially submerged scaffold, liquid growth medium may periodically be added to the unsubmerged portion to keep the cells from drying out.

In one embodiment, a cryopreservative liquid medium may be added to the bone graft. The cryopreservative liquid medium may include FBS and a cryoprotectant such as glycerol and/or DMSO, or the medium may be a proprietary formulation available commercially. When stored at a temperature of −75 to −85° C., the bone graft may be preserved up to 5 years. When stored in a liquid nitrogen vapor phase, the bone graft may be preserved indefinitely.

The present disclosure also relates to a method of regenerating bone in a patient by implanting the aforementioned biocompatible bone graft within a bone wound site in a patient.

The bone wound site may be a defect resulting from injury such as a transverse fracture, a linear fracture, an oblique fracture, a spiral fracture, a greenstick fracture, or a comminuted fracture; from surgery; from an infection such as osteomyelitis; from malignancy, such as osteoma, osteoid osteoma, osteochondroma, osteoblastoma, osteoblastoma, enchondroma, aneurysmal bone cyst, giant cell tumor of the bone, chondrosarcoma, fibrus dysplasia, osteosarcoma, fibrosarcoma, or Ewing sarcoma; or from a developmental malformation such as a metaphyseal defect. The bone wound site may be in cancellous or cortical bone, or in a single bone wound site that comprises both. The bone wound site may also result from a previous bone graft that became infected or otherwise failed to heal.

In one embodiment of the method, the patient is the mammalian donor, wherein the bone graft is an autograft by definition. In a related embodiment, the bone graft is an allograft, in which the patient and the donor are different organisms, but the same species. In another related embodiment, the bone graft is a xenograft, in which the patient and the donor are different species.

In another embodiment, the bone graft is implanted with a prosthesis, such as a tooth, a knee, a shoulder, or a hip. The bone graft may also be implanted with an orthopedic implant to support an existing bone or joint, or to replace, in whole or in part, a missing bone or joint. Such orthopedic implants may comprise pins, rods, screws, nails, wires, and plates, and may be made of biocompatible metals such as titanium and related alloys, cobalt-based alloys, or stainless steel, or biocompatible polymeric materials such as carbon fiber, high density polyethylene, ultra-high molecular weight polyethylene (UHMWPE), polymethylmethacrylate (PMMA), or thermoplastic polyether ether ketone (PEEK).

In one embodiment of the method, a second bone graft is implanted into the implant site. This second bone graft may be identical to the first, or it may have a different size and/or composition. Where the implant site is shaped too irregularly or is too large for the insertion of a single bone graft, multiple, smaller bone grafts may be inserted. These smaller bone grafts may be shaped for specific locations in the bone wound sites and may require a certain order of insertion. In contrast, the bone grafts may be at a scale much smaller than the bone wound site in which case they can fill the bone wound site in any order or placement.

In addition, the porous scaffold could be broken into small pieces that are combined with osteocompetent stem cells and a growth medium to form a semi-solid bone graft paste. This paste could fill both regular and irregularly-shaped bone wounds as an alternative to implanting a solid scaffold structure. In this embodiment, a porogen may not be required in the tannin-hydroxyapatite resin, nor would the resin need to set in a mold. Depending on the viscosity, the bone graft paste may be injected into a bone wound site using a syringe. In a further embodiment, the bone graft paste could be used to support or surround a larger intact bone graft or other implant in the center of a bone wound site.

In one embodiment, the second bone graft comprises a macroporous hydroxyapatite-tannin resin but has a different composition, which may encourage bone development at different rates within the bone wound site. For example, the second bone graft may have a different porosity or a different composition of hydroxyapatite, polymers, tannins, and/or osteoinductive biomolecules. The second bone graft may have a different compressive strength or biodegrade a rate different than the first bone graft.

In another embodiment, the second bone graft is different than the first bone graft in that the second bone graft contains mineralized osseous tissue from a mammalian donor. This mineralized osseous tissue may be from cancellous and/or cortical bone, and may or may not contain cells. Preferably, this mineralized osseous tissue is fragmented into a paste as described previously. The donor of the osseous tissue may be a member of a different species than the patient, or may be a member of the same species as the patient, or may be the patient. In a related embodiment, a bone graft may be implanted with other living tissues such as cancellous bone marrow.

In one embodiment, a previously described growth factor may be added to the bone wound site when implanting the bone graft. Additionally, the growth factor may be administered by oral administration, intravenous administration, topical administration, intradermal administration, transdermal administration, subcutaneous administration, intramuscular administration, intralesional administration, intrapulmonal administration, or sublingual administration. The growth factor may be administered prior to, during, or after the grafting surgery, or at any combination of those times, and likely, more than one type of growth factor may be administered. The growth factor may also be administered with an analgesic or anti-inflammatory drug.

In one embodiment the tannin-hydroxyapatite resin of the biocompatible bone graft degrades into inert products that can be resorbed in a bone graft implant site. In that case, the growth and differentiation of the osteocompetent stem cells breaks down the scaffold structure into biocompatible products. Preferably, this process occurs as newly-developed osteoblasts lay down bone tissue, leading to the eventual replacement of the scaffold structure with mature bone tissue. It is conceivable that the hydroxyapatite embedded in the scaffold structure could be used by the osteoblasts in mineralizing new bone tissue. It is also possible that the tannin resin may be broken down into dissolved constituent polyphenolic molecules that are either metabolized by neighboring cells or are left in the extracellular space of the tissue.

According to a second aspect, the present disclosure relates to a method of monitoring the growth of the osteocompetent stem cells in the biocompatible bone graft up to 16 weeks by medical imaging, such as X-ray imaging, MRI, or ultrasonography. It is envisioned that the growth and bone formation within the bone graft create changes in density which can be detected by either of these imaging modes over a certain length of time. An increase in density may occur where osteoblast and osteoclast cells populate the scaffold and create new bone tissue. A decrease in density may occur where the scaffold is degraded. Likely, a single bone graft site may have both increases and decreases in density, occurring at different places and/or at different times. To monitor the growth of the osteocompetent stem cells, it is envisioned that two sets of images recorded with the same imaging mode but at different time intervals may be compared with one another. Likely, more than two sets of images may be compared, and for certain bone wound sites, longer healing times may warrant images recorded up to 6 months following the implant surgery. To ensure healing of the bone wound site, treatment may be modified depending on the progression of growth, such as the amount of activity allowed to the patient, the types of drugs administered, or the removal of sutures, casts, or braces. For example, if a drug is administered to support bone remineralization, the dosage may be decreased when a sufficient amount of new bone tissue has formed within the bone graft.

In another embodiment of the method, the growth of the osteocompetent stem cells are monitored up to 16 weeks by the expression level of one of the following osteogenic differentiation genes: BGLAP, BMP-2, BMP-4, BMP-6, BMP-7, SP7, RUNX2, COL1A1, ALPL, OPN, or PDGFRB. Preferably the gene is RUNX2, COL1A1, ALPL, OPN, or PDGFRB. Preferably, the expression level of the gene is inferred by measuring the concentration of its mRNA and comparing that to the mRNA concentration of a housekeeping gene, such as GAPDH. For these measurements, a tissue sample may be taken from the bone graft, preferably by a needle biopsy. Following routine protocol to extract and purify the mRNA, the concentration may be determined through quantitative RT-PCR. Preferably, more than one osteogenic differentiation gene is measured. To track the differentiation of the cells, the mRNA levels may be compared between two sets of measurements taken at different times. The first set of measurements may be prior to seeding the stem cells on the scaffold, or prior to implanting the bone graft. When the first set of measurements is taken prior to implanting the bone graft, the second set of measurements may be taken via biopsy at least one week, preferably at least 1 month, more preferably at least 2 months following the bone graft implant surgery. Given a larger than average bone wound site, it is likely that mRNA levels may depend on the location where the sample is taken. It is further envisioned that to improve growth conditions in vitro, the osteogenic differentiation genes may be measured of a bone graft that is not intended to be implanted.

According to a third aspect, the present disclosure relates to a method of screening a bone disease drug by adding the drug to the growth medium of the biocompatible bone graft, growing the osteocompetent stem cells in the presence of the drug to form new bone tissue on the bone graft, measuring the porosity, density, and/or compressive strength of the drug-treated bone graft, and comparing it to a substantially similar bone graft that has not been treated with the drug. Bone disease drugs that affect the growth of bone tissue may change measurable properties of the bone graft, and these properties may be measured ex vivo and compared to a similar untreated bone graft. As bone tissue is developed in the bone graft, the density may increase while the porosity decreases. The compressive strength may increase or decrease at different times, depending on the rate of resin scaffold degradation versus bone tissue growth and mineralization. It is envisioned that for implanted bone grafts, biopsies are taken to provide a representative composition of tissue and scaffold material. Bone graft samples obtained by biopsies or other means may be fixed with a formaldehyde solution prior to measurement in order to secure cells and tissue within the porous scaffold. Porosity and density may be characterized by drying the scaffold and measuring with gas displacement pycnometry, mercury intrusion porosimetry, or micro-CT (micro-computed tomography, or μCT). The compressive strength may be measured with an ultrasonic cement analyzer or a more general compressive strength tester.

In the case where the bone graft is implanted into a patient, the bone disease drug may be administered by any of the aforementioned methods for growth factors.

In one embodiment, the bone disease drug is ipriflavone, incadronic acid, pamidronic acid, clodronic acid, tiludronic acid, denosumab, teriparatide, alendronate, risedronate, ibandronate, zoledronic acid, teriparatide, strontium ranelate, aluminium chlorohydrate, or odanacatib. Preferably, the bone disease drug is denosumab, teriparatide, alendronate, risedronate, ibandronate, zoledronic acid, teriparatide, strontium ranelate, aluminium chlorohydrate, or odanacatib.

In a preferred embodiment, the growth of the new bone tissue within the drug-treated bone graft and the untreated bone graft occurs in vitro. In this embodiment, the two bone grafts can be compared side-by-side. It is also envisioned that several bone grafts could be grown in vitro to systematically test different drugs or growing conditions. Media supplements and growth factors, as listed previously, may also be used.

The examples below are intended to further illustrate protocols for preparing and characterizing the biocompatible bone graft, and uses thereof, and are not intended to limit the scope of the claims.

EXAMPLE 1

Experimental Setup
Scaffold Fabrication

Porous tannin spray-dried powder (PTSDP) was mixed with hydroxyapatite ($Ca_{10}(PO_4)_6(OH)_2$) to form a powder mixture with a composition of 80 wt % PTSDP and 20 wt % hydroxyapatite, prepared as previously detailed [Amaral-Labat, G. et al., Highly mesoporous organic aerogels derived from soy and tannin, Green Chem., 2012, 14, 3099—incorporated herein by reference in its entirety]. Then, the powder mixture was sieved to include only 25-75 μm diameter particles. Polyethylene glycol (PEG; 20,000 MW, Sigma, St. Louis Mo.) was melted at 100° C., then solidified at room temperature and ground to a fine powder. The milled powder was sieved to defined size ranges of 100-400, 400-600, or 100-600 μm. The PEG powder at a certain size range was added directly to the tannin-hydroxyapatite powder at a weight ratio of 0.4, 0.6, 0.8 or 1 gram of PEG powder per gram of tannin-hydroxyapatite powder, and mixed together in a turbula for 30 min. Crystal growth inhibitors disodium dihydrogen pyrophosphate (1% by weight) and citric acid (2.4% by weight) were added directly to the powder, along with a formalin solution (10% by weight). The macroporous scaffolds were fabricated by addition of a citric acid solution (0.5M) to the powder at a ratio of 0.25 mL per gram of powder (irrespective of the amount of PEG). The mixture was shaken in a cap mixer for 1 minute and immediately manually transferred to silicone molds (8 mm diameter×3 mm thick) using a spatula. Within 5-7 min the molds were transferred to Dulbecco's phosphate buffered saline with calcium (DPBS-8662, Sigma) to allow for complete setting at 37° C. for 24 h.

Then, the samples were removed from the molds, polished with sandpaper to about 2 mm thickness, and transferred to fresh DPBS-8662 at 70° C. to melt and leach the PEG for 48 h. The absence of PEG was confirmed by differential scanning calorimetry (DSC) and X-ray diffraction analysis (XRD) as described below. Each sample was dried at 70° C. for 16 h, then sterilized in an autoclave at 150° C. for 30 min and used for characterization and cell culture. Ten scaffold groups were thus manufactured as listed in Table 1. Bone disks were prepared as previously described [de Peppo G. M., et al., Engineering bone tissue substitutes from human induced pluripotent stem cells, Proc Natl Acad Sci USA. 2013, 110, 8680—incorporated herein by reference in its entirety]. Plugs of trabecular bone (8 mm diameter) were drilled from the subchondral region of meta-carpal joints of calves (Green Village Packing, Green Village, N.J.). Soon after, plugs were cleansed under a high-pressure water stream to remove the bone marrow and then sequentially washed with a solution of ethylenediamine tetra-acetic acid (EDTA) (0.1%) in DPBS-8662, then EDTA (0.1%) in Tris (10 mM), then SDS (0.5%) in Tris (10 mM), followed by treatment with a solution of DNase and RNase in Tris buffer (10 mM) to remove cellular material. Decellularized bone plugs were thoroughly rinsed in DPBS-8662, freeze-dried, cut, and then polished to about 2 mm thickness. Each individual scaffold was weighed and measured to calculate the density, and those in the range of 0.27-0.35 $g/cm^3$ were used for material characterization analysis and cell culture. For cell culture, scaffolds were selected and sterilized overnight in ethanol (70% by volume) and then conditioned in expansion medium overnight.

TABLE 1

| Group | PEG content (g/g of cement) | PEG particle size (μm) |
|---|---|---|
| Control | 0 | NA |
| 1 | 0.4 | 100-400 |
| 2 | 0.4 | 100-600 |
| 3 | 0.6 | 100-400 |
| 4 | 0.6 | 100-600 |
| 5 | 0.6 | 400-600 |
| 6 | 0.8 | 100-400 |
| 7 | 0.8 | 100-600 |
| 8 | 0.8 | 400-600 |
| 9 | 1.0 | 100-600 |
| B | NA | Bone |

SEM Analysis

PSDTP and decellularized bone scaffolds were imaged on a Hitachi TM100 scanning electron microscope (Hitachi High Technologies America Inc, Schaumburg, Ill.). Three random fields, from three samples per group, were photographed using the following settings: 15 kV, 100× magnification, and 7 mm working distance.

Material Composition Analysis

X-ray diffraction and Rietveld analysis were used to assess the material composition after the manufacturing process. Briefly, the ground powder from autoclaved tannin-hydroxyapatite scaffolds was analyzed using a C8 advanced Bruker diffractometer (Bruker Corporation, Billerica, Mass.), theta-theta setup at 40 kV and 40 mA and over diffraction angles of 5-60°. The step length was 0.3 seconds per step, with 0.01 degrees per step and a rotation speed of 80 rotations per minute (rpm). Open source software Profex (http://profex.doebelin.org) was used to quantify the spectra via Rietveld refinement. The reported values are the average of 3 readings for each group. Complete removal of PEG from leached scaffolds was confirmed by the lack of PEG peaks at the angles of 19.23° and 23.24° for samples for each group.

For differential scanning calorimetry, cylinders 8 mm in diameter and 3 mm thickness were prepared for cell culture and during the leaching process samples were removed after 2.5, 24, 32, or 56 h of leaching, and dried for 2 h at 25° C. Three samples from each group were ground to a fine powder and 10-20 mg of powder was heated from 25° C. to 120° C., at 10° C. per minute, in a TA Q2000 DSC (TA Instruments, New Castle, Del.). Then, the total enthalpy change for each sample was calculated and compared to tannin-hydroxyapatite powders containing a known amount of PEG, and data were exported to graphing software Origin (OriginLab Corporation, Northampton, Mass.).

Porosity Measurement

The porosity of tannin-hydroxyapatite and decellularized bone scaffolds was determined with the Acupyc 1330 helium pycnometry (Micrometrics, Norcross, Ga.). Six samples were ground to a fine powder with mortar and pestle and the skeletal density ($\rho_s$) of the powder determined by helium gas intrusion, using a 1 cm$^3$ chamber at 19.5 pounds per square inch of pressure. Samples were first dried completely and the apparent density ($\rho_a$) was determined by measuring the physical dimensions of each specimen with calipers. Following Unosson et al., the total porosity (5%) of samples was determined according to the following equation [Unosson, J. E., et al., An evaluation of methods to determine the porosity of calcium phosphate cements, *Biomed. Mater. Res. B Appl. Biomater.*, 2015, 103, 62—incorporated herein by reference in its entirety]:

$$\Phi \% = \left(1 - \frac{\rho_a}{\rho_s}\right) * 100 \quad (1)$$

The macroporosity was calculated for each group by substituting the average apparent density of the control group composites (no PEG) for the skeletal density in equation (1).

Micro-computed Tomography (μCT)

Micro-CT was used to assess the 3D microstructure of tannin-hydroxyapatite and decellularized bone scaffolds (Skyscan 1172, Bruker, Kontich, Belgium). Samples were acquired using: source voltage of 100 kV, a current of 100 μA, and an isotropic pixel size of 10 μm$^2$. Reconstruction of cross sections was done using the NRecon software package (SkyScan, Bruker, Kontich, Belgium). The reconstructed images were binarized using an optimized global threshold and structural analyses were done in the CTAn software package (SkysScan, Bruker, 3 Kontich-Belgium). Three-dimensional reconstructions of the samples were obtained using CTvox (SkyScan, Bruker, Kontich, Belgium). Five samples were analyzed for each synthetic scaffold group, and 30 bone disks were imaged to account for high sample-to-sample variability associated with biological samples.

Compressive Strength

Tannin-hydroxyapatite resin scaffold samples were fabricated in molds 6 mm diameter×13 mm in length, allowed to set for 24 h and the top and bottom faces were polished to a final length of 12 mm. After subsequently leaching for 48 h at 70° C., 6 mm×12 mm cylinders were autoclaved. The dimensions were recorded with calipers, and the samples were compressed to failure on a Shimadzu autograph AGS-X at 1 mm/min. Analysis software TrapeziumX (Shimadzu, Tokyo, JP) was used to record and analyze data. Decellularized bone scaffolds were compressed to failure at 1 mm/minute. Each group contained 5 samples.

Cell Culture and Characterization

Following Hua et al., [H. Hua, et al., iPSC-derived β cells model diabetes due to glucokinase deficiency, *J Clin Invest.*, 2013 July; 123, 3146—incorporated herein by reference in its entirety], human iPSC line 1013A was generated from dermal fibroblasts obtained from healthy individuals using sendai virus, according to the previously published protocols [Nagamura-Inoue, T. et al., Umbilical cord-derived mesenchymal stem cells: Their advantages and potential clinical utility, *World J Stem Cells*, 2014, 6, 195—incorporated herein by reference in its entirety] and expanded on mouse embryonic fibroblasts. Prior to mesenchymal differentiation, cells were evaluated for the expression of pluripotency markers. Briefly, cultures were fixed in 10 vol % formaldehyde solution, permeabilized using 0.1% Triton X-100 in DPBS-8662 (DPBS-8662T), blocked with 10% (by volume) donkey serum (Jackson ImmunoResearch Laboratories Inc, West Grove, Pa.) in DPBS-8662T and incubated overnight with primary antibodies (all from STEMGENT, Cambridge, Mass.) against Oct-4 (2.5 μg/mL; cat no. 09-0023), Sox2 (2.5 μg/mL; cat no. 09-0024), and TRA-1-60 (2.5 μg/mL; cat no. 09-0010). Alexa Fluor® secondary antibodies (all from Life Technologies, Waltham, Mass.) were used for detection (2 μg/mL; cat no. A31571, A11057 and A21206), and the nuclei were counterstained with Hoechst 33342 (1:1000 dilution; Life Technologies, Carlsbad, Calif.). Negative control samples were generated omitting the primary antibodies. Fluorescence images were taken with an Olympus IX71 mounted with a Q-Color 3 imaging camera and controlled by Olympus DP-BSW software. Images were processed with ImageJ (National Institutes of Health), and all fluorescence images are represented with pseudo-colors.

Confluent cultures of 1013A at passage 18 (P18) were then coaxed toward the mesenchymal lineage in the presence of induction medium as previously described [Nagamura-Inoue, T. et al., Umbilical cord-derived mesenchymal stem cells: Their advantages and potential clinical utility, *World J Stem Cells*, 2014, 6, 195—incorporated herein by reference in its entirety] and derived mesenchymal progenitors (1013A-MP) were expanded to P4 on EmbryoMax® gelatin (0.1%; Millipore, Billerica, Mass.)-coated plasticware in medium consisting of KnockOut Dulbecco's Modified Eagle's Medium (KO-DMEM) supplemented with 20% (by volume) HyClone fetal bovine serum (FBS; Thermo Scientific, Waltham, Mass.), 2 mM GlutaMax, 0.1 mM nonessential amino acids, 0.1 mM β-mercaptoethanol, and 100 U/mL penicillin-streptomycin (all from Life Technologies).

For immunohistochemistry, cell suspensions (25×10$^3$ cells in 200 μL DPBS-8662) were spun using the Cytospin 4 (Thermo Scientific) at 1000 rpm for 5 min on SUPERFROST® microscope slides (Thermo Scientific), fixed with 4% PFA for 20 min at room temperature, washed in DPBS-8662, and immunostained for Oct-4, Sox-2, and TRA-1-60 as described before. Nuclei were counterstained with Hoechst 33342 (Sigma). Fluorescence images were taken with an Olympus 1X71 and processed with ImageJ (NIH). All fluorescent images are represented in pseudo-colors.

For flow cytometry analysis, cells were enzymatically detached with trypsin/EDTA (0.25%), filtered through a 70 μm cell strainer (BD Biosciences, Franklin Lakes, N.J.) to obtain a single cell suspension and centrifuged at 1000 rpm for 5 min. Cells were then re-suspended in staining buffer ($5 \times 10^5$ cells in 200 μL) consisting of DPBS-8662 containing 0.5% (by volume) bovine serum albumin fraction V (Invitrogen), 100 U/mL penicillin-streptomycin (Invitrogen), 2 mM EDTA (Invitrogen), and 20 mM glucose (Sigma), and stained with a panel of primary antibodies: phycoerythrin-conjugated CD13 (cat. no. 555394), CD29 (cat. no. 555443), CD34 (cat. no. 555822), CD45 (cat. no. 560975), CD49e (cat. no. 555617), CD81 (cat. no. 555676), CD90 (cat. no. 555596), CD151 (cat. no. 556057), Alexa Fluor® 647-conjugated CD31 (cat. no. 558094), fluorescein isothiocyanate-conjugated CD73 (cat. no. 561254) (all from BD Pharmingen, San Diego, Calif.), and phycoerythrin-conjugated CD105 (cat. no. 12-1057-42; eBioscience, San Diego, Calif.). Cells were incubated on ice for 30 min in the dark, followed by washing with staining buffer, and analyzed immediately on the ARIA-IIu™ SOU Cell Sorter (BD Biosciences) configured with a 100 μm ceramic nozzle and operating at 20 psi sheath fluid pressure. Data were acquired and analyzed using the Diva 6.0 software (BD Biosciences). Positive expression of surface markers was determined using isotype controls. Gates were set using 1% in negative controls.

Cultures were screened for *mycoplasma* using the Myco-Alert *Mycoplasma* Detection Kit (Lonza, Basel-CH). Briefly, culture media were centrifuged at 450×g for 5 min, the supernatants collected, and luminescence measured using the Synergy Mx microplate reader and Gen5 software (BioTek, Winooski, Vt.).

For cell seeding and culture on scaffolds, cells were detached at P4 using trypsin/EDTA (0.25%), counted, and suspended in expansion medium at a density of $30 \times 10^6$ cells/mL, and a 40 mL aliquot of the cell suspension was pipetted onto the blot-dried scaffolds in Costar® six-well ultra-low attachment plates (Corning, Corning, N.Y.). For tannin-hydroxyapatite scaffolds Group 1 and 6, two seeding protocols were used in the attempt to increase the yield of attached cells. In protocol 1, a 20 mL aliquot of cell suspension was added on one scaffold side and after 30 min the scaffolds were flipped and an additional 20 mL aliquot of cell suspension was added. Following 30 min, the scaffolds were flipped every 15 min for 2 h, and each time 5 μL of medium was added to avoid drying. In protocol 2, a 20 mL aliquot of cell suspension was added on one scaffold side and then incubated for 1.5 h. Every 15 min, 5 μL of medium was added to avoid drying. The scaffolds were then flipped, a 20 mL aliquot of cell suspension was added, and then the constructs (i.e. bone grafts) were incubated for an additional 1.5 h as described above. For decellularized bone scaffolds, the 40 mL aliquot was pipetted only on one side and every 15 min for 2 h, the scaffolds were flipped to facilitate uniform cell distribution, and 5 μL of medium was added to prevent the cells from drying out.

Following seeding, constructs were incubated overnight in expansion medium and the medium was collected. Non-adherent cells were counted using disposable Kova® Glasstic® slides (Kova International, Garden Grove, Calif.). The amount of attached cells per construct was also estimated 1 day after seeding using the PrestoBlue™ assay (Life Technologies™, Frederick, Md.) and following the manufacturer's instructions. Briefly, 700 μL of osteogenic medium containing 10% of PrestoBlue™ reagent (by volume) was added to each construct and samples were incubated at 37° C. for 2 h. Then, a 200 μL aliquot was transferred to a black, clear, flat bottom 96-well Falcon™ plate (BD, Franklin Lakes, N.J.), and the amount of viable cells determined by measuring the fluorescence intensity at 560/590 nm (excitation/emission) using the Synergy Mx microplate reader and Gen5 software 1.09 (BioTek). Readings were corrected for background fluorescence using expansion media as a control. The constructs were cultured in expansion medium for 3 days and then in osteogenic medium [DMEM (Life Technologies) supplemented with 10% (by volume) HyClone FBS (Thermo Scientific), 1 μM dexamethasone (Sigma), 10 μM β-glycerophosphate (Sigma), 50 μM ascorbic acid-2-phosphate (Sigma) and antibiotic-antimycotic (1×; Life Technologies)] for 7 weeks. All cultures were screened for *mycoplasma* using the MycoAlert *Mycoplasma* Detection Kit (Lonza) as described above.

Cell attachment and survival was investigated via microscopic investigation using the LIVE/DEAD assay (Molecular Probes/Life Technologies). Briefly, constructs were washed in DPBS-8662 and incubated with a solution of calcein AM (2 μM) and ethidium bromide (4 μM) in DPBS-8662 for 1 h and imaged by epifluorescence and confocal microscopy in RPMI medium without red phenol (Lonza). Fluorescence images were taken with an Olympus IX71 as described above. In order to completely image each construct, mosaic pictures were assembled from sequential fluorescent images using ImageJ equipped with MosaicJ and TurboReg plugins (NIH). Confocal images were taken with the microscope Axiovert 200M microscope (Zeiss, Oberkochen, GE) mounted with an LSM 5 Pascal exciter using the LSM 5 Pascal software (Zeiss) under defined settings.

The osteogenic differentiation of 1013A-MP cells cultured on tannin-hydroxyapatite and decellularized bone scaffolds was explored via real-time PCR (RT-PCR) by measuring the expression of genes recognized to play a role during bone formation. After growing the cells for 3 or 7 weeks after seeding, 1 mL of TRIzol (Life Technologies) was added to each scaffold or decellularized bone. The cells were vortex-mixed 3 times (20 sec each) before adding 190 mL of chloroform for extraction. Following centrifugation at 12,000×g for 15 min at 4° C., the aqueous phase was collected, mixed with equal volume of 70% ethanol, and RNA extracted using the RNeasy Mini Kit (Qiagen, Venlo, Nebr.) as above. Purified RNA was quantified and reversely transcribed with random hexamers using the GoScript™ Reverse Transcription System (Promega, Madison, Wis.) according the manufacturer's protocol. RT-PCR was performed using the StepOnePlus PCR System cycler (Applied Biosystems, Waltham, Mass.) in a 20 μL volume reaction using the TaqMan Universal PCR Master Mix and TaqMan Gene Expression Assays (Life Technologies) composed of FAM dye-labeled TaqMan MGB probe and PCR primers for runt-related transcription factor 2 (RUNX2; Hs00231692_m1), collagen, type I, alpha 1 (COL1A1; Hs00164004_m1), alkaline phosphatase (ALPL; Hs01029144_m1), osteopontin (OPN; Hs00959010_m1), platelet-derived growth factor receptor beta (PDGFRB; Hs01019589_m1), and VIC dye-labeled TaqMan MGB probe and primers for the housekeeping gene glyceraldehyde 3-phosphate dehydrogenase (GAPDH, Hs02758991_g1). Cycling conditions were 95° C. for 10 min followed by 40 cycles of 95° C. for 15 s (denaturation) and 60° C. for 60 s (annealing and extension). The data were analyzed using the StepOne™ v2.2.2 software (Applied Biosystems), and the expression levels of the target genes were normalized to the expression level of GAPDH. The expression of genes of interest was expressed as the fold change over the expression at day zero, i.e. the day when culture in osteogenic media started.

Statistics

Statistical analysis was conducted using the GraphPad Prism 6 version 6.0e (GraphPad Software Inc, La Jolla, Calif.). Student's t-test was used for single comparisons between two groups. One-way or two-way ANOVA was used for multiple comparisons with a Bonferroni post-hoc test when Gaussian distribution was confirmed using the D'Agostino-Pearson or Shapiro-Wilk normality test. All results are shown as means and ±standard deviations. A difference between the mean values for each group was considered statistically significant when the p value was less than 0.05.

EXAMPLE 2

Results
Scaffold Topography and Chemistry

Figure 1A:
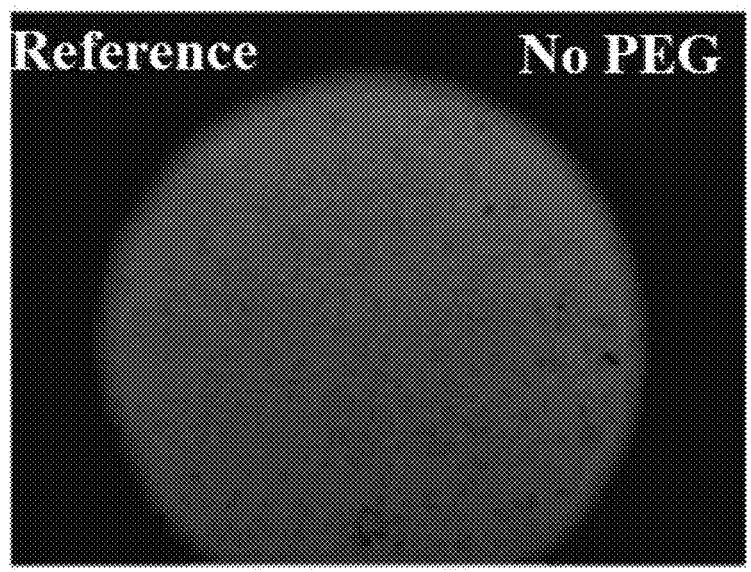
FIG. 1A is an SEM image of a reference scaffold structure made without PEG.
Figure 1B:
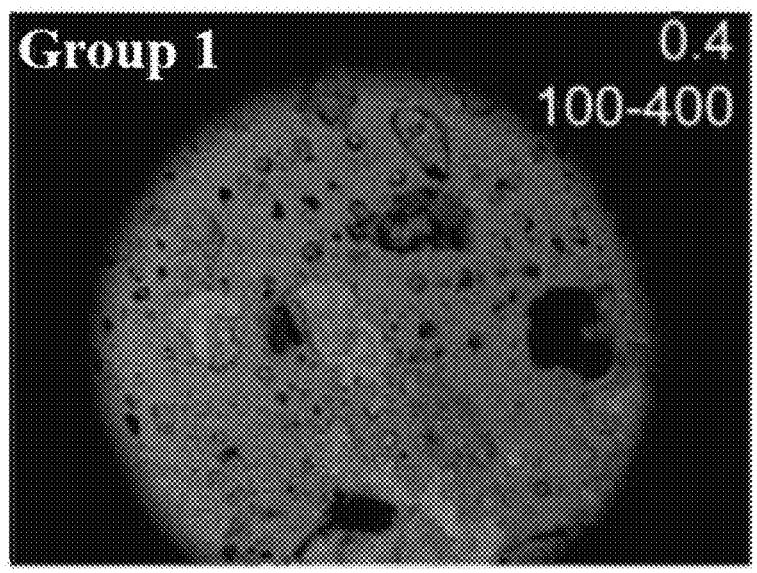
FIG. 1B is an SEM image of a Group 1 scaffold made with a 0.4 weight ratio of PEG:cement (tannin and hydroxyapatite) using 100-400 μm diameter PEG particles.
Figure 1C:
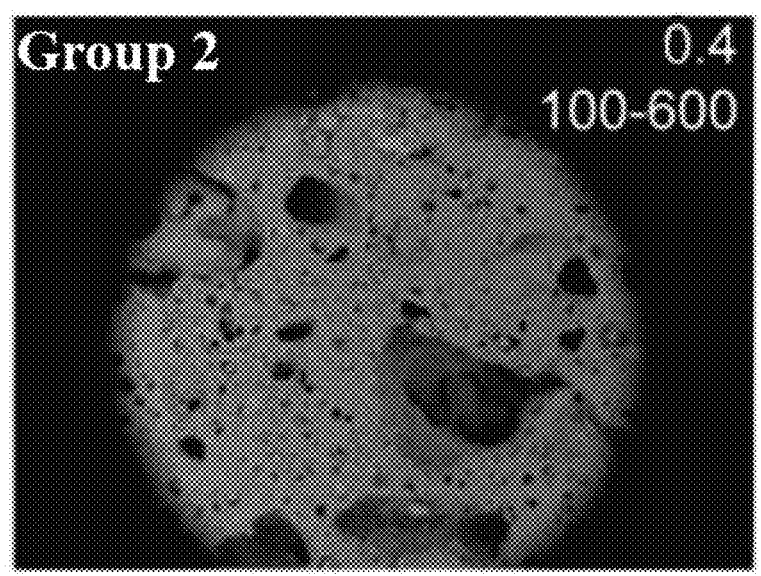
FIG. 1C is an SEM image of a Group 2 scaffold made with a 0.4 weight ratio of PEG using 100-600 μm diameter PEG particles.
Figure 1D:
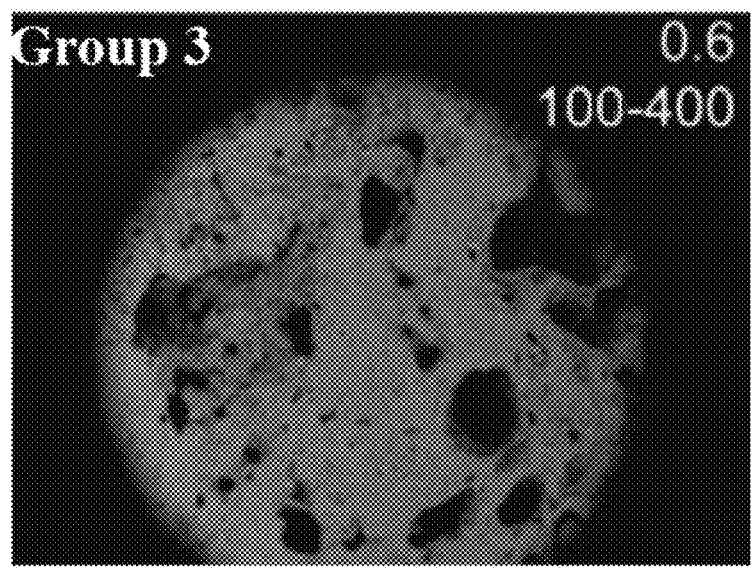
FIG. 1D is an SEM image of a Group 3 scaffold made with a 0.6 weight ratio of PEG using 100-400 μm diameter PEG particles.
Figure 1E:
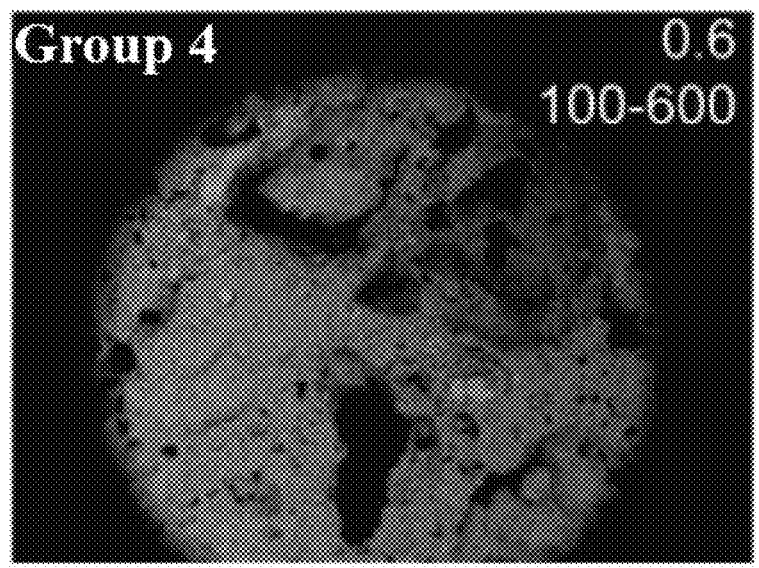
FIG. 1E is an SEM image of a Group 4 scaffold made with a 0.6 weight ratio of PEG using 100-600 μm diameter PEG particles.
Figure 1F:
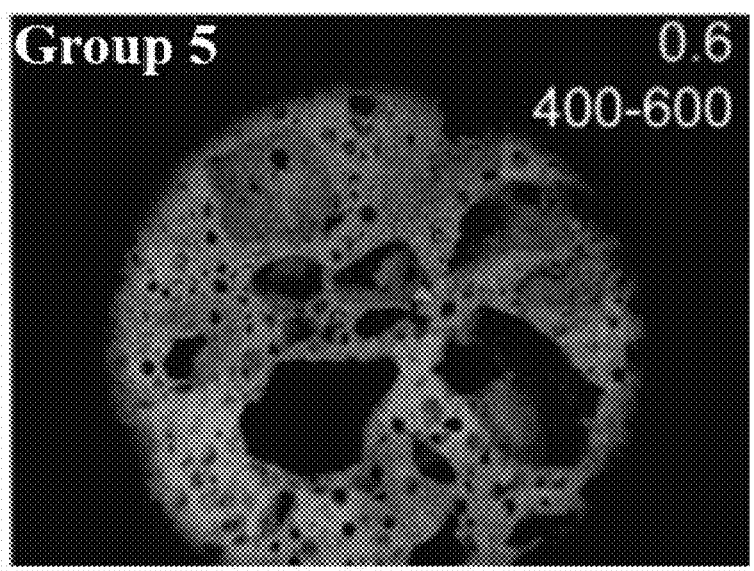
FIG. 1F is an SEM image of a Group 5 scaffold made with a 0.6 weight ratio of PEG using 400-600 μm diameter PEG particles.
Figure 1G:
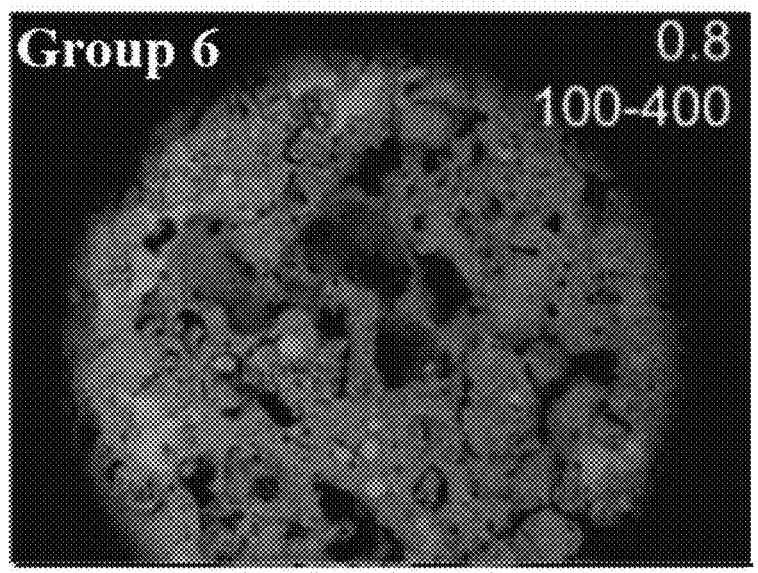
FIG. 1G is an SEM image of a Group 6 scaffold made with a 0.8 weight ratio of PEG using 100-400 μm diameter PEG particles.
Figure 1H:
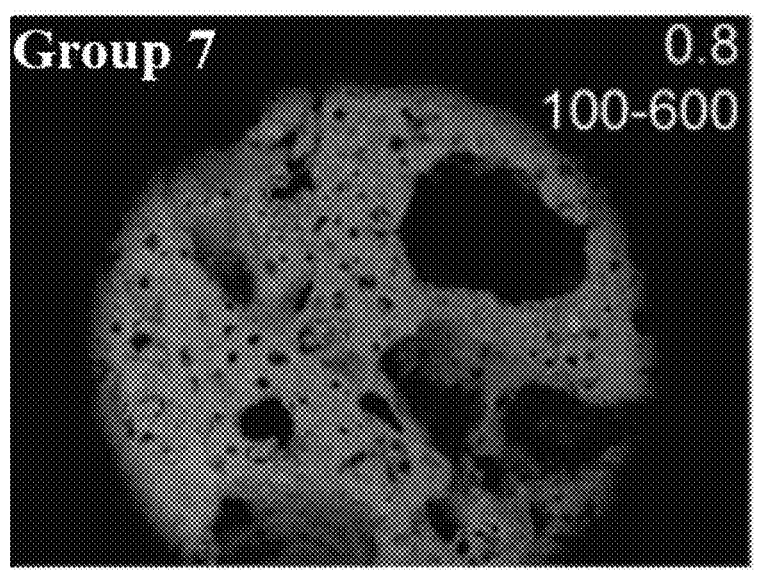
FIG. 1H is an SEM image of a Group 7 scaffold made with a 0.8 weight ratio of PEG using 100-600 μm diameter PEG particles.
Figure 1I:
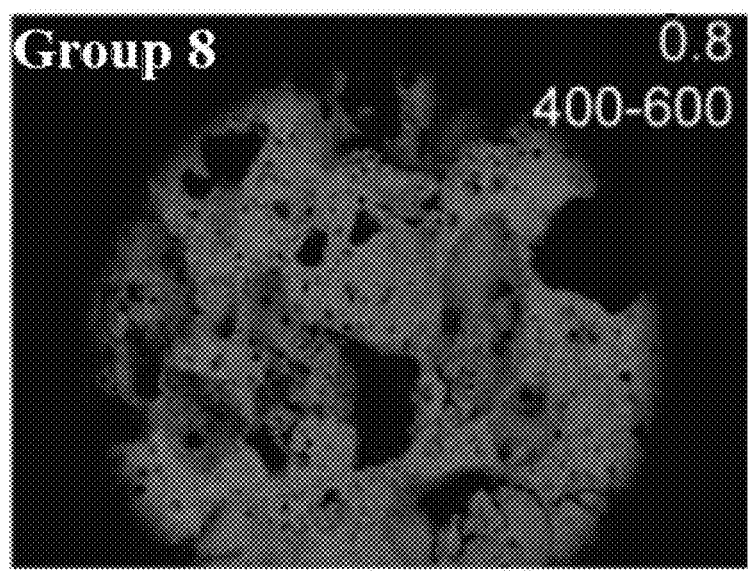
FIG. 1I is an SEM image of a Group 8 scaffold made with a 0.8 weight ratio of PEG using 400-600 μm diameter PEG particles.
Figure 1J:
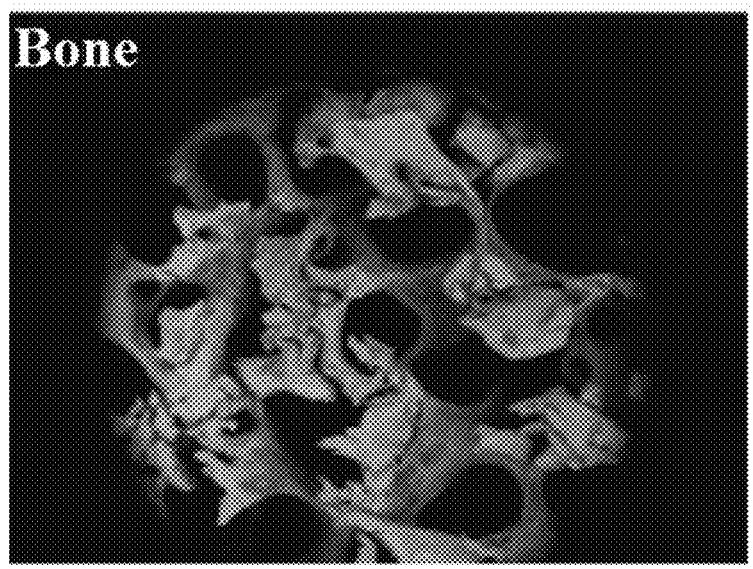

All scaffolds display surface porosities with pore sizes<100 µm, resulting from water present between crystal grains when the tannin-hydroxyapatite resin sets. Scaffolds manufactured with PEG also display porosities with pore sizes>100 µm that vary with the content and size of PEG particles (FIG. 1B-FIG. 1I). In contrast, the control group manufactured without PEG particles displays a smooth, featureless topography with only small cavities dispersed along the scaffold surface (FIG. 1A).

FIG. 1A-1J show that the amount of unreacted PTSDP appears to increase with increasing the PEG content from 0.4 to 1 g of PEG/g of tannin-hydroxyapatite powder for each PEG particle size, and decrease with increasing the size of PEG particles for any PEG content, except for the scaffold groups manufactured using 0.8 g of PEG/g of tannin-hydroxyapatite powder (Group 6, 7, and 8). At the lowest amount of PEG content (0.4 g/g) the 100-600 µm groups contain significantly less unreacted PTSDP than the 100-400 or 400-600 µm groups (p<0.001), while at larger PEG amounts (0.8 g/g), the 400-600 µm scaffolds contain less unreacted PTSDP than the 100-600 µm (P=0.05*) or 100-400 µm (P=0.008*) groups. Between groups with different particle size; the increase in unreacted PTSDP is particularly pronounced in the samples manufactured using the 100-600 µm PEG particles (Group 2, 4, and 7). This results in a 382% (p<0.001) increase in unreacted PTSDP as the amount of PEG increases from 0.4 g to 0.8 g/g, compared to a 13% and 20% increase for the samples manufactured using 100-400 and 400-600 µm PEG particles, respectively.

PEG is hydrophilic, readily absorbs water, and typically creates a hydration shell containing 1-4 molecules of water per subunit of PEG [Crupi, V. et al., Raman spectroscopic study of water in the poly(ethylene glycol) hydration shell, *Journal of Molecular Structure*, 1999, 381, 207—incorporated herein by reference in its entirety]. When the size of the PEG particles decreases, the total surface area will commensurately increase for each content category. Water should be getting out of the PTSDP to form a hydration shell on the surface of PEG particles, with smaller particles pulling more water from the reaction than larger ones. For any given PEG content, the use of larger PEG particle sizes (400-600 µm compared to 100-600 µm) reduced the total porosity, which is consistent with the theory that smaller particles pull more water from the reaction, thus increasing the scaffold porosity [Natarajan V., et al., Preparation and properties of tannic acid cross-linked collagen scaffold and its application in wound healing, *J Biomed Mater Res B Appl Biomater*, 2013, 101, 560—incorporated herein by reference in its entirety]. During the PTSDP dissolution/precipitation reaction, PEG can also directly interfere with the precipitation of dissolved PTSDP onto PEG particles. DSC and XRD analysis was used to verify the leaching of PEG particles from the tannin-hydroxyapatite scaffolds. Calorimetric results show complete leaching of PEG particles after 24 h (FIG. 2) resulting in the production of scaffolds with variable porosity. The melting temperature of PEG (20,000 MW) is 63-66° C. There is a clear negative heat flow peak at 60-66° C. that is attributed to the melting of solid PEG trapped within the tannin-hydroxyapatite resin scaffold for untreated samples (0 h) and samples leached for 2.5 h, but this change is not seen when samples are leached for 24, 32 and 56 h, indicating complete removal of PEG. XRD and Rietveld powder analysis corroborate the DSC and XRD results and confirm the complete leaching of PEG particles from all tannin-hydroxyapatite scaffold groups after 24 h (FIG. 3). The spectrogram shows no peaks typical of pure PEG in all tannin-hydroxyapatite scaffold groups. The complete removal of PEG particles indirectly indicates the presence of a network of interconnected pores forming inside the materials. This is critical to promote optimal tissue regeneration in vitro and in vivo [Annabi, N., et al., Controlling the Porosity and Microarchitecture of Hydrogels for Tissue Engineering, Tissue Eng Part B Rev. 2010, 16, 371; Okaji, R., et al., Interconnected Pores on the Walls of a Polymeric Honeycomb Monolith Structure Created by the Unidirectional Freezing of a Binary Polymer Solution, *J Mater Sci*, 2013, 48, 2038; Vízquez, B., et al., Acrylic bone cements modified with beta-TCP particles encapsulated with poly(ethylene glycol), *Biomaterials* 2005, 26, 4309; Schultz, K. M., et al., Measuring dynamic cell-material interactions and remodeling during 3D human mesenchymal stem cell migration in hydrogels, *Proc Natl Acad Sci USA*, 2015, 112, E3757; Vu, L. T., et al., Cell migration on planar and three-dimensional matrices: a hydrogel-based perspective, *Tissue Eng Part B Rev*, 2015, 21, 67—each incorporated herein by reference in its entirety].

Scaffold Porosity and Mechanical Properties

In this study scaffold porosity was investigated via micro computed tomography µCT analysis and pycnometry. In FIG. 4B-FIG. 4J, micro computed tomography (µCT) images demonstrate the presence of pores larger than 100 µm for all groups manufactured using PEG particles, in contrast to the control sample made without PEG (FIG. 4A).

FIG. 5 illustrates the pore size distribution for tannin-hydroxyapatite scaffolds from Groups 0, 3, and 8. The results reveal different profiles of porosity for the different scaffold groups. When using 100-400 µm PEG particles, the pore size distribution ranges from 40 to 300 µm, with the highest percentage of pore sizes falling between 100 and 120 µm. When using 100-600 µm PEG particles, the pore size distribution ranges from 40 to 480 µm, with the highest percentage of pore sizes falling between 100 and 160 µm. Finally, when using 400-600 µm PEG particles the pore size distribution ranges from 40 to 480 µm, with the highest percentage of pore sizes falling approximately between 220 and 320 µm. Vázquez et al. show that PEG can reduce the particle size of PTSDP 100-fold (584 µm to 6 µm in diameter), and affects the properties of PTSDP particles when as little as 0.4% is adsorbed onto the surface of PTSDP particles [Vázquez et al., Acrylic bone cements modified with beta-TCP particles encapsulated with poly(ethylene glycol), *Biomaterials*, 2005, 26, 4309—incorporated herein by reference in its entirety]. This directly influences the surface area of PTSDP available for precipitation to occur. Thus, PEG can directly adsorb onto the surface of PTSDP particles, thereby influencing the surface area of PTSDP available for precipitation to occur.

The overall macroporosity of all tannin-hydroxyapatite scaffolds is shown in FIG. 6. The results indicate that the tannin-hydroxyapatite resin scaffolds manufactured using PEG particles display a macroporosity that ranges from 10% to 40%, increasing in tandem with the content and size of PEG particles. The percentage of macroporosity appears highest in the scaffolds manufactured with PEG content of 0.8 g/g and particle size 400-600 µm, which is significantly higher than all groups except Groups 5 and 9. The percentage of macroporosity is around 80% for decellularized bone scaffolds. The chemical composition and physical parameters (porosity, pore size, etc.) greatly influence the mechanical properties of biomaterial scaffolds. For a given chemical composition, an increase in scaffold porosity results in decreased mechanical stiffness [Ghassemieh, E., Morphology and compression behaviour of biodegradable scaffolds produced by the sintering process, *Proc Inst Mech Enrg H,* 2008, 222, 1247—incorporated herein by reference in its entirety]. In this study, both the particle size and content of PEG affected the porosity, as well as the pore distribution of the scaffolds, resulting in PTSDP scaffold groups characterized by variable compressive strength, ranging from 0.20±0.03 MPa to 1.57±0.27 MPa for samples manufactured using PEG particles as shown in FIG. 7. The reduction in compressive strength associated with increasing porosity has been observed in other ceramics [Chen, Q., et al., Modelling of the strength-porosity relationship in glass-ceramic foam scaffolds for bone repair, *Journal of the European Ceramic Society,* 2014, 34, 2663; Zhang, Y., et al., In-situ hardening hydroxyapatite-based scaffold for bone repair, *J Mater Sci Mater Med,* 2006, 17, 437—each incorporated herein by reference in its entirety]. Overall, the compressive strength appears to decrease as the amount of PEG increases regardless of the PEG particle size. Groups with a narrower particle size distribution and larger particle size are consistently stronger. The samples manufactured with the 400-600 µm PEG particles are stronger than the 100-400 or 100-600 µm ones, and the 100-600 µm are stronger than the 100-400 µm ones. The larger pore diameter can produce larger mean inter-pore strut thickness. Al-Munajjed et al. [Al-Munajjed A. A., et al., Influence of pore size on tensile strength, permeability and porosity of hyaluronan-collagen scaffolds, *J Mater Sci Mater Med.* 2008, 19, 2859—incorporated herein by reference in its entirety] have observed this behavior in some hyaluronan-collagen scaffolds, and this can explain the difference in mechanical strength observed [Al-Munajjed A. A., et al., Influence of pore size on tensile strength, permeability and porosity of hyaluronan-collagen scaffolds, *J Mater Sci Mater Med.* 2008, 19, 2859; Stern R., et al., The many ways to cleave hyaluronan, *Biotechnol Adv.* 2007, 25, 537; Pennella, F., et al. A survey of methods for the evaluation of tissue engineering scaffold permeability, *Ann Biomed Eng,* 2013, 41, 2027; Park, S., et al., Microstructural parameter-based modeling for transport properties of collagen matrices, *J Biomech Eng.* 2015, 137, 061003—each incorporated herein by reference in its entirety].

Interestingly, tannin-hydroxyapatite scaffolds manufactured without PEG particles show a compressive strength of 15.18±2.7 MPa, almost twice as much as decellularized bone scaffolds (6.3±1.14 MPa). The significant reduction in compressive strength observed for scaffolds manufactured using PEG particles compared to control samples (no PEG) indicates a relation between the scaffold macroporosity and mechanical properties. Regression analysis was used to estimate the correlation strength between scaffold porosity (as measured by pycnometry) and compressive strength (FIG. 8). When the compressive strength is plotted against the macroporosity the $R^2=0.7358$, indicating a strong relationship between the macroporosity and the ultimate compressive strength of the scaffolds. Future systematic studies are necessary to fully understand the relation between structural parameters and mechanical compliance so that optimal scaffolds can be developed for specific biomedical applications.

Derivation and Characterization of iPSC-MPs

Mesenchymal progenitors were derived from the pluripotent stem cell line 1013A as previously described [de Peppo G. M., et al., Engineering bone tissue substitutes from human induced pluripotent stem cells, *Proc Natl Acad Sci USA.* 2013, 110, 8680—incorporated herein by reference in its entirety]. Colonies of 1013A cells display typical iPSC morphology and are positive for the pluripotency markers OCT4, SOX2, and TRA-1-60 as shown in FIG. 9A-FIG. 9D. In contrast, derived mesenchymal progenitors display a fibroblastic-like morphology (FIG. 10A), and are negative for pluripotency (OCT4, SOX2, TRA-1-60) (FIG. 10B-FIG. 10D) and hematopoietic (CD31, CD34, CD45) markers (FIG. 11J-FIG. 11L). On the other hand, the cells display a high expression of markers typical of primary mesenchymal stem cells, including CD13, CD29, CD44, CD49e, CD73, CD81, CD90, CD105, and CD151 as shown in FIG. 11A-FIG. 11I.

Attachment, Viability and Osteogenic Differentiation of iPSC-MPs

Scaffold features such as composition, porosity, shape, pore size, interconnectivity, and mechanical properties are all known to affect cell attachment, viability, and differentiation. In order to achieve a high yield of attached cells following seeding, two protocols were established and tested in this study. The number of attached cells dispersed across the entire surface of the scaffolds is much higher when using protocol 2 as shown in FIG. 12D and FIG. 12E, and similar to what is achieved with decellularized bone scaffolds (FIG. 12A). Increased cell attachment is confirmed by the reduced number of non-adherent cells as shown in FIG. 13, and increased fluorescence measured following incubation with PrestoBlue® reagent as shown in FIG. 14. The increased cell seeding efficiency achieved with protocol 2 is similar irrespective of the scaffold group used in the study, suggesting that the structural parameters of the PTSDP scaffolds investigated in this study have a negligible effect on cell attachment. Cell survival and tissue formation were estimated via live/dead assay. Irrespective of the scaffold group, cells display similar viability when cultured under osteogenic conditions for 3 days (FIG. 15A-FIG. 15I), 3 weeks (FIG. 16A-FIG. 16I), and 7 weeks (FIG. 17A-FIG. 17I). Interestingly, no major differences in cell viability are seen when comparing tannin-hydroxyapatite with decellularized bone scaffolds (FIG. 15J, FIG. 16J, FIG. 17J), indicating that the scaffolds developed in this study are cytocompatible and can be used to culture iPSC-MPs. The analysis also reveals increased cell density and changes in cell morphology and alignment for all groups investigated, indicating ongoing tissue formation and cell differentiation [Amini, A. R., et al., Bone Tissue Engineering: Recent Advances and Challenges, *Crit Rev Biomed Eng,* 2012, 40, 363—incorporated herein by reference in its entirety]. PTSDP scaffolds appear to support osteogenic differentiation of different types of stem cells, including human BMSCs, stem cells, deciduous teeth stem cells, and transduced hiPSC-MSCs, a behavior that has been observed in several published works on calcium phosphate [He, F., et al., Improvement of cell response of the poly(lactic-co-glycolic acid)/calcium phosphate cement composite scaffold with unidirectional pore structure by the surface immobilization of collagen via plasma treatment, *Colloids Surf B Biointerfaces*, 2013, 103, 209; Zhang, H. X., et al., Biocompatibility and osteogenesis of calcium phosphate composite scaffolds containing simvastatin-loaded PLGA microspheres for bone tissue engineering, *J Biomed Mater Res A*, 2015, 103, 3250; Magin, C. M., et al., Bio-inspired 3D microenvironments: a new dimension in tissue engineering, *Biomed Mater*, 2016, 11, 022001—each incorporated herein by reference in its entirety], human umbilical cord MSCs [Lian, J., et al., Effects of Serial Passage on the Characteristics and Cardiac and Neural Differentiation of Human Umbilical Cord Wharton's Jelly-Derived Mesenchymal Stem Cells, Stem Cells Int. 2016, 2016:9291013; Nagamura-Inoue, T. et al., Umbilical cord-derived mesenchymal stem cells: Their advantages and potential clinical utility, *World J Stem Cells*, 2014, 6, 195—each incorporated herein by reference in its entirety], and human embryonic stem cells [Rao, V., et al., Adenosine Signaling Mediates Osteogenic Differentiation of Human Embryonic Stem Cells on Mineralized Matrices, *Front Bioeng Biotechnol*, 2015, 3, 185; Kim, H. D., et al., High throughput approaches for controlled stem cell differentiation, *Acta Biomater*, 2016, 34, 21—each incorporated herein by reference in its entirety].

However, no studies exist on the effects of macro PTSDP scaffolds on the osteogenic differentiation of human iPSC-MPs. Differentiation toward the osteogenic lineage is associated with the controlled up-regulation of specific genes that regulate the differentiation process and/or play a role in the formation of new tissue [Gowri, A. M., et al., Foetal stem cell derivation & characterization for osteogenic lineage, *Indian J Med Res*, 2013, 137, 308—incorporated herein by reference in its entirety]. Also, master transcription factors can control the expression of downstream genes in the early phase of osteogenic differentiation including COL1A1 and OPN.

Other important markers of osteogenic differentiation are the metalloenzyme ALPL, the tyrosine kinase PDGFRB, and RUNX2 [de Peppo G. M., et al., Engineering bone tissue substitutes from human induced pluripotent stem cells, *Proc Natl Acad Sci U.S.A*, 2013, 110, 8680; Gulseren, G., et al., Alkaline Phosphatase-Mimicking Peptide Nanofibers for Osteogenic Differentiation, Biomacromolecules 2015, 16, 2198—each incorporated herein by reference in its entirety]. Differentiation toward the osteogenic lineage was studied via real-time PCR as shown in FIG. 18A-FIG. 18J. Here, hash signs denote a significant expression change compared to day 0. Asterisks denote a significant difference between 3 and 7 weeks. Where a particular group has a number or "B" at the top of its bar, those labels denote the group or groups that have a significantly different expression level. Except in a few cases, no substantial increase in the expression level of the analyzed genes is observed at week 3. In contrast, a significantly increased expression is observed after week 7 for most of the PTSDP scaffold groups. For example, the expression of RUNX2 is significantly increased ($P<0.05$) at week 7 (FIG. 18B) compared to week 3 (FIG. 18A) for Group 5, 7, 8 and 9, while the expression of COL1A1 (FIG. 18C and FIG. 18D) is significantly increased ($P<0.05$) for Group 1, 2, 3, 4, 8 and 9. Interestingly, the expression of RUNX2 and COL1A1 in PTSDP scaffolds is similar to that of decellularized bone. Expression of ALPL and OPN is significantly higher ($P<0.05$) at week 7 in Group 4 (FIG. 18F and FIG. 18H) compared to the other PTSDP groups and decellularized bone scaffolds, suggesting that scaffolds with selected porosity and mechanical properties could support the differentiation of 1013A-MP towards more mature osteoblast cells. Expression of PDGFRB significantly increases at week 7 (FIG. 18J) compared to week 3 (FIG. 18I) for all PTSDP groups and decellularized bone. Finally, the expression level of PDGFRB at week 7 (FIG. 18J) is comparable for all PTSDP groups (except Group 9) and decellularized bone scaffolds. Taken together, these results show that the expression of bone-specific genes generally increases during the culture period but the level of expression is different when cells are cultured onto PTSDP scaffold groups with different porosity and mechanical properties, indicating an effect induced by the scaffold parameters on cell differentiation. Unfortunately, it is currently unclear which particular scaffold parameter is responsible for the observed outcomes. Scaffold features can have an independent or combined effect on cell behavior, and the specific biological response to the scaffolding materials also depends on the specific phenotype and stage of development of the cells tested [Brown, B. N., et al., Extracellular matrix as an inductive scaffold for functional tissue reconstruction, *Transl Res.*, 2014, 163, 268; Zhang, H. X., et al., Biocompatibility and osteogenesis of calcium phosphate composite scaffolds containing simvastatin-loaded PLGA microspheres for bone tissue engineering, *J Riomed Mater Res A*, 2015, 103, 3250—each incorporated herein by reference in its entirety]. This complex cell-material interaction makes it difficult to draw conclusions regarding the relative contribution of each scaffold parameter on cellular response, as well as to compare studies conducted by different groups using different biomaterial scaffolds and cell lines. Systematic studies that address these issues are therefore encouraged before optimal scaffolds can be developed and used for specific bone engineering applications.

Instead of scaffolds based mainly on calcium phosphate, scaffolds based on porous tannin spray-dried powder (PTSDP) have been developed here for use in clinical settings as a bone graft and for a variety of orthopedic applications. Interfacing PTSDP scaffolds with bone-forming cells holds the potential to enhance their healing properties, and a few studies have recently reported such attempts using non-porous scaffold configurations. However, scaffold porosity is critical to enable tissue formation in vitro and facilitate bone replacement following implantation. In this invention, macroporous PTSDP scaffolds were developed with an interconnected porosity that mimics the bone micro-environment, with an objective to engineer bone grafts with enhanced healing properties. Scaffold porosity could be tuned by varying the total amount and particle size of the non-toxic PEG porogen. While PEG has been used as a porogen in hydrogel and polymeric scaffolds, this invention is the first report of ceramic scaffolds with PEG as a macroporous porogen tested in vitro. The results show that macro PTSDP scaffolds with defined structural parameters and mechanical properties can be fabricated using our engineering approach based on a moldable tannin-hydroxyapatite paste using PEG particles as a porogen. These macroporous scaffolds support cell attachment, viability, and osteogenic differentiation of iPSC-derived osteocompotent cells, thereby opening the possibility to grow functional bone grafts of clinical relevance for autologous dental and orthopedic applications. PTSDP scaffolds with an advantageous combination of porosity and mechanical properties could also be used to develop patient-specific bone grafts as experimental platforms to study bone development and pathology, screen new drugs, and test implant materials within a context that highly reflects the native tissue.

The invention claimed is:

1. A biocompatible bone graft comprising:
   a porous scaffold structure comprising a tannin-hydroxyapatite resin which has a 17-80 vol % porosity, a pore diameter of 40-300 µm, and a compressive strength of 0.15-1.90 MPa;
   a population of osteocompetent stem cells obtained from a mammalian donor; and
   a growth medium.

2. The biocompatible bone graft of claim 1, wherein the tannin-hydroxyapatite resin comprises 50-90 wt % tannin and 10-50 wt % hydroxyapatite.

3. The biocompatible bone graft of claim 1, wherein the osteocompetent stem cells are derived from a sample of bone marrow, periosteum, dermal fibroblasts, or adipose tissue.

4. The biocompatible bone graft of claim 1, wherein at least 50% of the osteocompetent stem cells express CD13, CD29, CD44, CD90, or CD105.

5. The biocompatible bone graft of claim 1 further comprising a growth factor.

6. The biocompatible bone graft of claim 5 wherein the growth factor is at least one selected from the group consisting of β-glycerophosphate, dexamethasone, ascorbic acid, transforming growth factor β (TGF-$β_1$), fibroblast growth factor (FGF), active vitamin D, a bone morphogenic protein (BMP), and parathyroid hormone.

7. The biocompatible bone graft of claim 1 further comprising adsorbed or chemically-linked osteoinductive biomolecules on the surface of the porous scaffold structure.

8. The biocompatible bone graft of claim 1 wherein the porous scaffold structure further comprises at least one biodegradable polymer selected from the group consisting of poly lactic-co-glycolic acid, poly lactic acid, poly glycolic acid, polyanhydride, poly(ortho)ester, polyurethane, poly(butyric acid), poly(valeric acid), polycaprolactone, poly(lactide-co-caprolactone), and poly(trimethylene carbonate).

9. The biocompatible bone graft of claim 1, intended to be placed in a bone wound site in a patient, the bone wound site comprising:
   a first portion of bone on a first side of the porous scaffold structure; and
   a second portion of bone on a second side of the porous scaffold structure.

10. The biocompatible bone graft of claim 9 further comprising a mineralized osseous tissue supported by the porous scaffold structure and connecting the first portion of bone with the second portion of bone.

11. The biocompatible bone graft of claim 9 wherein the patient is the mammalian donor.

12. The biocompatible bone graft of claim 1 further comprising a prosthesis.

13. The biocompatible bone graft of claim 1 further comprising a second biocompatible bone graft wherein the second biocompatible bone graft has a different size, shape, and/or composition.

14. A method of monitoring the biocompatible bone graft of claim 1 present within a bone wound site in a patient, the method comprising monitoring the growth of the osteocompetent stem cells up to 16 weeks by X-ray imaging, MRI, or ultrasonography.

15. A method of monitoring the biocompatible bone graft of claim 1 present within a bone wound site in a patient, the method comprising monitoring the growth of the osteocompetent stem cells up to 16 weeks by the expression level of at least one osteogenic differentiation gene selected from the group consisting of RUNX2, COL1A1, ALPL, OPN, and PDGFRB.

16. A method of screening a bone disease drug comprising:
   adding the bone disease drug to the biocompatible bone graft of claim 1;
   growing the osteocompetent stem cells in the presence of the bone disease drug to form a treated biocompatible bone graft having a new bone tissue;
   measuring the porosity, density, and/or compressive strength of the treated biocompatible bone graft; and
   comparing the porosity, density, and/or compressive strength of the treated biocompatible bone graft to a biocompatible bone graft of claim 1 that has not been treated with the bone disease drug.

17. The method of claim 16 wherein the bone disease drug is denosumab, teriparatide, alendronate, risedronate, ibandronate, zoledronic acid, teriparatide, strontium ranelate, aluminium chlorohydrate, or odanacatib.

18. A method of making a porous scaffold structure comprising:
   mixing porous tannin powder particles, dried polyethylene glycol particles, and hydroxyapatite to form a powder mixture;
   mixing the powder mixture with an organic acid and a formaldehyde solution to form a liquid mixture;
   incubating the liquid mixture to form a set scaffold; and
   heating the set scaffold to remove the polyethylene glycol particles to form the porous scaffold structure.

19. The method of claim 18 wherein the powder mixture further comprises a biodegradable polymer.

20. The method of claim 19 wherein the biodegradable polymer is at least one selected from poly lactic-co-glycolic acid, poly lactic acid, poly glycolic acid, polyanhydride, poly(ortho)ester, polyurethane, poly(butyric acid), poly(valeric acid), polycaprolactone, poly(lactide-co-caprolactone), and poly(trimethylene carbonate).

* * * * *